(12) United States Patent
Hilderbrand et al.

(10) Patent No.: US 10,287,256 B2
(45) Date of Patent: May 14, 2019

(54) SELECTIVE SULFONATION OF BENZODIAZEPINE DERIVATIVES

(71) Applicant: IMMUNOGEN, INC., Waltham, MA (US)

(72) Inventors: Scott A. Hilderbrand, Swampscott, MA (US); Benjamin M. Hutchins, Boxborough, MA (US)

(73) Assignee: IMMUNOGEN, INC., Waltham, MA (US)

( * ) Notice: Subject to any disclaimer, the term of this patent is extended or adjusted under 35 U.S.C. 154(b) by 0 days.

(21) Appl. No.: 15/820,648

(22) Filed: Nov. 22, 2017

(65) Prior Publication Data

US 2018/0208562 A1    Jul. 26, 2018

Related U.S. Application Data

(60) Provisional application No. 62/425,761, filed on Nov. 23, 2016.

(51) Int. Cl.
| | | |
|---|---|---|
| *C07D 243/26* | (2006.01) |
| *C07D 487/04* | (2006.01) |
| *C07K 16/28* | (2006.01) |
| *C07K 16/30* | (2006.01) |

(52) U.S. Cl.
CPC ......... *C07D 243/26* (2013.01); *C07D 487/04* (2013.01); *C07K 16/2866* (2013.01); *C07K 16/2896* (2013.01); *C07K 16/30* (2013.01); *C07K 2317/526* (2013.01)

(58) Field of Classification Search
CPC ........................... C07D 243/26; C07D 487/04; C07K 16/2866; C07K 16/2896; C07K 16/30; C07K 2317/526
See application file for complete search history.

(56) References Cited

U.S. PATENT DOCUMENTS

| | | |
|---|---|---|
| 8,557,966 B2 | 10/2013 | Ab et al. |
| 2007/0092940 A1 | 4/2007 | Eigenbrot et al. |
| 2009/0010945 A1 | 1/2009 | Alley et al. |
| 2012/0213705 A1 | 8/2012 | Dimasi et al. |
| 2015/0359903 A1 | 12/2015 | Widdison |
| 2015/0359904 A1 | 12/2015 | Widdison |
| 2016/0106863 A1 | 4/2016 | Chari et al. |
| 2016/0207949 A1 | 7/2016 | Zhao |
| 2017/0014522 A1 | 1/2017 | Yoder et al. |
| 2017/0029514 A1 | 2/2017 | Kovtun et al. |

FOREIGN PATENT DOCUMENTS

| | | | |
|---|---|---|---|
| EP | 2425860 A1 | 3/2012 | |
| WO | 1996/14339 A1 | 5/1996 | |
| WO | 2010/091150 A1 | 8/2010 | |
| WO | 2012/128868 A1 | 9/2012 | |
| WO | 2014/134457 A2 | 9/2014 | |
| WO | 2015/196089 A1 | 12/2015 | |
| WO | 2015/196167 A1 | 12/2015 | |
| WO | 2016/036861 A1 | 3/2016 | |
| WO | 2016/141285 A1 | 9/2016 | |
| WO | WO 2017/004025 * | 1/2017 | ............. A61K 47/48 |

OTHER PUBLICATIONS

U.S. Appl. No. 15/195,269, filed Jun. 28, 2016, 2017-0014522, Published.
Kumaresan et al., Evaluation of ketone-oxime method for developing therapeutic on-demand cleavable immunoconjugates. Bioconjug Chem. Jun. 2008;19(6):1313-8.
Rodwell et al., Site-specific covalent modification of monoclonal antibodies: in vitro and in vivo evaluations. Proc Natl Acad Sci U S A. Apr. 1986;83(8):2632-6.
Stimmel et al., Site-specific conjugation on serine right-arrow cysteine variant monoclonal antibodies. J Biol Chem. Sep. 2000;275(39):30445-50.

* cited by examiner

*Primary Examiner* — Erich A Leeser
(74) *Attorney, Agent, or Firm* — McCarter & English, LLP; Steven G. Davis; Xin Zhang

(57) ABSTRACT

The invention relates to novel methods of preparing cell-binding agent-cytotoxic agent conjugates, wherein the cytotoxic agent is an imine-containing cytotoxic agent bearing a maleimide group. In some embodiments, the cell-binding agent (CBA) is covalently linked to the cytotoxic agent through an engineered Cys, such as an engineered Cys in the heavy chain CH3 domain, at a position corresponds to the EU/OU numbering position 442 (or C442) on an antibody CBA. The invention also provides conjugates prepared by the methods of the present invention, compositions and methods useful for inhibiting abnormal cell growth or treating a proliferative disorder in a mammal using the conjugates of the invention.

19 Claims, 4 Drawing Sheets

Specification includes a Sequence Listing.

SEQUENCE LISTING

<160> NUMBER OF SEQ ID NOS: 27

<210> SEQ ID NO 1
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:7
      Synthetic peptide"

<400> SEQUENCE: 1

Ala Leu Ala Leu
1

<210> SEQ ID NO 2
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Beta-Ala

<400> SEQUENCE: 2

Xaa Leu Ala Leu
1

<210> SEQ ID NO 3
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Gly Phe Leu Gly
1

<210> SEQ ID NO 4
<211> LENGTH: 5
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 4

Gly Tyr Phe Met Asn
1               5

<210> SEQ ID NO 5
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (14)..(14)
<223> OTHER INFORMATION: Gln, His or Arg
<220> FEATURE:
<221> NAME/KEY: VARIANT
<222> LOCATION: (18)..(18)
<223> OTHER INFORMATION: His, Asn or Arg
<220> FEATURE:
<221> NAME/KEY: VARIANT
<222> LOCATION: (21)..(21)
<223> OTHER INFORMATION: Glu, Thr, Ser, Ala or Val
<220> FEATURE:
<221> NAME/KEY: MISC_FEATURE
<222> LOCATION: (1)..(23)
<223> OTHER INFORMATION: /note="Variant residues given in the sequence
      have no preference with respect to those in the annotations
      for variant positions"

<400> SEQUENCE: 5

Arg Ile His Pro Tyr Asp Gly Asp Thr Phe Tyr Asn Gln Lys Ala Ala
1               5                   10                  15

Phe Gln Ala Ala Gly Ala Ala
            20

<210> SEQ ID NO 6
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Tyr Asp Gly Ser Arg Ala Met Asp Tyr
1               5

<210> SEQ ID NO 7
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Lys Ala Ser Gln Ser Val Ser Phe Ala Gly Thr Ser Leu Met His
1               5                   10                  15

<210> SEQ ID NO 8
<211> LENGTH: 7
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Arg Ala Ser Asn Leu Glu Ala
1               5

<210> SEQ ID NO 9
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Gln Gln Ser Arg Glu Tyr Pro Tyr Thr
1               5

<210> SEQ ID NO 10
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Arg Ile His Pro Tyr Asp Gly Asp Thr Phe Tyr Asn Gln Lys Phe Gln
1               5                   10                  15

Gly

<210> SEQ ID NO 11
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
                20                  25                  30

Phe Met Asn Trp Val Lys Gln Ser Pro Gly Gln Ser Leu Glu Trp Ile
            35                  40                  45

Gly Arg Ile His Pro Tyr Asp Gly Asp Thr Phe Tyr Asn Gln Lys Phe
        50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser Ala Ser Thr Lys Gly Pro Ser Val Phe Pro
        115                 120                 125
```

-continued

Leu Ala Pro Ser Ser Lys Ser Thr Ser Gly Gly Thr Ala Ala Leu Gly
                130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Cys Leu Ser Pro Gly
                435                 440                 445

<210> SEQ ID NO 12
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
                20                  25                  30

Gly Thr Ser Leu Met His Trp Tyr His Gln Lys Pro Gly Gln Gln Pro
            35                  40                  45

Arg Leu Leu Ile Tyr Arg Ala Ser Asn Leu Glu Ala Gly Val Pro Asp
 50                  55                  60

Arg Phe Ser Gly Ser Gly Ser Lys Thr Asp Phe Thr Leu Asn Ile Ser
 65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
            210                 215

```
<210> SEQ ID NO 13
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13
```

Asp Ile Val Leu Thr Gln Ser Pro Leu Ser Leu Ala Val Ser Leu Gly
 1               5                  10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
            35                  40                  45

Arg Leu Leu Ile Tyr Arg Ala Ser Asn Leu Glu Ala Gly Val Pro Asp
 50                  55                  60

Arg Phe Ser Gly Ser Gly Ser Lys Thr Asp Phe Thr Leu Thr Ile Ser
 65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr

```
                      165                 170                 175
Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 14
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 15
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Asn Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110
```

<210> SEQ ID NO 16
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 16

```
Asp Ile Val Leu Thr Gln Ser Pro Leu Ser Leu Ala Val Ser Leu Gly
1               5                   10                  15
Gln Pro Ala Ile Ile Ser Cys Lys Ala Ser Gln Ser Val Ser Phe Ala
            20                  25                  30
Gly Thr Ser Leu Met His Trp Tyr His Gln Lys Pro Gly Gln Gln Pro
        35                  40                  45
Arg Leu Leu Ile Tyr Arg Ala Ser Asn Leu Glu Ala Gly Val Pro Asp
    50                  55                  60
Arg Phe Ser Gly Ser Gly Ser Lys Thr Asp Phe Thr Leu Thr Ile Ser
65                  70                  75                  80
Pro Val Glu Ala Glu Asp Ala Ala Thr Tyr Tyr Cys Gln Gln Ser Arg
                85                  90                  95
Glu Tyr Pro Tyr Thr Phe Gly Gly Gly Thr Lys Leu Glu Ile Lys Arg
            100                 105                 110
```

<210> SEQ ID NO 17
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 17

```
Ser Ser Ile Met His
1               5
```

<210> SEQ ID NO 18
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 18

```
Tyr Ile Lys Pro Tyr Asn Asp Gly Thr Lys Tyr Asn Glu Lys Phe Lys
1               5                   10                  15
Gly
```

<210> SEQ ID NO 19
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 19

```
Glu Gly Gly Asn Asp Tyr Tyr Asp Thr Met Asp Tyr
```

<210> SEQ ID NO 20
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 20

Arg Ala Ser Gln Asp Ile Asn Ser Tyr Leu Ser
1               5                   10

<210> SEQ ID NO 21
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 21

Arg Val Asn Arg Leu Val Asp
1               5

<210> SEQ ID NO 22
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 22

Leu Gln Tyr Asp Ala Phe Pro Tyr Thr
1               5

<210> SEQ ID NO 23
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: MOD_RES
<222> LOCATION: (2)..(2)
<223> OTHER INFORMATION: Any amino acid

<400> SEQUENCE: 23

Gln Xaa Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys

```
                85                  90                  95
Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120

<210> SEQ ID NO 24
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys Arg
            100                 105

<210> SEQ ID NO 25
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140
```

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Asp Glu Leu Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Cys Leu Ser
    435                 440                 445

Pro Gly
    450

<210> SEQ ID NO 26
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30
```

```
Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
        210

<210> SEQ ID NO 27
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"
<220> FEATURE:
<221> NAME/KEY: MOD_RES
<222> LOCATION: (1)..(1)
<223> OTHER INFORMATION: Beta-Ala

<400> SEQUENCE: 27

Xaa Gly Gly Gly
1
```

SELECTIVE SULFONATION OF BENZODIAZEPINE DERIVATIVES

RELATED APPLICATION

This application claims the benefit of the filing date, under 35 U.S.C. § 119(e), of U.S. Provisional Application No. 62/425,761, filed on Nov. 23, 2016, the entire content of which, including all drawings, formulae, specification, claims and sequence listings, is incorporated herein by reference.

BACKGROUND OF THE INVENTION

Antibody-cytotoxic agent conjugates (or "antibody-drug conjugates (ADC)") and cell binding agent-drug conjugates are emerging as a powerful class of anti-tumor agents with efficacy across a range of cancers. Cell binding agent-drug conjugates (such as ADCs) are commonly composed of three distinct elements: a cell-binding agent (e.g., an antibody); a linker; and a cytotoxic moiety. The cytotoxic drug moiety can be covalently attached to lysines on the antibody, resulting in conjugates that are heterogeneous mixtures of ADCs bearing varying numbers of drugs attached at different positions on the antibody molecule. Alternatively, the cytotoxic drug moiety can be covalently linked to cysteine thiol groups on the antibody through a thiol-reactive group, such as a maleimde group, to form site-specific ADCs. Conjugation reactions between the antibodies and the cytotoxic agents are often carried out in water or an aqueous solution with small amount of an organic solvent required for solubilizing the cytotoxic agents.

Benzodiazepine compounds, including tricyclic benzodiazepines, such as pyrrolobenzodiazepines (PBD), and tetracyclic benzodiazepines, such as indolinobenzodiazepines, have been employed as cytotoxic agents in linkage with antibodies to generate ADCs, which have shown promising antitumor activities. These benzodiazepine compounds contain imine bonds, which can bind to the minor groove of DNA and interfere with DNA function, resulting in cell death. Benzodiazepine compounds generally have very low solubility in water. To solubilize the benzodiazepine compounds in the conjugation reaction with antibodies, relatively large amount of organic solvent is required, which can de-stabilize the antibodies.

Therefore, there is a need to develop new methods for preparing conjugates of cell-binding agent and imine-containing benzodiazepine drugs.

SUMMARY OF THE INVENTION

To improve the water solubility, the imine-containing benzodiazepine compounds can be treated with an imine reactive reagent, such as a bisulfite salt or a metabisulfite salt, before the conjugation reaction with antibodies to form the antibody-benzodiazepine conjugates. Sulfonation of the imine group can increase the water solubility of the benzodiazepine compounds, resulting in improved conditions for the conjugation reactions with CBAs, such as antibodies. However, nucleophilic additions between nucleophiles and α,β-unsaturated carbonyls are well known in synthetic organic chemistry. The nucleophilic addition of bisulfite to the activated olefin of a maleimide is one such example of this reaction. Therefore, when the imine-containing benzodiazepine compounds bear a maleimide, the reactive group for covalent linkage with the antibodies, the maleimide moiety and the imine moiety can both react with the bisulfite salt or the metabisulfite salt to form sulfonated maleimide and/or sulfonated imine. It is surprisingly found that reacting an imine-containing indolinobenzodiazepine compound bearing a maleimide group with a bisulfite salt or a metabisulfite salt at a low pH can selectively and effectively effect sulfonation of the imine group without significant sulfonation of the maleimide group, thereby increasing reaction yield for the conjugation reaction between the indolinobenzodiazepine compound and the antibodies. In addition, the sulfonated indolinobenzodiazepine compound has increased solubility in water, and as a result, significantly less amount of organic solvent (e.g., DMA) is required in the conjugation reaction with antibodies. The presence of large amount of organic solvent in the conjugation reaction can de-stabilize the antibodies.

The present invention provides a novel method for preparing a cell-binding agent-cytotoxic agent conjugate comprising an imine-containing cytotoxic agent bearing a maleimide group covalently linked to a cell-binding agent (CBA). In some embodiments, the present invention provides a method of preparing a cell-binding agent-cytotoxic agent conjugate comprising the steps of:

(a) reacting an imine-moiety in an imine-containing cytotoxic agent represented by the following formula:

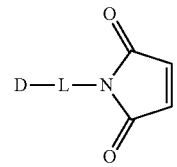

or a pharmaceutically acceptable salt thereof, with a sulfur dioxide, bisulfite salt or a metabisulfite salt in an aqueous solution at a pH of 1.9 to 5.0 to form a modified cytotoxic agent comprising a modified imine moiety represented by the following formula:

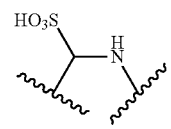

or a pharmaceutically acceptable salt thereof; and (b) reacting the modified cytotoxic agent with a cell-binding agent to form the cell-binding agent-cytotoxic agent conjugate, wherein D is an imine-containing cytotoxic compound; and L is a linker.

In some embodiments, D is an imine-containing tricyclic or tetracyclic benzodiazepine compound.

In some embodiments, D is an imine-containing tricyclic benzodiazepine compounds.

In some embodiments, D is an imine-containing tetracyclic benzodiazepine compounds.

As used herein, an imine-containing tricyclic benzodiazepine compound refers to a compound having a monocyclic ring fused to the diazepine portion of the benzodiazepine core. The monocyclic ring may contain one or more additional heteroatoms, such as oxygen, sulfur or nitrogen, and substituents such as monocyclic rings or polycyclic rings. Exemplary tricyclic benzodiazepine compounds, include, but are not limited to, pyrrolobenzodiazepines (PBD), such as those described in WO2010/043880, WO2011/130616, WO2009/016516, WO 2013/177481 and WO 2012/112708.

As used herein, an imine-containing tetracyclic benzodiazepine compound refers to a compound having a bicyclic ring fused to the diazepine portion of the benzodiazepine core. The bicyclic ring is a fused bicyclic ring optionally containing one or more additional heteroatoms, such as oxygen, sulfur or nitrogen. Exemplary tetracyclic benzodiazepine compounds, include, but are not limited to, indolinobenzodiazepines (IGNs), such as those described in WO/2010/091150, and WO 2012/128868.

In some embodiments, D is an indolinobenzodiazepine.

In some embodiments, D is a pyrrolobenzodiazepine (PBD).

Also provided by the present invention is the cell-binding agent-cytotoxic agent conjugates and modified cytotoxic agents prepared by the methods described herein.

It should be understood that any embodiments described herein, including embodiments described only under one aspect of the invention but not other aspects, and including embodiments only appearing in the Examples, can be combined with any one or more other embodiments, unless explicitly disclaimed or improper.

DETAILED DESCRIPTION OF THE INVENTION

Figure 1:
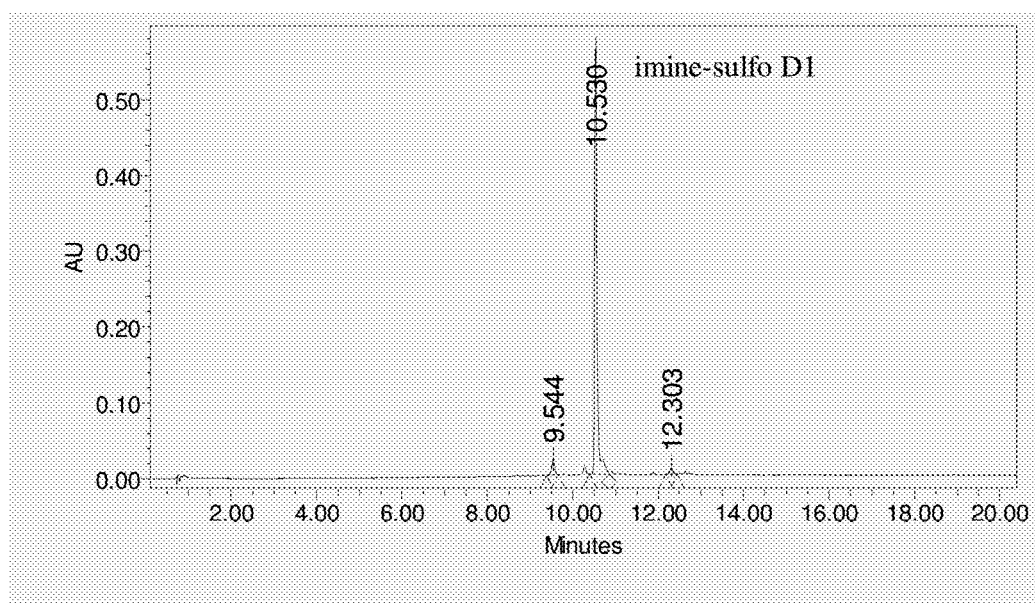
FIG. 1 shows an UPLC chromatogram of the reaction mixture of imine-containing cytotoxic agent D1 with sodium bisulfite at pH 3.3.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents that can be included within the scope of the present invention as defined by the claims. One skilled in the art will recognize many methods and materials similar or equivalent to those described herein, which could be used in the practice of the present invention.

It should be understood that any of the embodiments described herein, including those described under different aspects of the invention and different parts of the specification (including embodiments described only in the Examples) can be combined with one or more other embodiments of the invention, unless explicitly disclaimed or improper. Combination of embodiments are not limited to those specific combinations claimed via the multiple dependent claims.

Definitions

"Alkyl" or "linear or branched alkyl" as used herein refers to a saturated linear or branched monovalent hydrocarbon radical. In preferred embodiments, a straight chain or branched chain alkyl has thirty or fewer carbon atoms (e.g., $C_1$-$C_{30}$ for straight chain alkyl group and $C_3$-$C_{30}$ for branched alkyl), and more preferably twenty or fewer carbon atoms. Even more preferably, the straight chain or branched chain alkyl has ten or fewer carbon atoms (i.e., $C_1$-$C_{10}$ for straight chain alkyl group and $C_3$-$C_{10}$ for branched alkyl). In other embodiments, the straight chain or branched chain alkyl has six or fewer carbon atoms (i.e., $C_1$-$C_6$ for straight chain alky group or $C_3$-$C_6$ for branched chain alkyl). Examples of alkyl include, but are not limited to, methyl, ethyl, 1-propyl, 2-propyl, 1-butyl, 2-methyl-1-propyl, —$CH_2CH(CH_3)_2$), 2-butyl, 2-methyl-2-propyl, 1-pentyl, 2-pentyl 3-pentyl, 2-methyl-2-butyl, 3-methyl-2-butyl, 3-methyl-1-butyl, 2-methyl-1-butyl, 1-hexyl), 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like. Moreover, the term "alkyl" as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. As used herein, ($C_x$-$C_{xx}$)alkyl or $C_{x-xx}$ alky means a linear or branched alkyl having x-xx carbon atoms.

"Alkenyl" or "linear or branched alkenyl" refers to linear or branched-chain monovalent hydrocarbon radical of two to twenty carbon atoms with at least one site of unsaturation, i.e., a carbon-carbon double bond, wherein the alkenyl radical includes radicals having "cis" and "trans" orientations, or alternatively, "E" and "Z" orientations. Examples include, but are not limited to, ethylenyl or vinyl (—CH═$CH_2$), allyl (—$CH_2$CH═$CH_2$), and the like. Preferably, the alkenyl has two to ten carbon atoms. More preferably, the alkyl has two to four carbon atoms.

"Alkynyl" or "linear or branched alkynyl" refers to a linear or branched monovalent hydrocarbon radical of two to twenty carbon atoms with at least one site of unsaturation, i.e., a carbon-carbon, triple bond. Examples include, but are not limited to, ethynyl, propynyl, 1-butynyl, 2-butynyl, 1-pentynyl, 2-pentynyl, 3-pentynyl, hexynyl, and the like. Preferably, the alkynyl has two to ten carbon atoms. More preferably, the alkynyl has two to four carbon atoms.

The terms "cyclic alkyl" and "cycloalkyl" can be used interchangeably. As used herein, the term refers to the radical of a saturated carbocyclic ring. In preferred embodiments, cycloalkyls have from 3 to 10 carbon atoms in their ring structure, and more preferably from 5 to 7 carbon atoms in the ring structure. In some embodiments, the two cyclic rings can have two or more atoms in common, e.g., the rings are "fused rings." Suitable cycloalkyls include, but are not limited to cycloheptyl, cyclohexyl, cyclopentyl, cyclobutyl and cyclopropyl. In some embodiments, the cycloalkyl is a monocyclic group. In some embodiments, the cycloalkyl is a bicyclic group. In some embodiments, the cycloalkyl is a tricyclic group.

The term "cycloalklalkyl" refers to an alkyl group described above that is substituted with a cycloalkyl group.

The term "cyclic alkenyl" refers to a carbocyclic ring radical having at least one double bond in the ring structure.

The term "cyclic alkynyl" refers to a carbocyclic ring radical having at least one triple bond in the ring structure.

The term "aryl" as used herein, include substituted or unsubstituted single-ring aromatic groups in which each atom of the ring is carbon. Preferably the ring is a 5- to 7-membered ring, more preferably a 6-membered ring. Aryl groups include, but are not limited to, phenyl, phenol, aniline, and the like. The terms "aryl" also includes "polycyclyl", "polycycle", and "polycyclic" ring systems having two or more rings in which two or more atoms are common to two adjoining rings, e.g., the rings are "fused rings," wherein at least one of the rings is aromatic, e.g., the other cyclic rings can be cycloalkyls, cycloalkenyls, cycloalkynyls, or aromatic rings. In some preferred embodiments, polycycles have 2-3 rings. In certain preferred embodiments, polycyclic ring systems have two cyclic rings in which both of the rings are aromatic. Each of the rings of the polycycle can be substituted or unsubstituted. In certain embodiments, each ring of the polycycle contains from 3 to 10 carbon atoms in the ring, preferably from 5 to 7. For example, aryl groups include, but are not limited to, phenyl (benzene), tolyl, anthracenyl, fluorenyl, indenyl, azulenyl, and naphthyl, as well as benzo-fused carbocyclic moieties such as 5,6,7,8-tetrahydronaphthyl, and the like. In some embodiments, the aryl is a single-ring aromatic group. In some embodiments, the aryl is a two-ring aromatic group. In some embodiments, the aryl is a three-ring aromatic group.

The terms "heterocycle," "heterocyclyl," and "heterocyclic ring" as used herein, refers to substituted or unsubstituted non-aromatic ring structures of 3- to 18-membered rings, preferably 3- to 10-membered rings, more preferably 3- to 7-membered rings, whose ring structures include at least one heteroatom, preferably one to four heteroatoms, more preferably one or two heteroatoms. In certain embodiments, the ring structure can have two cyclic rings. In some embodiments, the two cyclic rings can have two or more atoms in common, e.g., the rings are "fused rings." Heterocyclyl groups include, for example, piperidine, piperazine, pyrrolidine, morpholine, lactones, lactams, and the like. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. Examples of heterocyclic rings include, but are not limited to, tetrahydrofurane, dihydrofuran, tetrahydrothiene, tetrahydropyran, dihydropyran, tetrahydrothiopyran, thiomorpholine, thioxane, homopiperazine, azetidine, oxetane, thietane, homopiperidine, piperidine, piperazine, pyrrolidine, morpholine, oxepane, thiepane, oxazepine, diazepine, thiazepine, 2-pyrroline, 3-pyrroline, indoline, 2H-pyrane, 4H-pyrane, dioxane, 1,3-dioxolane, pyrazoline, dithiane, dithiolane, dihydropyrane, dihydrothiene, dihydrofurane, pyrazolidinylimidazoline, imidazolidine, 3-azabicyco[3.1.0]hexane, 3-azabicyclo[4.1.0]heptane, and azabicyclo[2.2.2]hexane. Spiro moieties are also included within the scope of this definition. Examples of a heterocyclic group wherein ring atoms are substituted with oxo (=O) moieties are pyrimidinone and 1,1-dioxo-thiomorpholine.

The term "heteroaryl" as used herein, refers to substituted or unsubstituted aromatic single ring structures, preferably 5- to 7-membered rings, more preferably 5- to 6-membered rings, whose ring structures include at least one heteroatom (e.g., O, N, or S), preferably one to four or one to three heteroatoms, more preferably one or two heteroatoms. When two or more heteroatoms are present in a heteroaryl ring, they may be the same or different. The term "heteroaryl" also includes "polycyclyl", "polycycle", and "polycyclic" ring systems having two or more cyclic rings in which two or more ring atoms are common to two adjoining rings, e.g., the rings are "fused rings," wherein at least one of the rings is heteroaromatic, e.g., the other cyclic rings can be cycloalkyls, cycloalkenyls, cycloalkynyls, aryls, heteroaromatics, and/or heterocyclyls. In some preferred embodiments, polycyclic heteroaryls have 2-3 rings. In certain embodiments, preferred polycyclic heteroaryls have two cyclic rings in which both of the rings are aromatic. In certain embodiments, each ring of the polycycle contains from 3 to 10 atoms in the ring, preferably from 5 to 7 atoms in the ring. For examples, heteroaryl groups include, but are not limited to, pyrrole, furan, thiophene, imidazole, oxazole, thiazole, pyrazole, pyridine, pyrazine, pyridazine, quinoline, pyrimidine, indolizine, indole, indazole, benzimidazole, benzothiazole, benzofuran, benzothiophene, cinnoline, phthalazine, quinazoline, carbazole, phenoxazine, quinoline, purine and the like. In some embodiments, the heteroaryl is a single-ring aromatic group. In some embodiments, the heteroaryl is a two-ring aromatic group. In some embodiments, the heteroaryl is a three-ring aromatic group.

The heterocycle or heteroaryl groups can be carbon (carbon-linked) or nitrogen (nitrogen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or O-carboline.

The heteroatoms present in heteroaryl or heterocyclcyl include the oxidized forms such as NO, SO, and $SO_2$.

The term "halo" or "halogen" refers to fluorine (F), chlorine (Cl), bromine (Br) or iodine (I).

As used herein, the term "haloalkyl" refers to an alkyl, as defined herein, that is substituted by one or more halo groups as defined herein. The haloalkyl can be monohaloalkyl, dihaloalkyl or polyhaloalkyl. A monohaloalkyl can have one fluoro, chloro, bromo, or iodo substituent. Dihaloalkyl or polyhaloalkyl can be substituted with two or more of the same halo atoms or a combination of different halo groups. Examples of haloalkyl include, but are not limited to, flouromethyl, difluoromethyl, trifluoromethyl, chloroamethyl, dichloromethyl, trichloromethyl, pentafluoroethyl, heptafluoropropyl, diflurochloromethyl, dichlorofluoromethyl, difluoroehthyl, diflosoropropyl, dichloroethyl and dichloropropyl.

"Alkoxy" used herein refers to alkyl-O—, wherein alkyl is defined herein above. Examples of alkoxy include, not are not limited to, methoxy, ethoxy, propoxy, 2-propoxy, butoxy, tert-butoxy, pentyloxy, hexyloxy, and the like.

The alkyl, haloalkyl, alkoxy, alkenyl, alkynyl, cyclic alkyl, cyclic alkenyl, cyclic alkynyl, carbocyclyl, aryl, heterocyclyl and heteroaryl described above can be optionally substituted with one or more (e.g., 2, 3, 4, 5, 6 or more) substituents.

Unless specifically stated as "unsubstituted," references to chemical moieties herein are understood to also include substituted variants. For example, reference to an "alkyl"

group or moiety implicitly includes both substituted and unsubstituted variants. Examples of substituents on chemical moieties includes but is not limited to, halogen, hydroxyl, carbonyl (such as carboxyl, alkoxycarbonyl, formyl, or acyl), thiocarbonyl (such as thioester, thioacetate, or thioformate), alkoxyl, alkylthio, acyloxy, phosphoryl, phosphate, phosphonate, amino, amido, amidine, imine, cyano, nitro, azido, sulfhydryl, alkylthio, sulfate, sulfonate, sulfamoyl, sulfonamido, sulfonyl, heterocyclyl, aralkyl, or aryl or heteroaryl moiety.

"Optional" or "optionally" means that the subsequently described circumstance may or may not occur, so that the application includes instances where the circumstance occurs and instances where it does not. For example, the phrase "optionally substituted" means that a nonhydrogen substituent may or may not be present on a given atom, and, thus, the application includes structures wherein a non-hydrogen substituent is present and structures wherein a nonhydrogen substituent is not present.

The term "substituted" refers to moieties having substituents replacing a hydrogen on one or more carbons, nitrogens, oxygens or sulfurs atoms. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of the invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent may be identical or different (unless otherwise stated).

If a carbon of a substituent is described as being optionally substituted with one or more of a list of substituents, one or more of the hydrogens on the carbon (to the extent there are any) can separately and/or together be replaced with an independently selected optional substituent. If a nitrogen of a substituent is described as being optionally substituted with one or more of a list of substituents, one or more of the hydrogens on the nitrogen (to the extent there are any) can each be replaced with an independently selected optional substituent. One exemplary substituent can be depicted as —NR'R", wherein R' and R" together with the nitrogen atom to which they are attached, can form a heterocyclic ring. The heterocyclic ring formed from R' and R" together with the nitrogen atom to which they are attached can be partially or fully saturated. In some embodiments, the heterocyclic ring consists of 3 to 7 atoms. In other embodiments, the heterocyclic ring is selected from the group consisting of pyrrolyl, imidazolyl, pyrazolyl, triazolyl, tetrazolyl, isoxazolyl, pyridyl and thiazolyl.

This specification uses the terms "substituent," "radical," and "group" interchangeably.

If a group of substituents are collectively described as being optionally substituted by one or more of a list of substituents, the group can include: (1) unsubstitutable substituents, (2) substitutable substituents that are not substituted by the optional substituents, and/or (3) substitutable substituents that are substituted by one or more of the optional substituents.

If a substituent is described as being optionally substituted with up to a particular number of non-hydrogen substituents, that substituent can be either (1) not substituted; or (2) substituted by up to that particular number of non-hydrogen substituents or by up to the maximum number of substitutable positions on the substituent, whichever is less. Thus, for example, if a substituent is described as a heteroaryl optionally substituted with up to 3 non-hydrogen substituents, then any heteroaryl with less than 3 substitutable positions would be optionally substituted by up to only as many non-hydrogen substituents as the heteroaryl has substitutable positions. Such substituents, in non-limiting examples, can be selected from a linear, branched or cyclic alkyl, alkenyl or alkynyl having from 1 to 10 carbon atoms, aryl, heteroaryl, heterocycyclyl, halogen, guanidinium [—NH(C=NH)NH$_2$], —OR$^{100}$, NR$^{101}$R$^{102}$, —NO$_2$, —NR$^{101}$COR$^{102}$, —SR$^{100}$, a sulfoxide represented by —SOR$^{101}$, a sulfone represented by —SO$_2$R$^{101}$, a sulfonate —SO$_3$M, a sulfate —OSO$_3$M, a sulfonamide represented by —SO$_2$NR$^{101}$R$^{102}$, cyano, an azido, —COR$^{101}$, —OCOR$^{101}$, —OCONR$^{101}$R$^{102}$ and a polyethylene glycol unit (—OCH$_2$CH$_2$)$_n$R$^{101}$ wherein M is H or a cation (such as Na$^+$ or K$^+$); R$^{101}$, R$^{102}$, and R$^{103}$ are each independently selected from H, linear, branched or cyclic alkyl, alkenyl or alkynyl having from 1 to 10 carbon atoms, a polyethylene glycol unit (—OCH$_2$CH$_2$)$_n$—R$^{104}$, wherein n is an integer from 1 to 24, an aryl having from 6 to 10 carbon atoms, a heterocyclic ring having from 3 to 10 carbon atoms and a heteroaryl having 5 to 10 carbon atoms; and R$^{104}$ is H or a linear or branched alkyl having 1 to 4 carbon atoms, wherein the alkyl, alkenyl, alkynyl, aryl, heteroaryl and heterocyclyl in the groups represented by R$^{100}$, R$^{101}$, R$^{102}$, R$^{103}$ and R$^{104}$ are optionally substituted with one or more (e.g., 2, 3, 4, 5, 6 or more) substituents independently selected from halogen, —OH, —CN, —NO$_2$ and unsubstituted linear or branched alkyl having 1 to 4 carbon atoms. Preferably, the substituents for the optionally substituted alkyl, alkenyl, alkynyl, cyclic alkyl, cyclic alkenyl, cyclic alkynyl, carbocyclyl, aryl, heterocyclyl and heteroaryl described above include halogen, —CN, —NR$^{102}$R$^{103}$, —CF$_3$, —OR$^{101}$, aryl, heteroaryl, heterocycycl, —SR$^{101}$, —SOR$^{101}$, —SO$_2$R$^{101}$ and —SO$_3$M.

The number of carbon atoms in a group can be specified herein by the prefix "C$_{x-xx}$" or "C$_x$-C$_{xx}$", wherein x and xx are integers. For example, "C$_{1-4}$alkyl" or "C1-C4 alkyl" is an alkyl group having from 1 to 4 carbon atoms.

The term "compound" or "cytotoxic compound," "cytotoxic dimer" and "cytotoxic dimer compound" are used interchangeably. They are intended to include compounds for which a structure or formula or any derivative thereof has been disclosed in the present invention or a structure or formula or any derivative thereof that has been incorporated by reference. The term also includes, stereoisomers, geometric isomers, tautomers, solvates, metabolites, salts (e.g., pharmaceutically acceptable salts) and prodrugs, and prodrug salts of a compound of all the formulae disclosed in the present invention. The term also includes any solvates, hydrates, and polymorphs of any of the foregoing. The specific recitation of "stereoisomers," "geometric isomers," "tautomers," "solvates," "metabolites," "salt" "prodrug," "prodrug salt," "conjugates," "conjugates salt," "solvate," "hydrate," or "polymorph" in certain aspects of the invention described in this application shall not be interpreted as an intended omission of these forms in other aspects of the invention where the term "compound" is used without recitation of these other forms.

The term "conjugate" as used herein refers to a compound described herein or a derivative thereof that is linked to a cell binding agent.

The term "linkable to a cell binding agent" as used herein refers to the compounds described herein or derivatives thereof comprising at least one linking group or a precursor thereof suitable to bond these compounds or derivatives thereof to a cell binding agent.

The term "precursor" of a given group refers to any group that can lead to that group by any deprotection, a chemical modification, or a coupling reaction.

The term "chiral" refers to molecules that have the property of non-superimposability of the mirror image partner, while the term "achiral" refers to molecules that are superimposable on their mirror image partner.

The term "stereoisomer" refers to compounds that have identical chemical constitution and connectivity, but different orientations of their atoms in space that cannot be interconverted by rotation about single bonds.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as crystallization, electrophoresis and chromatography.

"Enantiomers" refer to two stereoisomers of a compound that are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds," John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies that are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As used herein, a "benzodiazepine" compound is a compound having a benzodiazepine core structure. The benzodiazepine core can be substituted or unsubstituted, and/or fused with one or more ring structures. It also includes a compound having two benzodiazepine core linked by a linker. The imine functionality (—C=N—) as part of benzodiazepine core can be reduced.

As used herein, a "pyrrolobenzodiazepine" (PBD) compound is a compound having a pyrrolobenzodiazepine core structure. The pyrrolobenzodiazepine can be substituted or unsubstituted. It also includes a compound having two pyrrolobenzodiazepine core linked by a linker. The imine functionality (—C=N—) as part of indolinobenzodiazepine core can be reduced.

In certain embodiments, the pyrrolobenzodiazepine compound comprises a core structure represented by

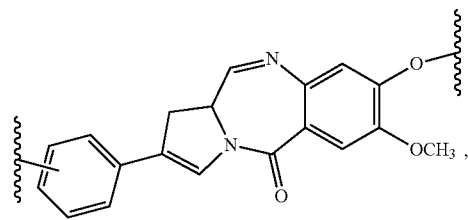

which can be optionally substituted.

In certain embodiments, the pyrrolobenzodiazepine compounds comprises a core structure represented by

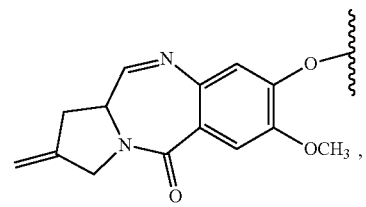 [SMILES: *Oc1cc2c(cc1OC)C(=O)N1CC(=C)CC1C=N2]

which can be optionally substituted.

As used herein, a "indolinobenzodiazepine" (IGN) compound is a compound having an indolinobenzodiazepine core structure. The indolinobenzodiazepine can be substituted or unsubstituted. It also includes a compound having two indolinobenzodiazepine core linked by a linker. The imine functionality (—C=N—) as part of indolinobenzodiazepine core can be reduced.

In certain embodiments, the indolinobenzodiazepine compound comprises a core structure represented by

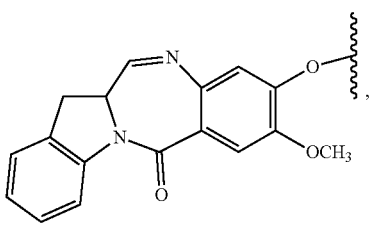 [SMILES: *Oc1cc2c(cc1OC)C(=O)N1c3ccccc3CC1C=N2]

which can be optionally substituted.

In some embodiments, the indolinobenzodiazepine compound comprises a core structure represented by

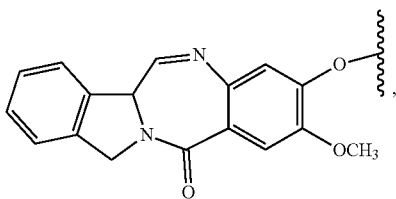 [SMILES: *Oc1cc2c(cc1OC)C(=O)N1Cc3ccccc3C1C=N2]

which can be further substituted.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt can involve the inclusion of another molecule such as an acetate ion, a succinate ion or other counter ion. The counter ion can be any organic or inorganic moiety that stabilizes the charge on the parent compound. Furthermore, a pharmaceutically acceptable salt can have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt can be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt can be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

As used herein, the term "solvate" means a compound that further includes a stoichiometric or non-stoichiometric amount of solvent such as water, isopropanol, acetone, ethanol, methanol, DMSO, ethyl acetate, acetic acid, and ethanolamine dichloromethane, 2-propanol, or the like, bound by non-covalent intermolecular forces. Solvates or hydrates of the compounds are readily prepared by addition of at least one molar equivalent of a hydroxylic solvent such as methanol, ethanol, 1-propanol, 2-propanol or water to the compound to result in solvation or hydration of the imine moiety.

The phrase "pharmaceutically acceptable" indicates that the substance or composition must be compatible chemically and/or toxicologically, with the other ingredients comprising a formulation, and/or the mammal being treated therewith.

The term "protecting group" or "protecting moiety" refers to a substituent that is commonly employed to block or protect a particular functionality while reacting other functional groups on the compound, a derivative thereof, or a conjugate thereof. For example, an "amine-protecting group" or an "amino-protecting moiety" is a substituent attached to an amino group that blocks or protects the amino functionality in the compound. Such groups are well known in the art (see for example P. Wuts and T. Greene, 2007, Protective Groups in Organic Synthesis, Chapter 7, J. Wiley & Sons, NJ) and exemplified by carbamates such as methyl and ethyl carbamate, FMOC, substituted ethyl carbamates, carbamates cleaved by 1,643-elimination (also termed "self immolative"), ureas, amides, peptides, alkyl and aryl derivatives. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). For a general description of protecting groups and their use, see P.G.M. Wuts & T.W. Greene, Protective Groups in Organic Synthesis, John Wiley & Sons, New York, 2007.

The term "leaving group" refers to an group of charged or uncharged moiety that departs during a substitution or displacement. Such leaving groups are well known in the art and include, but not limited to, halogens, esters, alkoxy, hydroxyl, tosylates, triflates, mesylates, nitriles, azide, carbamate, disulfides, thioesters, thioethers and diazonium compounds.

The term "bifunctional crosslinking agent," "bifunctional linker" or "crosslinking agents" refers to modifying agents that possess two reactive groups; one of which is capable of reacting with a cell binding agent while the other one reacts with the cytotoxic compound to link the two moieties together. Such bifunctional crosslinkers are well known in the art (see, for example, Isalm and Dent in *Bioconjugation* chapter 5, p218-363, Groves Dictionaries Inc. New York, 1999). For example, bifunctional crosslinking agents that enable linkage via a thioether bond include N-succinimidyl-4-(N-maleimidomethyl)-cyclohexane-1-carboxylate (SMCC) to introduce maleimido groups, or with N-succinimidyl-4-(iodoacetyl)-aminobenzoate (SIAB) to introduce iodoacetyl groups. Other bifunctional crosslinking agents that introduce maleimido groups or haloacetyl groups on to a cell binding agent are well known in the art (see US Patent Applications 2008/0050310, 20050169933, available from Pierce Biotechnology Inc. P.O. Box 117, Rockland, Ill. 61105, USA) and include, but not limited to, bis-maleimidopolyethyleneglycol (BMPEO), BM(PEO)$_2$, BM(PEO)$_3$, N-(β-maleimidopropyloxy)succinimide ester (BMPS), γ-maleimidobutyric acid N-succinimidyl ester (GMBS), ε-maleimidocaproic acid N-hydroxysuccinimide ester (EMCS), 5-maleimidovaleric acid NHS, HBVS, N-succinimidyl-4-(N-maleimidomethyl)-cyclohexane-1-carboxy-(6-amidocaproate), which is a "long chain" analog of SMCC (LC-SMCC), m-maleimidobenzoyl-N-hydroxysuccinimide ester (MBS), 4-(4-N-maleimidophenyl)-butyric acid hydrazide or HCl salt (MPBH), N-succinimidyl 3-(bromoacetamido)propionate (SBAP), N-succinimidyl iodoacetate (SIA), κ-maleimidoundecanoic acid N-succinimidyl ester (KMUA), N-succinimidyl 4-(p-maleimidophenyl)-butyrate (SMPB), succinimidyl-6-(β-maleimidopropionamido) hexanoate (SMPH), succinimidyl-(4-vinylsulfonyl)benzoate (SVSB), dithiobis-maleimidoethane (DTME), 1,4-bis-maleimidobutane (BMB), 1,4 bismaleimidyl-2,3-dihydroxybutane (BMDB), bis-maleimidohexane (BMH), bis-maleimidoethane (BMOE), sulfosuccinimidyl 4-(N-maleimidomethyl)cyclohexane-1-carboxylate (sulfo-SMCC), sulfosuccinimidyl(4-iodo-acetyl)aminobenzoate (sulfo-SIAB), m-maleimidobenzoyl-N-hydroxysulfosuccinimide ester (sulfo-MBS), N-(γ-maleimidobutryloxy)sulfosuccinimde ester (sulfo-GMBS), N-(ε-maleimidocaproyloxy)sulfosuccimido ester (sulfo-EMCS), N-(κ-maleimidoundecanoyloxy)sulfosuccinimide ester (sulfo-KMUS), and sulfosuccinimidyl 4-(p-maleimidophenyl)butyrate (sulfo-SMPB).

Heterobifunctional crosslinking agents are bifunctional crosslinking agents having two different reactive groups. Heterobifunctional crosslinking agents containing both an amine-reactive N-hydroxysuccinimide group (NHS group) and a carbonyl-reactive hydrazine group can also be used to link the cytotoxic compounds described herein with a cell-binding agent (e.g., antibody). Examples of such commercially available heterobifunctional crosslinking agents include succinimidyl 6-hydrazinonicotinamide acetone hydrazone (SANH), succinimidyl 4-hydrazidoterephthalate hydrochloride (SHTH) and succinimidyl hydrazinium nicotinate hydrochloride (SHNH). Conjugates bearing an acid-labile linkage can also be prepared using a hydrazine-bearing benzodiazepine derivative of the present invention. Examples of bifunctional crosslinking agents that can be used include succinimidyl-p-formyl benzoate (SFB) and succinimidyl-p-formylphenoxyacetate (SFPA).

Bifunctional crosslinking agents that enable the linkage of cell binding agent with cytotoxic compounds via disulfide bonds are known in the art and include N-succinimidyl-3-(2-pyridyldithio)propionate (SPDP), N-succinimidyl-4-(2-pyridyldithio)pentanoate (SPP), N-succinimidyl-4-(2-pyridyldithio)butanoate (SPDB), N-succinimidyl-4-(2-pyridyldithio)2-sulfo butanoate (sulfo-SPDB) to introduce dithiopyridyl groups. Other bifunctional crosslinking agents that can be used to introduce disulfide groups are known in the art and are disclosed in U.S. Pat. Nos. 6,913,748, 6,716,821 and US Patent Publications 20090274713 and 20100129314, all of which are incorporated herein by reference. Alternatively, crosslinking agents such as 2-iminothiolane, homocysteine thiolactone or S-acetylsuccinic anhydride that introduce thiol groups can also be used.

A "linker," "linker moiety," or "linking group" as defined herein refers to a moiety that connects two groups, such as a cell binding agent and a cytotoxic compound, together. Typically, the linker is substantially inert under conditions for which the two groups it is connecting are linked. A bifunctional crosslinking agent can comprise two reactive groups, one at each ends of a linker moiety, such that one reactive group can be first reacted with the cytotoxic compound to provide a compound bearing the linker moiety and a second reactive group, which can then react with a cell binding agent. Alternatively, one end of the bifunctional crosslinking agent can be first reacted with the cell binding agent to provide a cell binding agent bearing a linker moiety and a second reactive group, which can then react with a cytotoxic compound. The linking moiety can contain a chemical bond that allows for the release of the cytotoxic moiety at a particular site. Suitable chemical bonds are well known in the art and include disulfide bonds, thioether bonds, acid labile bonds, photolabile bonds, peptidase labile bonds and esterase labile bonds (see for example U.S. Pat. Nos. 5,208,020; 5,475,092; 6,441,163; 6,716,821; 6,913,748; 7,276,497; 7,276,499; 7,368,565; 7,388,026 and 7,414,073). Preferred are disulfide bonds, thioether and peptidase labile bonds. Other linkers that can be used in the present invention include non-cleavable linkers, such as those described in are described in detail in U.S. publication number 20050169933, or charged linkers or hydrophilic linkers and are described in US 2009/0274713, US 2010/01293140 and WO 2009/134976, each of which is expressly incorporated herein by reference, each of which is expressly incorporated herein by reference.

The term "amino acid" refers to naturally occurring amino acids or non-naturally occurring amino acid. In some embodiments, the amino acid is represented by NH$_2$—C(R$^{aa}$R$^{aa}$)—C(=O)OH, wherein R$^{aa}$ and R$^{aa'}$ are each independently H, an optionally substituted linear, branched or cyclic alkyl, alkenyl or alkynyl having 1 to 10 carbon atoms, aryl, heteroaryl or heterocyclyl or R$^{aa}$ and the N-terminal nitrogen atom can together form a heteroycyclic ring (e.g., as in proline). The term "amino acid residue" refers to the corresponding residue when one hydrogen atom is removed from the amine and/or carboxy end of the amino acid, such as —NH—C(R$^{aa'}$R$^{aa}$)—C(=O)O—.

The term "peptide" refers to short chains of amino acid monomers linked by peptide (amide) bonds. In some embodiments, the peptides contain 2 to 20 amino acid residues. In other embodiments, the peptides contain 2 to 10 amino acid residues. In yet other embodiments, the peptides contain 2 to 5 amino acid residues. As used herein, when a peptide is a portion of a cytotoxic agent or a linker described herein represented by a specific sequence of amino acids, the peptide can be connected to the rest of the cytotoxic agent or the linker in both directions. For example, a dipeptide $X_1$-$X_2$ includes $X_1$-$X_2$ and $X_2$-$X_1$. Similarly, a tripeptide $X_1$-$X_2$-$X_3$ includes $X_1$-$X_2$-$X_3$ and $X_3$—$X_2$-$X_1$ and a tetrapeptide $X_1$-$X_2$-$X_3$-$X_4$ includes $X_1$-$X_2$-$X_3$-$X_4$ and $X_4$-$X_2$-$X_3$-$X_1$. $X_1$, $X_2$, $X_3$ and $X_4$ represents an amino acid residue.

The term "cation" refers to an ion with positive charge. The cation can be monovalent (e.g., Na$^+$, K$^+$, etc.), bi-valent (e.g., Ca$^{2+}$, Mg$^{2+}$, etc.) or multi-valent (e.g., Al$^{3+}$ etc.). Preferably, the cation is monovalent.

The term "cysteine engineered antibody" includes an antibody with at least one cysteine (Cys) that is not normally present at a given residue of the antibody light chain or heavy chain. Such Cys, which may also be referred to as "engineered Cys," can be introduced, for example, by standard recombinant technology (e.g., by replacing the coding sequence for a non-Cys residue at the target residue with a coding sequence for Cys). In certain embodiments, the Cys engineered antibody of the invention has an engineered Cys in the heavy chain. In certain embodiments, the engineered Cys is in or near the CH3 domain of the heavy chain. In certain embodiments, the engineered Cys is at residue 442 of the heavy chain (EU/OU numbering).

As used herein, all antibody amino acid residues described herein are numbered according to the EU index, Kabat et al., *Sequences of Proteins of Immunological Interest*, 5th Ed., NIH publication No. 91-3242, 1991 (EU/OU numbering, entire content incorporated herein by reference). The common isotypes are referred to as G1, G2, G4, etc.

The C442 residue can be conjugated with a cytotoxic drug/agent through the free thiol group of the C442 residue, such as through reacting with a thiol-reactive agent of the cytotoxic drug (e.g., a maleimido group).

As used herein, an "aqueous solution" refers to a solution in which the solvent is water or a mixture of water and one or more organic solvents.

As used herein, the term "treating" or "treatment" includes reversing, reducing, or arresting the symptoms, clinical signs, and underlying pathology of a condition in manner to improve or stabilize a subject's condition. As used herein, and as well understood in the art "treatment" is an approach for obtaining beneficial or desired results, including clinical results. Beneficial or desired clinical results can include, but are not limited to, alleviation, amelioration, or slowing the progression, of one or more symptoms or conditions associated with a condition, e.g., cancer, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Exemplary beneficial clinical results are described herein.

METHODS OF THE PRESENT INVENTION

The present invention provides novel methods for preparing a cell-binding agent-cytotoxic agent conjugate comprising an imine-containing cytotoxic agent bearing a maleimide group covalently linked to a cell-binding agent (CBA).

In some embodiments, the methods of the present invention for preparing a cell-binding agent-cytotoxic agent conjugate comprise the steps of:

(a) reacting an imine-moiety in an imine-containing cytotoxic agent represented by the following formula:

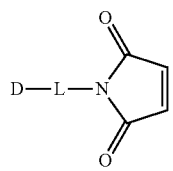

(A)

or a pharmaceutically acceptable salt thereof, with sulfur dioxide, a bisulfite salt or a metabisulfite salt in an aqueous solution at a pH of 1.9 to 5.0 to form a modified cytotoxic agent comprising a modified imine moiety represented by the following formula:

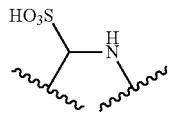

or a pharmaceutically acceptable salt thereof; and (b) reacting the modified cytotoxic agent with a cell-binding agent to form the cell-binding agent-cytotoxic agent conjugate. In some embodiments, the bisulfite salt is sodium bisulfite or potassium bisulfite. More specifically, the bisulfite salt is sodium bisulfite. In yet other embodiments, the metabisulfite salt is sodium metabisulfite or potassium metabisulfite. More specifically, the metabisulfite salt is sodium metabisulfite.

The present invention also provides a method of preparing a modified cytotoxic agent comprising the step of reacting an imine-moiety in an imine-containing cytotoxic agent represented by the following formula:

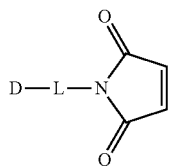

(A)

or a pharmaceutically acceptable salt thereof, with sulfur dioxide, a bisulfite salt or a metabisulfite salt in an aqueous solution at a pH of 1.9 to 5.0 to form a modified cytotoxic agent comprising a modified imine moiety represented by the following formula:

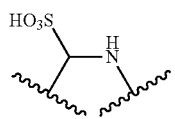

or a pharmaceutically acceptable salt thereof. In some embodiments, the reaction can be carried out under the reaction conditions described in the 1st, 2nd, 3rd, 4th, 5th, 6th or 7th aspect below.

In a 1st aspect, for the method of the present invention described above, the reaction of step (a) is carried out at a pH of 1.9 to 5.0. More specifically, the pH is 2.5 to 4.9, 1.9 to 4.8, 2.0 to 4.8, 2.5 to 4.5, 2.9 to 4.5, 2.9 to 4.0, 2.9 to 3.7, 3.1 to 3.5, or 3.2 to 3.4. In another specific embodiment, the reaction of step (a) is carried out at a pH of 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.5, 4.6, 4.7, 4.8, 4.9 or 5.0. In yet another specific embodiment, the reaction of step (a) is carried out at a pH of 3.3.

As used herein, a specific pH value means the specific value±0.05.

In some embodiments, the reaction of step (a) is carried out in the presence of a buffer solution. Any suitable buffer solution known in the art can be used in the methods of the present invention. Suitable buffer solutions include, for example, but are not limited to, a citrate buffer, an acetate buffer, a succinate buffer, a phosphate buffer, a glycine-containing buffer (e.g., glycine-HCl buffer), a phthalate buffer (e.g., a buffer solution comprising sodium or potassium hydrogen phthalate), and a combination thereof. In some embodiments, the buffer solution is a succinate buffer. In some embodiments, the buffer solution is a phosphate buffer. In some embodiments, the buffer is a citrate-phosphate buffer. In some embodiments, the buffer is a citrate-phosphate buffer comprising citric acid and $Na_2HPO_4$. In other embodiments, the buffer is a citrate-phosphate buffer comprising citric acid and $K_2HPO_4$. In some embodiments, the concentration of the buffer solution described above can be in the range of 10 to 250 mM, 10 to 200 mM, 10 to 150 mM, 10 to 100 mM, 25 to 100 mM, 25 to 75 mM, 10 to 50 mM, or 20 to 50 mM.

In a $2^{nd}$ aspect, the reaction step (a) is carried out in the absence of a buffer solution (e.g., the buffers described in the $1^{st}$ aspect). In some embodiments, the present method comprises the steps of: (a) reacting an imine-moiety in an imine-containing cytotoxic agent represented by formula (A) or a pharmaceutically acceptable salt thereof, with sulfur dioxide, a bisulfite salt or a metabisulfite salt in an aqueous solution to form a modified cytotoxic agent comprising a modified imine moiety represented by the following formula:

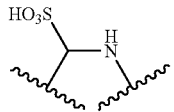

or a pharmaceutically acceptable salt thereof, wherein the aqueous solution does not comprise a buffer; and (b) reacting the modified cytotoxic agent with a cell-binding agent to form the cell-binding agent-cytotoxic agent conjugate. In some embodiments, the reaction of step (a) is carried out in a mixture of an organic solvent and water. More specifically, the reaction of step (a) is carried out in a mixture of dimethyacetamide (DMA) and water. In some embodiments, the mixture of DMA and water comprises less than 60% of DMA by volume. Even more specifically, the volume ratio of DMA and water is 1:1.

In a $3^{rd}$ aspect, for the methods described above or in the $1^{st}$ or $2^{nd}$ aspect, 0.5 to 5.0 equivalents of the bisulfite salt or 0.25 or 2.5 equivalents of the metabisulfite salt is used for every 1 equivalent of the imine-containing cytotoxic agent in the reaction of step (a). In some embodiments, 0.5 to 4.5, 0.5 to 4.0, 0.5 to 3.5, 0.5 to 4.0, 0.5 to 3.5, 0.5 to 3.0, 0.5 to 2.5, 0.8 to 2.0, 0.9 to 1.8, 1.0 to 1.7, 1.1 to 1.6, or 1.2 to 1.5 equivalents of the bisulfite salt or 0.25 to 2.25, 0.25 to 2.0, 0.25 to 1.75, 0.25 to 2.0, 0.25 to 1.75, 0.25 to 1.5, 0.25 to 1.25, 0.4 to 1.0, 0.45 to 0.9, 0.5 to 0.85, 0.55 to 0.8, or 0.6 to 0.75 equivalents of the metabisulfite salt is used for every 1 equivalent of the imine-containing cytotoxic agent. In other embodiments, 0.5, 0.6, 0.7, 0.8, 0.9, 1.0, 1.1, 1.2, 1.3 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 4.0, 4.5 or 5.0 equivalents of the bisulfite salt or 0.25, 0.3, 0.35, 0.4, 0.45, 0.5, 0.55, 0.6, 0.65 0.7, 0.75, 0.8, 0.85, 0.9, 0.95, 1.0, 1.05, 1.1, 1.15, 1.2, 1.25, 1.3, 1.35, 1.4, 1.45, 1.5, 1.55, 1.6, 1.65, 1.7, 1.75, 2.0, 2.25 or 2.5 equivalents of the metabisulfite salt is used for every 1 equivalent of the imine-containing cytotoxic agent. In yet other embodiments, 1.4 equivalents of the bisulfite salt or 0.7 equivalent of the metabisulfite salt is used for every 1 equivalent of the imine-containing cytotoxic agent. In other embodiments, 1.2 equivalents of the bisulfite salt or 0.6 equivalent of the metabisulfite salt is used for every 1 equivalent of the imine-containing cytotoxic agent.

As used herein, a specific equivalent means the specific value±0.05.

In a $4^{th}$ aspect, for methods of the present invention, the reaction of step (a) is carried out at a pH of 2.9 to 3.7 and 1.0 to 1.8 equivalents of the bisulfite salt or 0.5 to 0.9 equivalents of the metabisulfite salt is reacted with 1 equivalent of the imine-containing cytotoxic agent. In some embodiments, the reaction of step (a) is carried out at a pH of 3.1 to 3.5 and 1.1 to 1.6 equivalents of the bisulfite salt or 0.55 to 0.8 equivalents of the metabisulfite salt is reacted with 1 equivalent of the imine-containing cytotoxic agent. In other embodiments, the reaction of step (a) is carried out at a pH of 3.2 to 3.4 and 1.3 to 1.5 equivalents of the bisulfite salt or 0.65 to 0.75 equivalents of the metabisulfite is reacted with 1 equivalent of the imine-containing cytotoxic agent. In other embodiments, the reaction of step (a) is carried out at a pH of 3.3 and 1.4 equivalents of the bisulfite salt or 0.7 equivalent of the metabisulfite salt is reacted with 1 equivalent of the imine-containing cytotoxic agent. In yet other embodiments, In other embodiments, the reaction of step (a) is carried out at a pH of 3.3 and 1.4 equivalents of sodium bisulfite is reacted with 1 equivalent of the imine-containing cytotoxic agent.

In a $5^{th}$ aspect, for the methods of the present invention described herein or in the $1^{st}$, $2^{nd}$, $3^{rd}$ or $4^{th}$ aspect, the reaction of step (a) is carried out in a mixture of an organic solvent and water. Any suitable organic solvent can be used. Exemplary organic solvents include, but are not limited to, alcohols (e.g., methanol, ethanol, propanol, etc.), dimethylformamide (DMF), dimethylsulfoxide (DMSO), acetonitrile, acetone, methylene chloride, etc. In some embodiments, the organic solvent is miscible with water. In other embodiments, the organic solvent is not miscible with water, i.e., the reaction of step (a) is carried out in a biphasic solution. In some embodiments, the organic solvent is dimethylacetamide (DMA). The organic solvent (e.g., DMA) can be present in the amount of 1%-99%, 1-95%, 10-80%, 20-70%, 30-70%, 1-60%, 5-60%, 10-60%, 20-60%, 30-60%, 40-60%, 45-55%, 10-50%, or 20-40%, by volume of the total volume of water and the organic solvent. In some embodiments, the reaction of step (a) is carried out in a mixture of DMA and water, wherein the volume ratio of DMA and water is 1:1.

In a $6^{th}$ aspect, for the methods of the present invention described herein or in the $1^{st}$, $2^{nd}$, $3^{rd}$, $4^{th}$ or $5^{th}$ aspect, the reaction of step (a) can be carried out at any suitable temperature. In some embodiments, the reaction is carried out at a temperature from 0° C. to 50° C., from 10° C. to 50° C., from 10° C. to 40° C., or from 10° C. to 30° C. In other embodiments, the reaction is carried out at a temperature from 15° C. to 30° C., from 20° C. to 30° C., from 15° C. to 25° C., from 16° C. to 24° C., from 17° C. to 23° C., from 18° C. to 22° C. or from 19° C. to 21° C. In yet other embodiments, the reaction can be carried out at 15° C., 16° C., 17° C., 18° C., 19° C., 20° C., 21° C., 22° C., 23° C., 24° C. or 25° C. In some embodiments, the reaction can be carried out from 0° C. to 15° C., from 0° C. to 10° C., from 1° C. to 10° C., 5° C. to 15° C., or from 5° C. to 10° C.

In a $7^{th}$ aspect, for the methods of the present invention described herein or in the $1^{st}$, $2^{nd}$, $3^{rd}$, $4^{th}$, $5^{th}$ or $6^{th}$ aspect, the reaction of step (a) is carried out for 1 minute to 48 hours, 5 minutes to 36 hours, 10 minutes to 24 hours, 30 minutes to 24 hours, 30 minutes to 20 hours, 1 hour to 20 hours, 1 hour to 15 hours, 1 hour to 10 hours, 2 hours to 10 hours, 3 hours to 9 hours, 3 hours to 8 hours, 4 hours to 6 hours, or 1 hour to 4 hours. In some embodiments, the reaction is allowed to proceed for 4 to 6 hours. In other embodiments, the reaction is allowed to proceed for 10 minutes, 15 minutes, 20 minutes, 30 minutes, 1 hours, 2 hours, 3 hours, 4 hours, 5 hours, 6 hours, 7 hours, 8 hours, 9 hours, 10 hours, 11 hours, 12 hours, 13 hours, 14 hours, 15 hours, etc. In other embodiments, the reaction is allowed to proceed for 4 hours. In yet other embodiments, the reaction is allowed to proceed for 2 hours.

In a $8^{th}$ aspect, for the methods of the present invention described herein or in the $1^{st}$, $2^{nd}$, $3^{rd}$, $4^{th}$, $5^{th}$, $6^{th}$ or $7^{th}$ aspect, the reaction of step (b) is carried out at a pH of 4 to 9. In some embodiments, the reaction of step (b) is carried out at a pH of 4.5 to 8.5, 5 to 8.5, 5 to 8, 5 to 7.5, 5 to 7, 5 to 6.5, or 5.5 to 6.5. In other embodiments, the reaction of step (b) is carried out at pH 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or 8.0.

In some embodiments, for the methods of the present invention described herein or in the $1^{st}$, $2^{nd}$, $3^{rd}$, $4^{th}$, $5^{th}$, $6^{th}$, $7^{th}$ or $8^{th}$ aspect, the reaction of step (b) is carried out in an aqueous solution comprising a mixture of water and an organic solvent. Any suitable organic solvent described above can be used. More specifically, the organic solvent is DMA. In some embodiments, the aqueous solution comprises less than 50%, less than 40%, less than 30%, less than 25%, less than 20%, less than 15%, less than 10%, less than 5%, less than 3%, less than 2%, or less than 1% of the organic solvent (e.g. DMA) by volume.

In some embodiments, for the methods of the present invention described herein or in the $1^{st}$, $2^{nd}$, $3^{rd}$, $4^{th}$, $5^{th}$, $6^{th}$, $7^{th}$ or $8^{th}$ aspect, the modified cytotoxic agent is not purified before reacting with the cell-binding agent in step (b). Alternatively, the modified cytotoxic agent is purified before reacting with the cell-binding agent in step (b). Any suitable methods described herein can be used to purify the modified cytotoxic agent. In certain embodiments, the present invention provides isolated modified cytotoxic agent prepared by the present methods. The isolated modified cytotoxic agent can be stored for a period of time before reacting with the cell-binding agent. Preferably, the isolated modified cytotoxic agent is stored under conditions that will prevent the decomposition of the modified cytotoxic agent, for example, as purified solid or as frozen solution or be kept at a low temperature (e.g., less than 10° C. or less than 5° C.).

In some embodiments, for the methods of the present invention described herein or in any one of the embodiments described above, the cell-binding agent-cytotoxic agent conjugate of step (b) is subject to a purification step. In this regard, the cell-binding agent-cytotoxic agent conjugate can be purified from the other components of the mixture using tangential flow filtration (TFF), non-adsorptive chromatography, adsorptive chromatography, adsorptive filtration, selective precipitation, or any other suitable purification process, as well as combinations thereof.

In some embodiments of the invention, the cell-binding agent-cytotoxic agent conjugate is purified using a single purification step (e.g., TFF). Preferably, the conjugate is purified and exchanged into the appropriate formulation using a single purification step (e.g., TFF). In other embodiments of the invention, the cell-binding agent cytotoxic agent conjugate is purified using two sequential purification steps. For example, the conjugate can be first purified by selective precipitation, adsorptive filtration, absorptive chromatography or non-absorptive chromatography, followed by purification with TFF. One of ordinary skill in the art will appreciate that purification of the cell-binding agent-cytotoxic agent conjugate enables the isolation of a stable conjugate comprising the cell-binding agent chemically coupled to the cytotoxic agent.

Any suitable TFF systems may be utilized for purification, including a Pellicon type system (Millipore, Billerica, Mass.), a Sartocon Cassette system (Sartorius AG, Edgewood, N.Y.), and a Centrasette type system (Pall Corp., East Hills, N.Y.)

Any suitable adsorptive chromatography resin may be utilized for purification. Preferred adsorptive chromatography resins include hydroxyapatite chromatography, hydrophobic charge induction chromatography (HCIC), hydrophobic interaction chromatography (HIC), ion exchange chromatography, mixed mode ion exchange chromatography, immobilized metal affinity chromatography (IMAC), dye ligand chromatography, affinity chromatography, reversed phase chromatography, and combinations thereof. Examples of suitable hydroxyapatite resins include ceramic hydroxyapatite (CHT Type I and Type II, Bio-Rad Laboratories, Hercules, Calif.), HA Ultrogel hydroxyapatite (Pall Corp., East Hills, N.Y.), and ceramic fluoroapatite (CFT Type I and Type II, Bio-Rad Laboratories, Hercules, Calif.). An example of a suitable HCIC resin is MEP Hypercel resin (Pall Corp., East Hills, N.Y.). Examples of suitable HIC resins include Butyl-Sepharose, Hexyl-Sepharose, Phenyl-Sepharose, and Octyl Sepharose resins (all from GE Healthcare, Piscataway, N.J.), as well as Macro-prep Methyl and Macro-Prep t-Butyl resins (Biorad Laboratories, Hercules, Calif.). Examples of suitable ion exchange resins include SP-Sepharose, CM-Sepharose, and Q-Sepharose resins (all from GE Healthcare, Piscataway, N.J.), and Unosphere S resin (Bio-Rad Laboratories, Hercules, Calif.). Examples of suitable mixed mode ion exchangers include Bakerbond ABx resin (JT Baker, Phillipsburg N.J.) Examples of suitable IMAC resins include Chelating Sepharose resin (GE Healthcare, Piscataway, N.J.) and Profinity IMAC resin (Bio-Rad Laboratories, Hercules, Calif.). Examples of suitable dye ligand resins include Blue Sepharose resin (GE Healthcare, Piscataway, N.J.) and Affi-gel Blue resin (Bio-Rad Laboratories, Hercules, Calif.). Examples of suitable affinity resins include Protein A Sepharose resin (e.g., Mab-Select, GE Healthcare, Piscataway, N.J.), where the cell-binding agent is an antibody, and lectin affinity resins, e.g. Lentil Lectin Sepharose resin (GE Healthcare, Piscataway, N.J.), where the cell-binding agent bears appropriate lectin binding sites. Alternatively an antibody specific to the cell-binding agent may be used. Such an antibody can be immobilized to, for instance, Sepharose 4 Fast Flow resin (GE Healthcare, Piscataway, N.J.). Examples of suitable reversed phase resins include C4, C8, and C18 resins (Grace Vydac, Hesperia, Calif.).

Any suitable non-adsorptive chromatography resin may be utilized for purification. Examples of suitable non-adsorptive chromatography resins include, but are not limited to, SEPHADEX™ G-25, G-50, G-100, SEPHACRYL™ resins (e.g., S-200 and S-300), SUPERDEX™ resins (e.g., SUPERDEX™ 75 and SUPERDEX™ 200), BIO-GEL® resins (e.g., P-6, P-10, P-30, P-60, and P-100), and others known to those of ordinary skill in the art.

In some embodiments, the purified cell-binding agent-cytotoxic agent conjugate is formulated into a suitable formulation buffer. In some embodiments, the formulation buffer comprises a bisulfite salt, such as sodium bisulfite or potassium bisulfite. More specifically, the formulation buffer comprises sodium bisulfite. In some embodiments, the formulation buffer comprises 5 to 200 µM, 10 to 200 µM, 10 to 150 µM, 20 to 100 µM, 30 to 90 µM, 40 to 80 µM, 50 to 70 µM, 40 to 60 µM, 45 to 55 µM, or 55 to 65 µM of the bisulfite salt (e.g., sodium bisulfite). In other embodiments, the formulation buffer comprises 20, 30, 40, 45, 46, 47, 48, 49, 50, 51, 52, 53, 54, 55, 56, 57, 58, 59, 60, 61, 62, 63, 64, 65, 70, 80, 90, or 100 μM of the bisulfite salt (e.g., sodium bisulfite).

In other embodiments, the formulation buffer further comprises trehalose. Any suitable amount of trehalose can be used. In some embodiments, the formulation buffer further comprises 2 to 15%, 5 to 10%, 6 to 10% or 7 to 9% or 6 to 8% of trehalose by weight.

In another embodiment, the formulation buffer has a pH of 4 to 6, 4 to 5, or 4 to 4.5. In other embodiments, the pH for the formulation buffer is 4.0, 4.1, 4.2, 4.3, 4.4, 4.5, 4.6, 4.7, 4.8, 4.9, or 5.0.

In yet other embodiments, the formulation buffer comprises 10 mM sodium succinate, 50 μM sodium bisulfite, 8% trelose dihydrate and 0.01% polysorbate 20 at pH 4.2.

In some embodiments, for the methods of the present invention described herein, the reaction of step (a) results in no substantial sulfonation of the maleimide group. In some embodiments, less than 50%, 40%, 30%, 20%, 10%, 9%, 8%, 7%, 6%, 5%, 4%, 3%, 2%, or 1% of the maleimide group is sulfonated. The percentage of maleimide sulfonation is equal to the total amount of the maleimide-sulfonated cytotoxic agent (the cytotoxic agent having sulfonation on the maleimide only) and the di-sulfonated cytotoxic agent (the cytotoxic agent having sulfonation on both the maleimide and the imine moieties) divided by the starting amount of the imine-containing cytotoxic agent before its reaction with the bisulfite salt or the metabisulfite salt.

In a 9$^{th}$ aspect, the present invention provides a method of preparing a cell-binding agent-cytotoxic agent conjugate represented by the following formula:

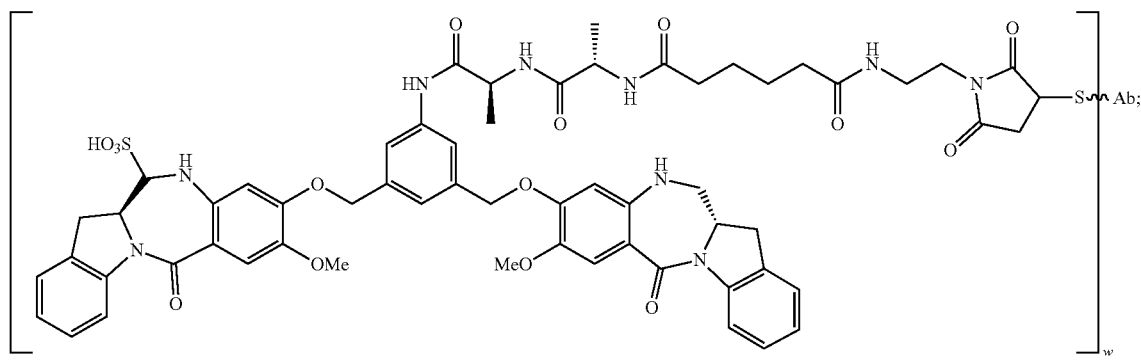

or a pharmaceutically acceptable salt thereof, comprising the steps of:
(a) reacting an imine-moiety in an imine-containing cytotoxic agent represented by the following formula:

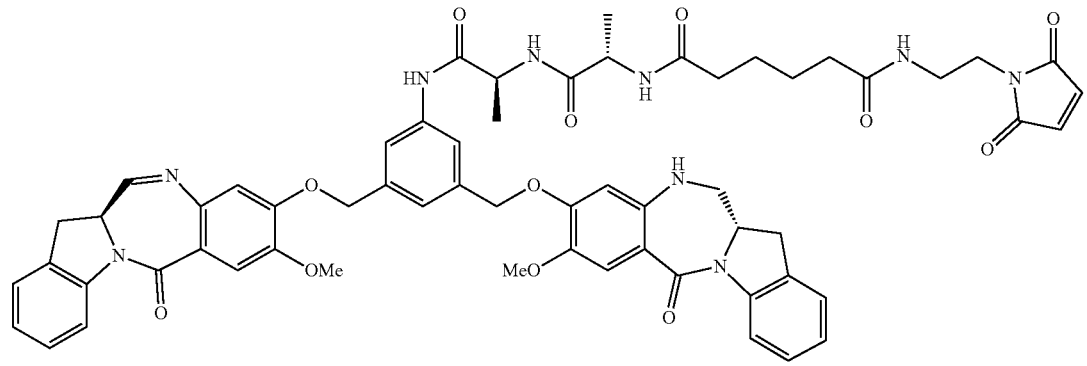 [SMILES: COc1cc2c(cc1OCc1cc(COc3cc4c(cc3OC)C(=O)N3c5ccccc5C[C@H]3CN4)cc(NC(=O)[C@H](C)NC(=O)[C@H](C)NC(=O)CCCCC(=O)NCCN3C(=O)C=CC3=O)c1)N=C[C@@H]1Cc3ccccc3N1C2=O]

or a pharmaceutically acceptable salt thereof, with sulfur dioxide, a bisulfite salt or a metabisulfite salt in an aqueous solution at a pH of 3.1 to 3.5 to form a modified cytotoxic agent represented by the following formula:

than 40%, less than 30%, less than 25%, less than 20%, less than 15%, less than 10%, less than 5%, less than 3%, less than 2%, or less than 1% of the organic solvent (e.g. DMA) by volume.

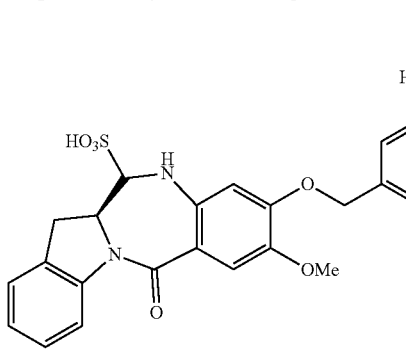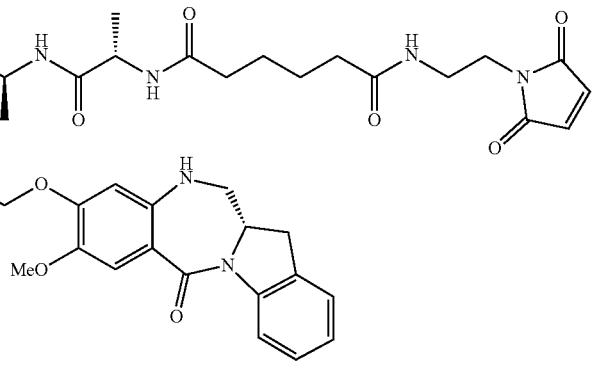

or a pharmaceutically acceptable salt thereof; and (b) reacting the modified cytotoxic agent or a pharmaceutically acceptable salt thereof, with a cell-binding agent Ab to form the cell-binding agent-cytotoxic agent conjugate, wherein:

Ab is an anti-CD123 antibody comprising an immunoglobulin heavy chain having the amino acid sequence of SEQ ID NO:25 and an immunoglobulin light chain having the amino acid sequence of SEQ ID NO:26; and w is 1 or 2.

In some embodiments, the method of the $9^{th}$ aspect is carried out under reaction conditions described in the $1^{st}$, $2^{nd}$, $3^{rd}$, $4^{th}$, $5^{th}$, $6^{th}$, $7^{th}$, or $8^{th}$ aspect and any embodiments described therein.

In a $10^{th}$ aspect, the reaction of step (a) in the method of $9^{th}$ aspect is carried out at a pH of 3.2 to 3.4. More specifically, the pH is 3.3.

In some embodiments, the reaction of step (a) is carried out in the presence of a buffer solution. Exemplary buffer solutions include, but are not limited to, a citrate buffer, an acetate buffer, a succinate buffer or a phosphate buffer. More specifically, the buffer is a succinate buffer.

In a $11^{th}$ aspect, for the reaction of step (a) in the method of $9^{th}$ aspect, 1.1 to 1.6 equivalents of the bisulfite salt or 0.55 to 0.8 equivalents of the metabisulfite salt is reacted with 1 equivalent of the imine-containing cytotoxic agent. The remaining reaction conditions are as described above in the $10^{th}$ aspect and any embodiments described therein. In some embodiments, 1.3 to 1.5 equivalents of the bisulfite salt or 0.65 to 0.75 equivalents of the metabisulfite salt is reacted with 1 equivalent of the imine-containing cytotoxic agent. More specifically, 1.4 equivalents of the bisulfite salt or 0.7 equivalents of the metabisulfite salt is reacted with 1 equivalent of the imine-containing cytotoxic agent.

In a $12^{th}$ aspect, the reaction of step (a) in the method of $9^{th}$ aspect is carried out at a pH of 3.2 to 3.4 and 1.3 to 1.5 equivalents of the sodium bisulfite salt is reacted with 1 equivalent of the imine-containing cytotoxic agent. In some embodiments, the reaction is carried out at a pH of 3.3 and 1.4 equivalents of the sodium bisulfite salt is reacted with 1 equivalent of the imine-containing cytotoxic agent.

In some embodiments, the reaction of step (a) in the method of $9^{th}$, $10^{th}$, $11^{th}$ or $12^{th}$ aspect is carried out in a suitable solvent or solvent mixture. In some embodiments, the reaction of step (a) is carried out in an aqueous solution comprising a mixture of water and an organic solvent. Any suitable organic solvent described above can be used. More specifically, the organic solvent is DMA. In some embodiments, the aqueous solution comprises less than 50%, less In some embodiments, the reaction of step (a) is carried out at a suitable temperature, for example, at room temperature or at 15 to 25° C., for a sufficient period time, such as 1 hour, 2 hours, 3 hours, 4 hours, 5 hours, 6 hours, 7 hours, 8 hours, 9 hours, 10 hours, 12 hours, 15 hours, 20 hours, 24 hours, 48 hours, etc.

In some embodiments, the modified cytotoxic agent obtained from the reaction of step (a) is not purified before reacting with the cell-binding agent in step (b).

In some embodiments, the modified cytotoxic agent obtained from the reaction of step (a) is purified before reacting with the cell-binding agent in step (b). Any suitable purification methods described herein can be used.

In a $13^{th}$ aspect, the reaction of step (b) in the method of $9^{th}$ aspect is carried out at a pH of 5.5 to 6.5; and the remaining reaction conditions are as described in the $9^{th}$, $10^{th}$, $11^{th}$ or $12^{th}$ aspect. In some embodiments, the pH is 5.5, 5.6, 5.7, 5.8, 5.9, 6.0, 6.1, 6.2, 6.3, 6.4 or 6.5. In some embodiments, the pH is 6.0.

In some embodiments, the conjugate prepared by the methods of the $9^{th}$, $10^{th}$, $11^{th}$, $12^{th}$ or $13^{th}$ aspect is purified by a suitable method described herein. In one embodiment, the conjugate is purified by tangential flow filtration to yield purified conjugate.

In some embodiments, the purified conjugate is formulated in a formulation buffer comprising 40 to 80 μM of sodium bisulfite having a pH of 4 to 5. In some embodiments, the formulation buffer comprises 50 μM of sodium bisulfite having a pH of 4.2. In some embodiments, the formulation buffer comprises 10 mM sodium succinate, 50 μM sodium bisulfite, 8% trelose dihydrate and 0.01% polysorbate 20 at pH 4.2.

In some embodiments, for the methods of the present invention described herein (e.g., the $1^{st}$, $2^{nd}$, $3^{rd}$, $4^{th}$, $5^{th}$, $6^{th}$, $7^{th}$ or $8^{th}$ aspect and any embodiments described therein), the cell-binding agent is not an anti-CD123 antibody.

In some embodiments, for methods of the present invention described herein (e.g., the $1^{st}$, $2^{nd}$, $3^{rd}$, $4^{th}$, 4, $5^{th}$, $6^{th}$, $7^{th}$ or $8^{th}$ aspect and any embodiments described therein), the cell-binding agent is not an anti-CD123 antibody comprising an immunoglobulin heavy chain having the amino acid sequence of SEQ ID NO:25 and an immunoglobulin light chain having the amino acid sequence of SEQ ID NO:26.

In some embodiments, the cell-binding agent-cytotoxic agent conjugate prepared by the methods of the present invention described herein (e.g., the $1^{st}$, $2^{nd}$, $3^{rd}$, $4^{th}$, $5^{th}$, $6^{th}$, $7^{th}$ or $8^{th}$ aspect and any embodiments described therein) is not a conjugate represented by the following structure:

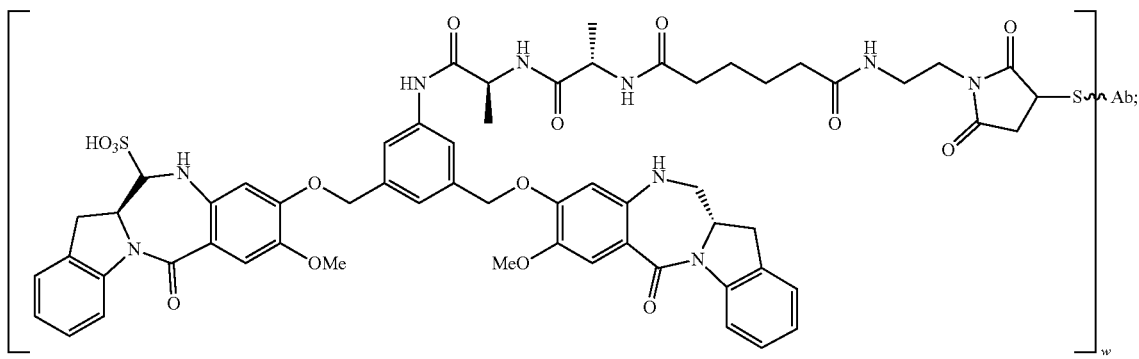

or a pharmaceutically acceptable salt thereof, wherein Ab is an anti-CD123 antibody comprising an immunoglobulin heavy chain having the amino acid sequence of SEQ ID NO:25 and an immunoglobulin light chain having the amino acid sequence of SEQ ID NO:26; and w is 1 or 2.

Imine-Containing Cytotoxic Agents and Conjugates of the Present Invention

In some embodiments, for the methods of the present invention described herein, the imine-containing cytotoxic agent is represented by the following formula:

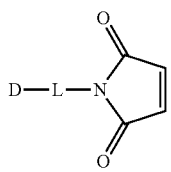
(A)

or a pharmaceutically acceptable salt thereof, and the cell-binding agent-cytotoxic agent conjugate is represented by the following formula:

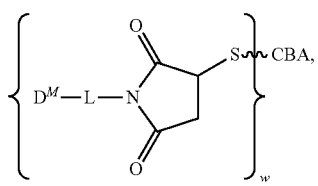
(B)

wherein $D^M$ is the modified cytotoxic agent comprising the modified imine moiety represented by the following formula:

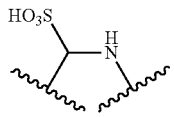

or a pharmaceutically acceptable salt thereof; L is a linker; CBA ~~ S— represents the cell-binding agent linked to the cytotoxic agent via a thiol group; and w is an integer from 1 to 10.

In some embodiments, the CBA is an antibody and the antibody is linked to the cytotoxic agent via one or more cysteine thiol group. In some embodiments, the free thiol group is on an engineered Cys residue in the heavy chain CH3 region of an antibody, at the EU/OU numbering position 442 of that heavy chain (or C442 for short). More specifically, the cysteine residue at position 442 is recombinantly introduced into the antibody.

In other embodiments, w is 1 or 2. More specifically, w is 2.

The following describes certain embodiments and specific embodiments for the methods of the present invention described herein (e.g., the methods of the $1^{st}$, $2^{nd}$, $3^{rd}$, $4^{th}$, $5^{th}$, $6^{th}$, $7^{th}$ or $8^{th}$ aspect described above and embodiments described therein).

In a $1^{st}$ specific aspect, for the imine-containing cytotoxic agent of formula (A) or the conjugate of formula (B), D is represented by the following structural formula:

(IGN1')

-continued
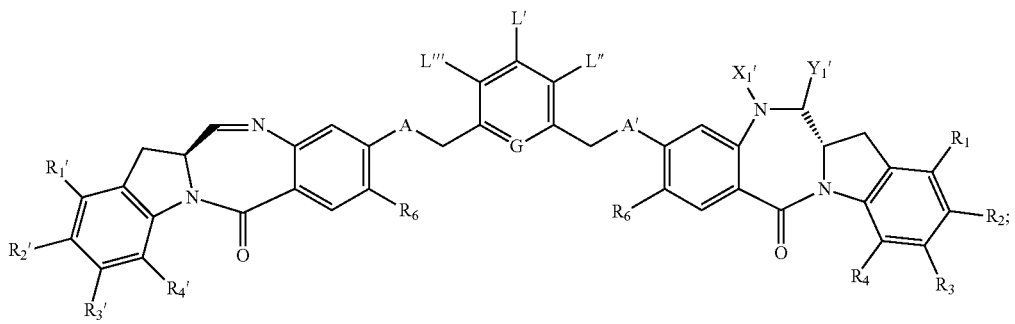
(IGN1)
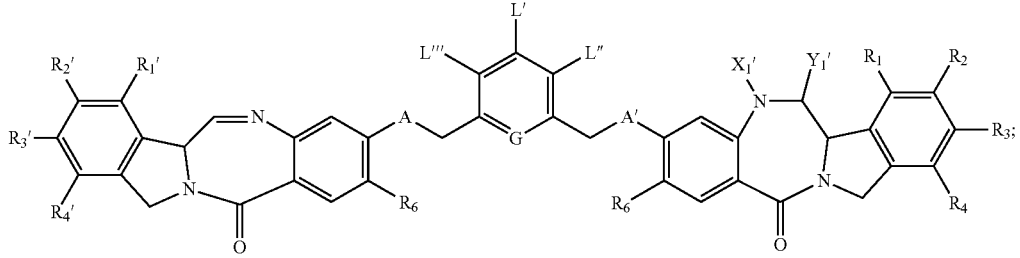
(IGN2')
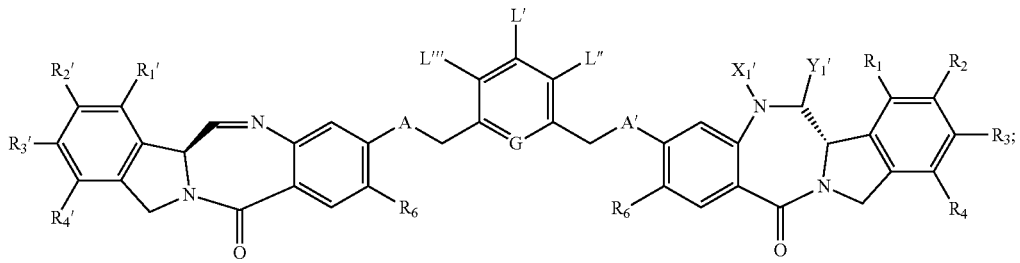
(IGN2)
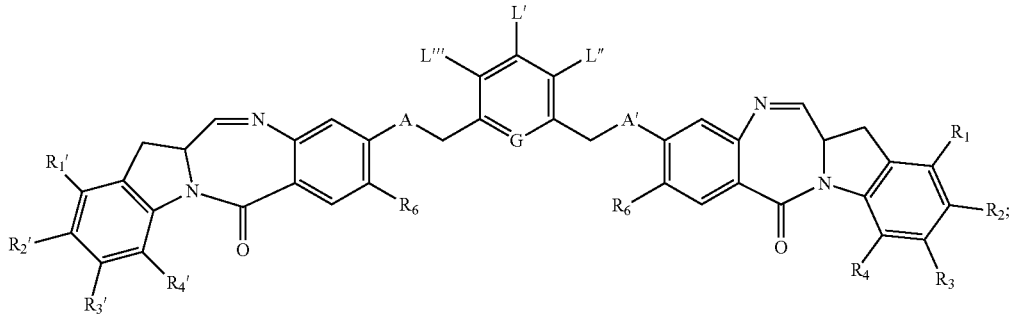
(IGN3')
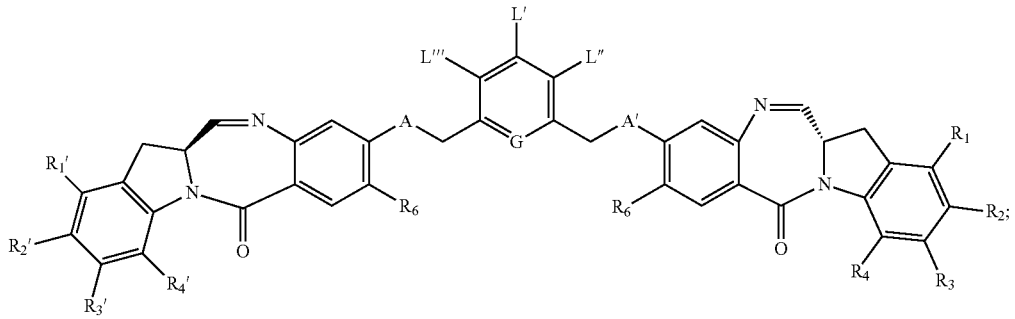
(IGN3)

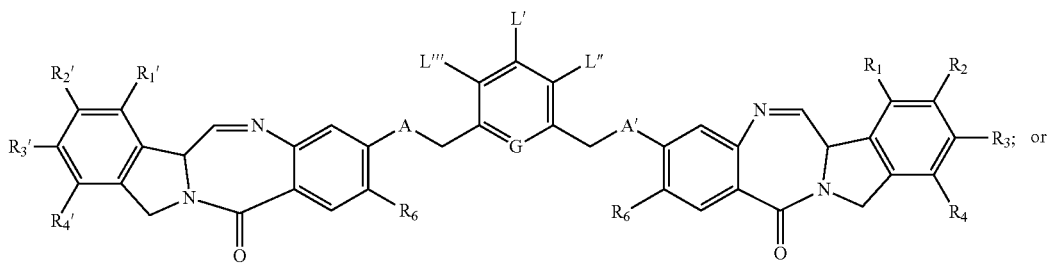

(IGN4')

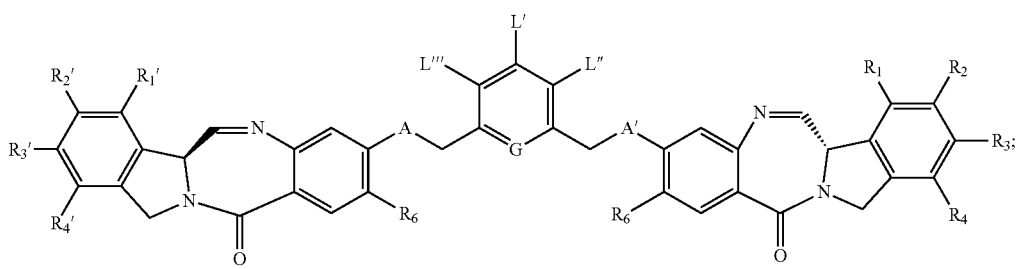

(IGN4)

or a pharmaceutically acceptable salt thereof, wherein:

one of L', L", and L''' is represented by the following formula:

　(A'), or

　(D');

and the other two are each independently selected from —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, halogen, guanidinium [—NH(C=NH)NH$_2$], —OR, —NR'R", —NO$_2$, —NR'COR", —SR, —SOR', —SO$_2$R', —SO$_3$H, —OSO$_3$H, —SO$_2$NR'R", cyano, an azido, —COR', —OCOR', and —OCONR'R";

one of the Z$_1$ and Z$_2$ is —C(=O)—, and the other is —NR$_5$—;

P$_1$ is an amino acid residue or a peptide containing between 2 to 20 amino acid residues; R$_{x1}$ is an optionally substituted linear, branched or cyclic alkyl, alkenyl or alkynyl having from 1 to 10 carbon atoms;

R$^e$ is —H, a linear, branched or cyclic alkyl, alkenyl or alkynyl having 1 to 10 carbon atoms or —(CH$_2$—CH$_2$—O)$_n$—R$^k$, wherein R$^k$ is a —H, a linear, branched cyclic alkyl having 1 to 6 carbon atoms, optionally bearing a secondary amino (e.g., —NHR$^{101}$) or tertiary amino (—NR$^{101}$R$^{102}$) group or a 5- or 6-membered nitrogen containing heterocycle, such as piperidine or morpholine, wherein R$^{101}$ and R$^{102}$ are each independently a linear, branched, or cyclic alkyl, alkenyl or alkynyl having 1 to 10 carbon atoms;

R, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit —(CH$_2$CH$_2$O)$_n$—R$^c$, and an optionally substituted 3- to 18-membered heterocyclic ring having 1 to 6 heteroatoms independently selected from O, S, N and P;

R$^c$ is —H or an optionally substituted linear or branched alkyl having 1 to 4 carbon atoms;

n is an integer from 1 to 24;

X$_1$' is selected from —H, an amine-protecting group, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y$_1$' is selected from —H, an oxo group (i.e., Y$_1$' together with the carbon atom to which it is attached form the —C(=O)— group), an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms;

R$_1$, R$_2$, R$_3$, R$_4$, R$_1$', R$_2$', R$_3$' and R$_4$' are each independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, halogen, guanidinium [—NH(C=NH)NH$_2$], —OR, —NR'R", —NO$_2$, —NCO, —NR'COR", —SR, —SOR', —SO$_2$R', —SO$_3$$^-$H, —OSO$_3$H, —SO$_2$NR'R", cyano, an azido, —COR', —OCOR', and —OCONR'R";

R$_6$ is —H, —R, —OR, —SR, —NR'R", —NO$_2$, or halogen;

G is —CH— or —N—;

A and A' are the same or different, and are independently selected from —O—, oxo (—C(=O)—), —CRR'O—, —CRR'—, —S—, —CRR'S—, —NR$_5$ and —CRR'N(R$_5$)—; and $R_5$ for each occurrence is independently —H or an optionally substituted linear or branched alkyl having 1 to 10 carbon atoms.

In a more specific embodiment, D is represented by formula (IGN1') or (IGN1).

In another more specific embodiment, for formulas (IGN1')-(IGN4') and (IGN1)-(IGN4), one of L', L" and L'" is represented by formula (A') or (D'), and the others are —H, an linear or branched alkyl having from 1 to 6 carbon atoms, halogen, —OH, ($C_1$-$C_6$)alkoxy, or —$NO_2$.

In another more specific embodiment, for formulas (IGN1')-(IGN4') and (IGN1)-(IGN4), L' is represented by formula (A'); and L" and L'" are both —H.

In another more specific embodiment, for formulas (IGN1')-(IGN4') and (IGN1)-(IGN4), L' is represented by formula (D'); and L" and L'" are both —H.

In another more specific embodiment, for formulas (IGN1')-(IGN4') and (IGN1)-(IGN4), $R_{x1}$ is a linear, branched or cyclic alkyl having 1 to 6 carbon atoms optionally substituted with halogen, —OH, —$SO_3H$, ($C_1$-$C_3$)alkyl, ($C_1$-$C_3$)alkoxy, halo($C_1$-$C_3$)alkyl, or a charged substituent or an ionizable group Q.

In a $2^{nd}$ specific aspect, for formulas (IGN1')-(IGN4') and (IGN1)-(IGN4), L' is represented by the following formula:

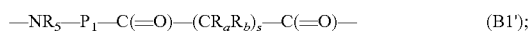

—$NR_5$—$P_1$—C(=O)—($CR_aR_b$)$_s$—C(=O)— (B1');

—$NR_5$—$P_1$—C(=O)—Cy-($CR_aR_b$)$_{s1}$—C(=O)— (B2');

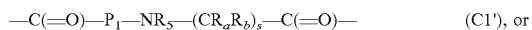

—C(=O)—$P_1$—$NR_5$—($CR_aR_b$)$_s$—C(=O)— (C1'), or

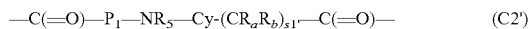

—C(=O)—$P_1$—$NR_5$—Cy-($CR_aR_b$)$_{s1}$—C(=O)— (C2')

wherein:

$R_a$ and $R_b$, for each occurrence, are each independently —H, ($C_1$-$C_3$)alkyl or a charged substituent or an ionizable group Q;

s is an integer from 1 to 6;

s1' is 0 or an integer from 1 to 6; and

Cy is a cyclic alkyl having 5 or 6 ring carbon atoms optionally substituted with halogen, —OH, ($C_1$-$C_3$)alkyl, ($C_1$-$C_3$)alkoxy, or halo($C_1$-$C_3$)alkyl;

and the remaining variables are as described above in the $1^{st}$ specific aspect or any specific or more specific embodiments described therein.

In a more specific embodiment, $R_a$ and $R_b$ are both H; Cy in formulas (B2') and (C2') is cyclohexane; and $R_5$ is H or Me. Even more specifically, s1' is 0 or 1.

In a $3^{rd}$ specific aspect, for formulas (IGN1')-(IGN4') and (IGN1)-(IGN4), $P_1$ is a peptide containing 2 to 10 amino acid residues; and the remaining variables are as described in the $1^{st}$ or $2^{nd}$ specific aspect or any specific or more specific embodiments described therein.

In specific embodiments, $P_1$ is a peptide containing 2 to 5 amino acid residues.

In another specific embodiments, $P_1$ is Gly-Gly-Gly, Ala-Val, Val-Cit, Val-Lys, Phe-Lys, Lys-Lys, Ala-Lys, Phe-Cit, Leu-Cit, Ile-Cit, Trp, Cit, Phe-Ala, Phe-$N^9$-tosyl-Arg, Phe-$N^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 1), β-Ala-Leu-Ala-Leu (SEQ ID NO: 2), Gly-Phe-Leu-Gly (SEQ ID NO: 3), Val-Arg, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, Gln-Val, Asn-Ala, Gln-Phe and Gln-Ala. Even more specifically, P is Gly-Gly-Gly, Ala-Val, Ala-Ala, Ala-D-Ala, D-Ala-Ala, or D-Ala-D-Ala.

In a $4^{th}$ specific aspect, for formulas (IGN1')-(IGN4') and (IGN1)-(IGN4), $X_1$' is selected from the group consisting of —H, —OH, an optionally substituted linear, branched or cyclic alkyl, alkenyl or alkynyl having from 1 to 10 carbon atoms, and phenyl; $Y_1$' is selected from the group consisting of —H, an oxo group, an optionally substituted linear, branched or cyclic alkyl, alkenyl or alkynyl having from 1 to 10 carbon atoms; and the remaining variables are as described above in the $1^{st}$, $2^{nd}$, or $3^{rd}$ specific aspect or any specific or more specific embodiments described therein. More specifically, $X_1$' is —H, —OH, ($C_1$-$C_3$)alkyl, halo($C_1$-$C_3$)alkyl, or phenyl; and $Y_1$' is —H, an oxo group, ($C_1$-$C_3$) alkyl or halo($C_1$-$C_3$)alkyl. In another more specific embodiment, $X_1$' is —H, —OH or —Me; and $Y_1$' is —H or oxo. Even more specifically, $X_1$' is —H; and $Y_1$' is —H.

In a $5^{th}$ specific aspect, for formulas (IGN1')-(IGN4') and (IGN1)-(IGN4), A and A' are the same or different, and are —O—, —S—, or oxo —(C=O)—; and the remaining variables are as described above in the $1^{st}$, $2^{nd}$, $3^{rd}$, or $4^{th}$ specific aspect or any specific or more specific embodiments described therein. More specifically, A and A' are the same or different, and are —O— or —S—. Even more specifically, A and A' are —O—.

In a $6^{th}$ specific aspect, for formulas (IGN1')-(IGN4') and (IGN1)-(IGN4), $R_6$ is —OR, wherein R is an alkyl group having 1 to 6 carbon atoms; and the remaining variables are as described above in the $1^{st}$, $2^{nd}$, $3^{rd}$, $4^{th}$ or $5^{th}$ specific aspect or any specific or more specific embodiments described therein. More specifically, $R_6$ is —OMe.

In a $7^{th}$ specific aspect, for formulas (IGN1)-(IGN4), $R_1$, $R_2$, $R_3$, $R_4$, $R_1$', $R_2$', $R_3$' and $R_4$' are each independently —H, halogen, —$NO_2$, —OH, ($C_1$-$C_3$)alkyl, halo($C_1$-$C_3$)alkyl or ($C_1$-$C_3$)alkoxy; and the remaining variables are as described above in the $1^{st}$, $2^{nd}$, $3^{rd}$, $4^{th}$, $5^{th}$ or $6^{th}$ specific aspect or any specific or more specific embodiments described therein. More specifically, $R_1$, $R_2$, $R_3$, $R_4$, $R_1$', $R_2$', $R_3$' and $R_4$' are all —H.

In a $8^{th}$ specific aspect, for formulas (IGN1')-(IGN4') and (IGN1)-(IGN4), R, R', R" and $R_5$ are each independently —H or ($C_1$-$C_3$)alkyl; and the remaining variables are as described above in the $1^{st}$, $2^{nd}$, $3^{rd}$, $4^{th}$, $5^{th}$, $6^{th}$ or $7^{th}$ specific aspect or any specific or more specific embodiments described therein.

In a $9^{th}$ specific aspect, for formulas (IGN1')-(IGN4') and (IGN1)-(IGN4):

$R_1$, $R_2$, $R_3$, $R_4$, $R_1$', $R_2$', $R_3$' and $R_4$' are all —H;

$R_6$ is —OMe;

$X_1$' and $Y_1$' are both —H; and

A and A' are —O—;

and the remaining variables are as described above in the $1^{st}$, $2^{nd}$, or $3^{rd}$ specific aspect or any specific or more specific embodiments described therein. More specifically, R, R', R" and $R_5$ are each independently —H or ($C_1$-$C_3$)alkyl. Even more specifically, R, R', R" and $R_5$ are all —H.

In a $10^{th}$ specific aspect, for the imine-containing cytotoxic agent of formula (A) or the conjugate of formula (B), D is represented by the following structural formula:

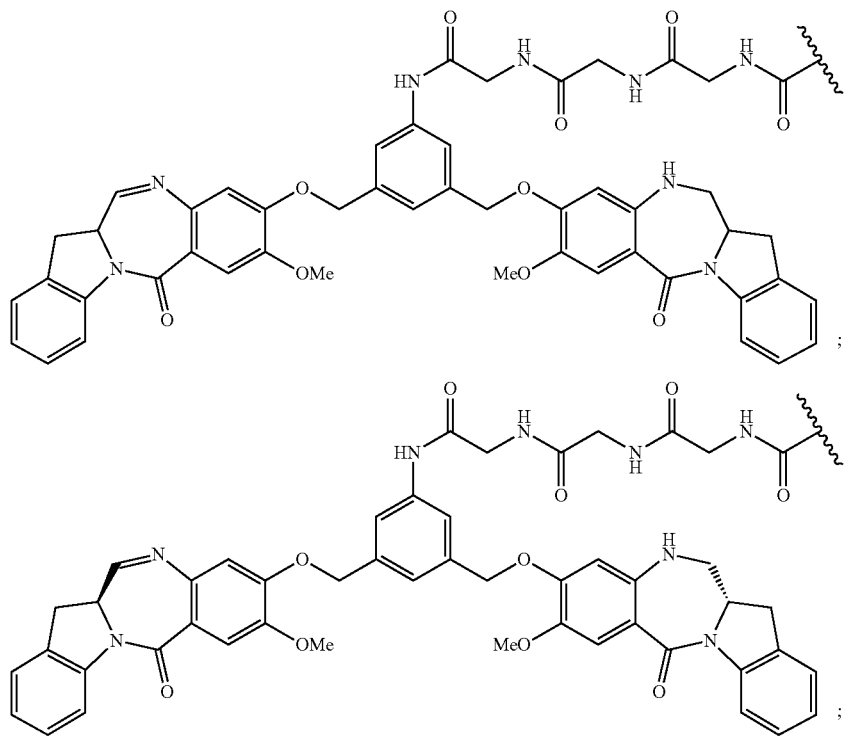
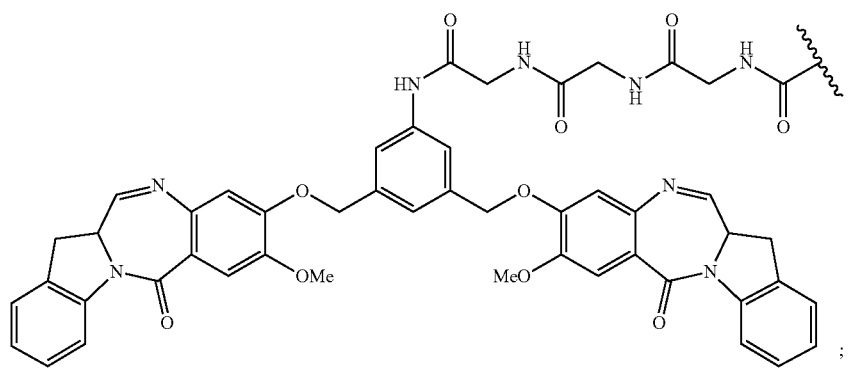
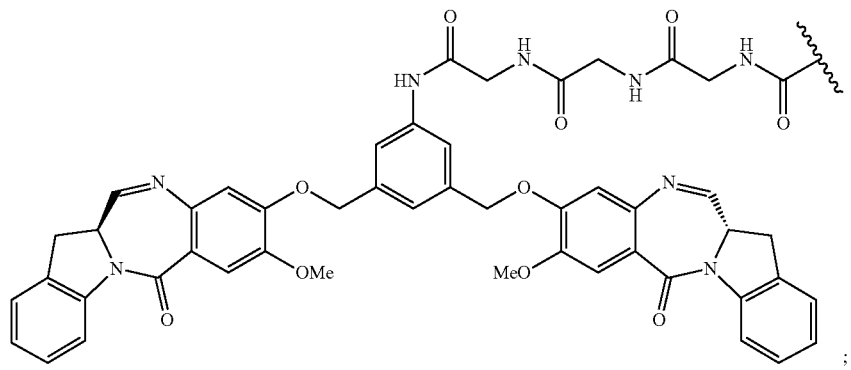

-continued
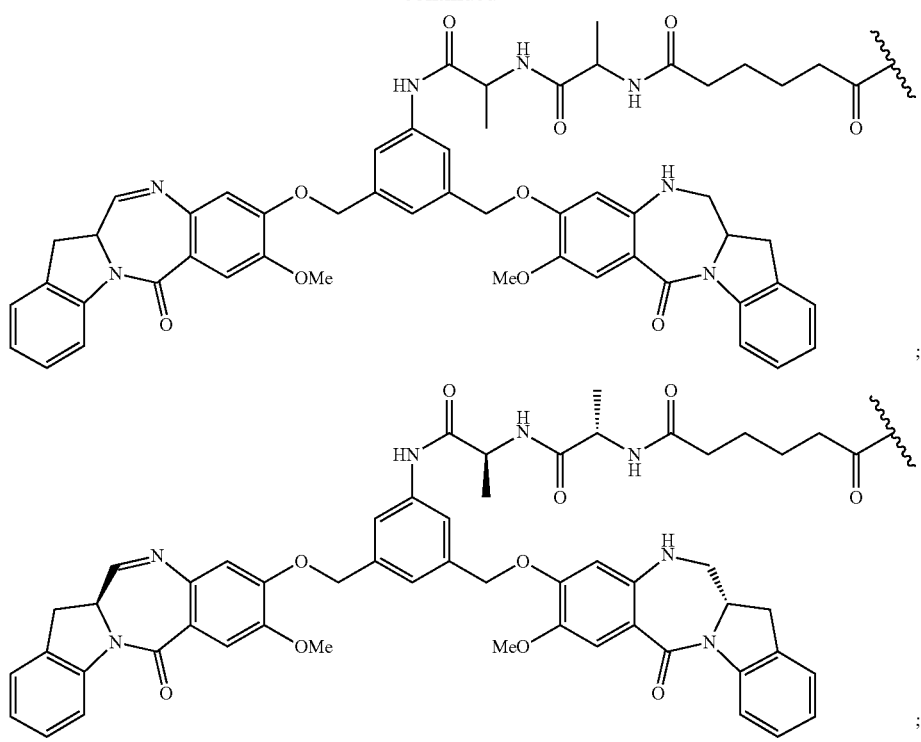
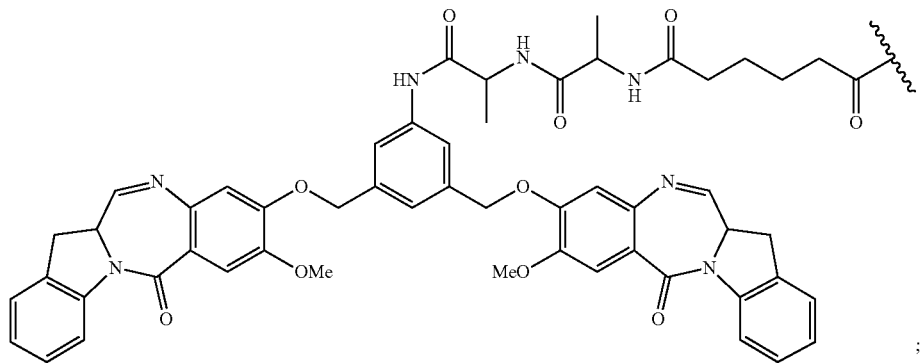
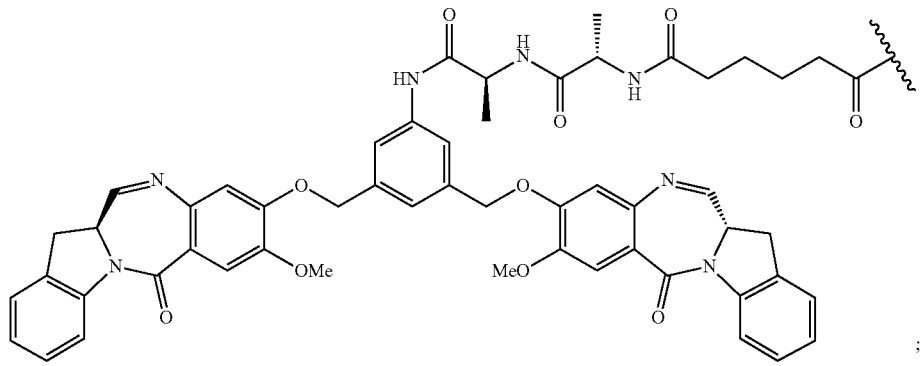

-continued
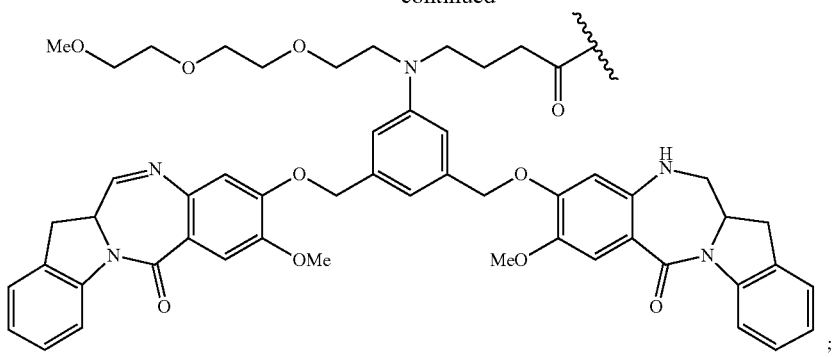
;
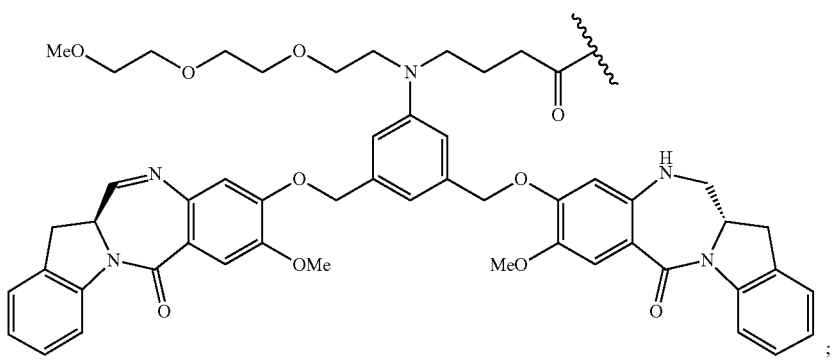
;
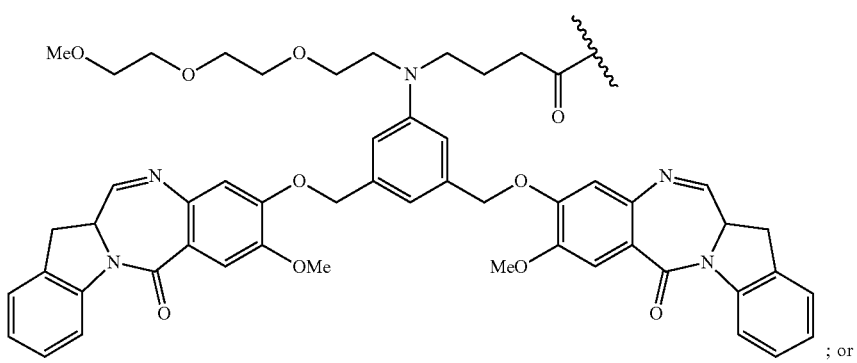
; or
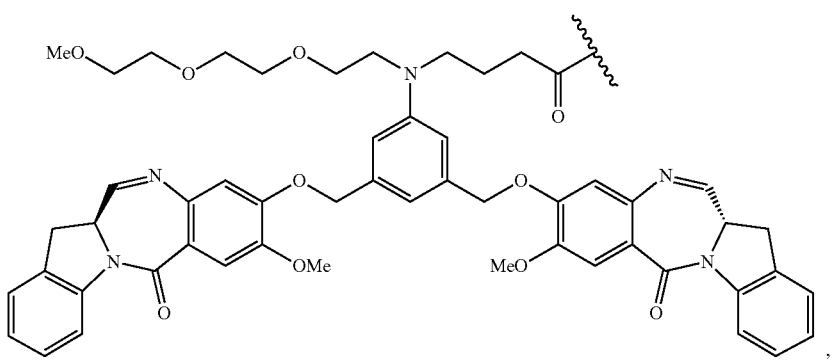
,
or a pharmaceutically acceptable salt thereof; and the remaining variables are described for formula (A) or (B) described above.
In a 11$^{th}$ specific aspect, for the imine-containing cytotoxic agent of formula (A) or the conjugate of formula (B), -L- is represented by the following structural formula:

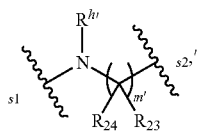
(L1)

wherein:
s1 is the site covalently linked to D; s2 is the site covalently linked to the maleimide group;
$R_{23}$ and $R_{24}$, for each occurrence, are independently H or an optionally substituted alkyl;
m' is an integer between 0 and 10; and
$R^{h'}$ is H or an optionally substituted alkyl;
and the remaining variables are as described above for formula (A) or formula (B), or in the $1^{st}$ to $10^{th}$ specific aspect, or any specific or more specific embodiments described therein.

In a specific embodiment, m' is an integer from 1 to 6. Even more specifically, m' is an integer from 1 to 3.

In another specific embodiment, $R_{23}$ and $R_{24}$, for each occurrence, are independently H or a $(C_1-C_3)$alkyl. Even more specifically, $R_{23}$ and $R_{24}$ are both H.

In another specific embodiment, $R^{h'}$ is H or a $(C_1-C_3)$ alkyl. More specifically, $R^{h'}$ is H.

In another specific embodiment, $R_{23}$ and $R_{24}$ are both H; m' is an integer from 1 to 6. Even more specifically, m' is an integer from 1 to 3.

In a $12^{th}$ specific aspect, for the imine-containing cytotoxic agent of formula (A) or the conjugate of formula (B), -L- is represented by the following structural formula:

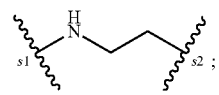

wherein s1 is the site covalently linked to D; s2 is the site covalently linked to the maleimide group; and the remaining variables are as described above for formula (A) or formula (B), or in the $1^{st}$ to $10^{th}$ specific aspect, or any specific or more specific embodiments described therein.

In a $13^{th}$ specific aspect, the imine-containing cytotoxic agent is represented by the following formula:

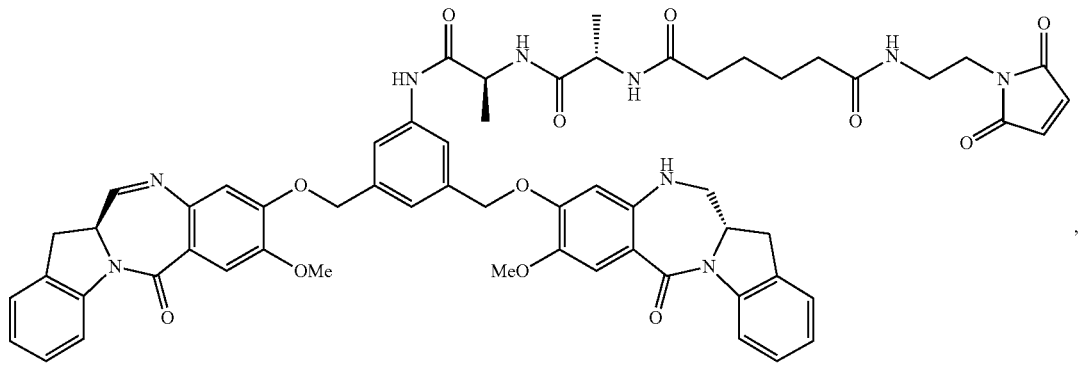 [SMILES: COc1cc2c(cc1OCc1cc(COc3cc4c(cc3OC)C(=O)N3c5ccccc5C[C@H]3CN4)cc(NC(=O)[C@H](C)NC(=O)[C@H](C)NC(=O)CCCCC(=O)NCCN3C(=O)C=CC3=O)c1)N=C[C@@H]1Cc3ccccc3N1C2=O]

or a pharmaceutically acceptable salt thereof, and the modified cytotoxic agent is represented by the following formula:

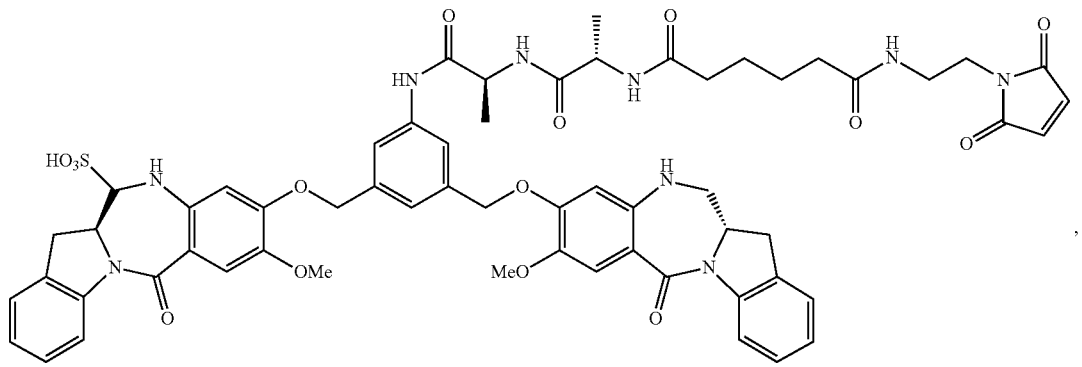

or a pharmaceutically acceptable salt thereof. More specifically, the modified cytotoxic agent is represented by the following formula:

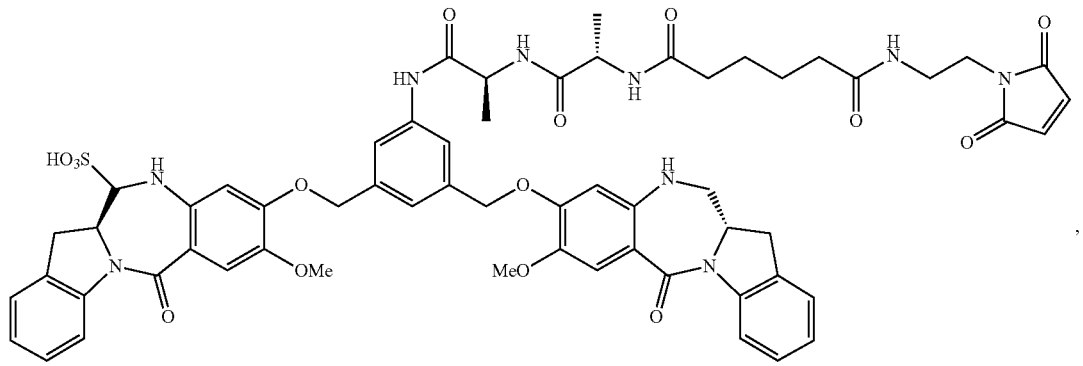

or a sodium or potassium salt thereof. Even more specifically, the modified cytotoxic agent is represented by the following formula:

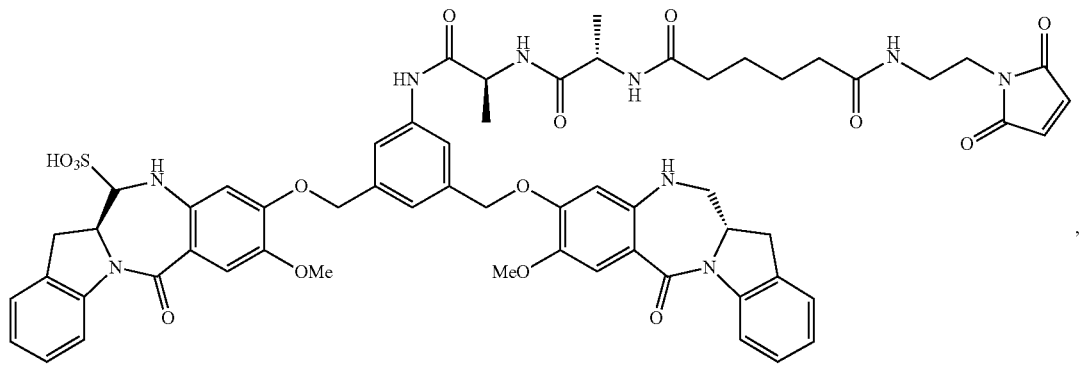

In some embodiments, the imine-containing cytotoxic agent is represented by the following formula:

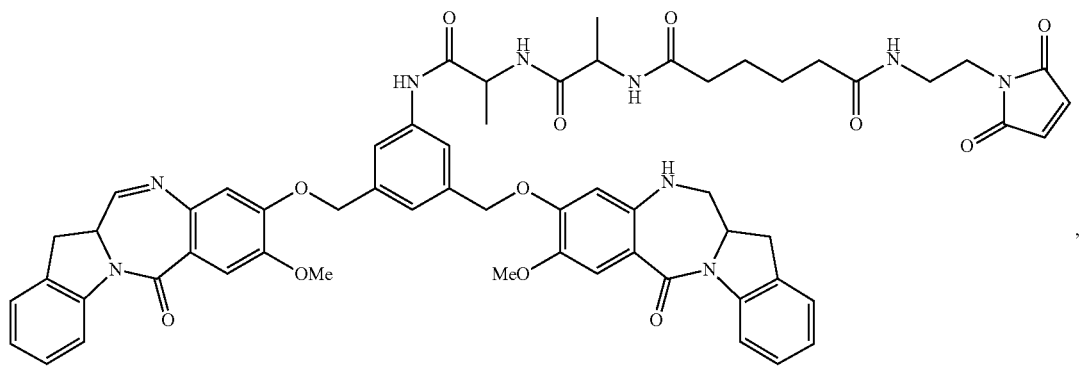 [SMILES: COc1cc2c(cc1OCc1cc(COc3cc4c(cc3OC)C(=O)N3c5ccccc5CC3CN4)cc(NC(=O)C(C)NC(=O)C(C)NC(=O)CCCCC(=O)NCCN3C(=O)C=CC3=O)c1)N=CC1Cc3ccccc3N1C2=O]

or a pharmaceutically acceptable salt thereof, and the modified cytotoxic agent is represented by the following formula:

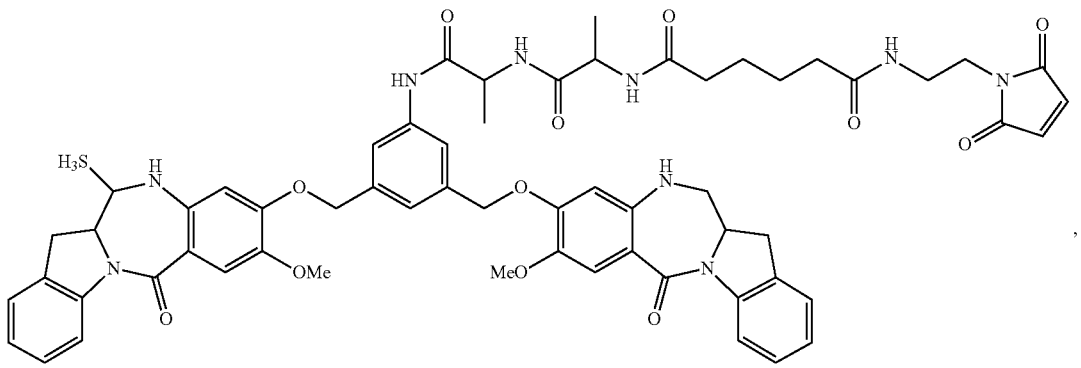 [SMILES: COc1cc2c(cc1OCc1cc(COc3cc4c(cc3OC)C(=O)N3c5ccccc5CC3C(S)N4)cc(NC(=O)C(C)NC(=O)C(C)NC(=O)CCCCC(=O)NCCN3C(=O)C=CC3=O)c1)NCC1Cc3ccccc3N1C2=O]

or a pharmaceutically acceptable salt thereof. More specifically, the modified cytotoxic agent is represented by the following formula:

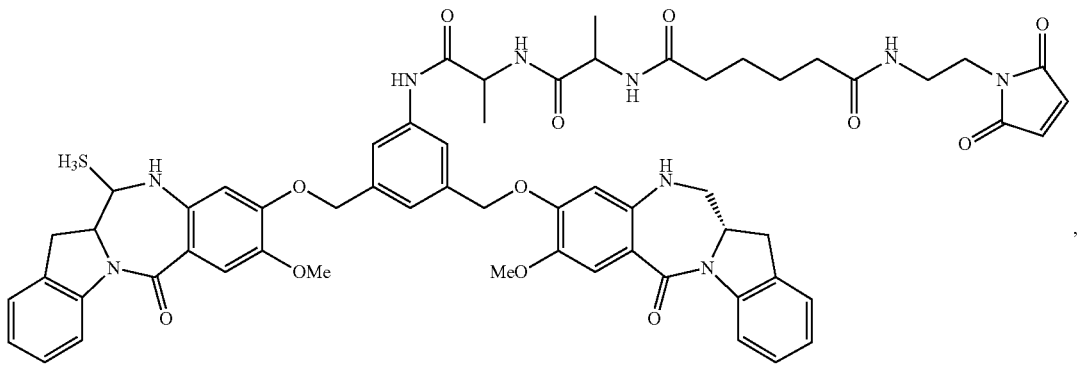 [SMILES: COc1cc2c(cc1OCc1cc(COc3cc4c(cc3OC)C(=O)N3c5ccccc5C[C@H]3CN4)cc(NC(=O)C(C)NC(=O)C(C)NC(=O)CCCCC(=O)NCCN3C(=O)C=CC3=O)c1)NC(S)C1Cc3ccccc3N1C2=O]

or a sodium or potassium salt thereof. Even more specifically, the modified cytotoxic agent is represented by the following formula:

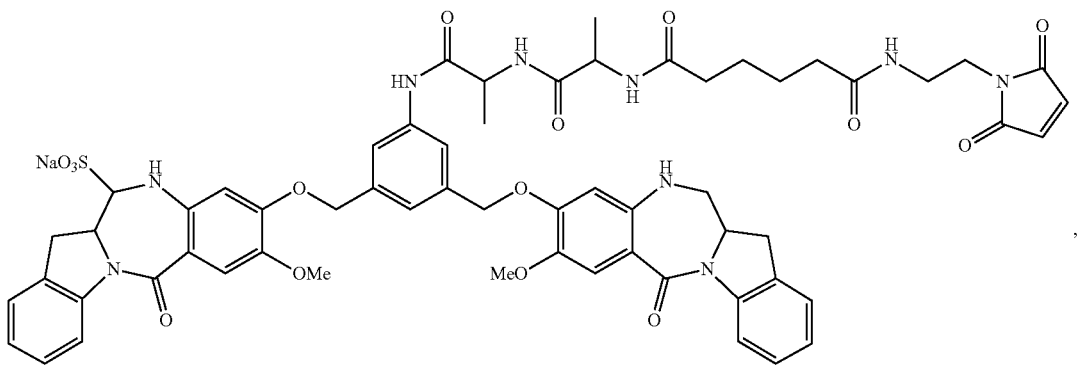

In a 14$^{th}$ specific aspect, for the imine-containing cytotoxic agent of formula (A) or the conjugate of formula (B), D is represented by the following structural formula:

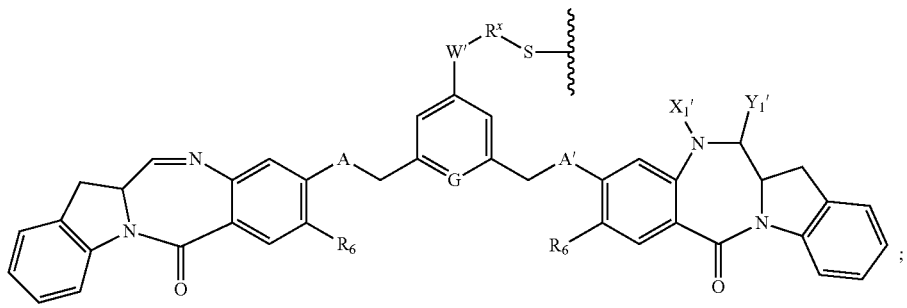
(IGN5')
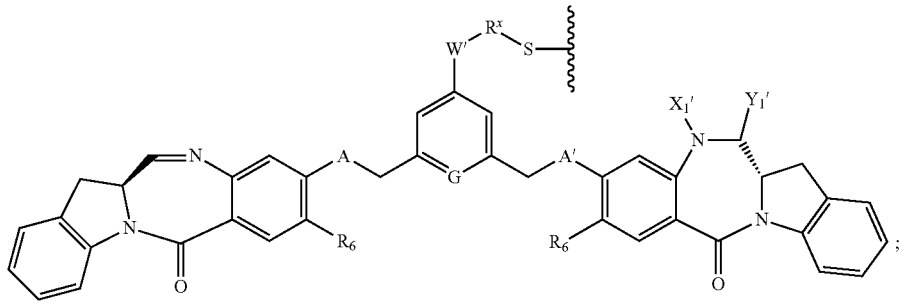
(IGN5)
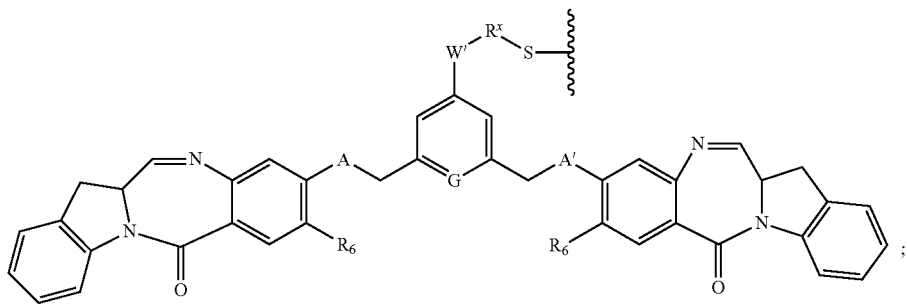
(IGN6')
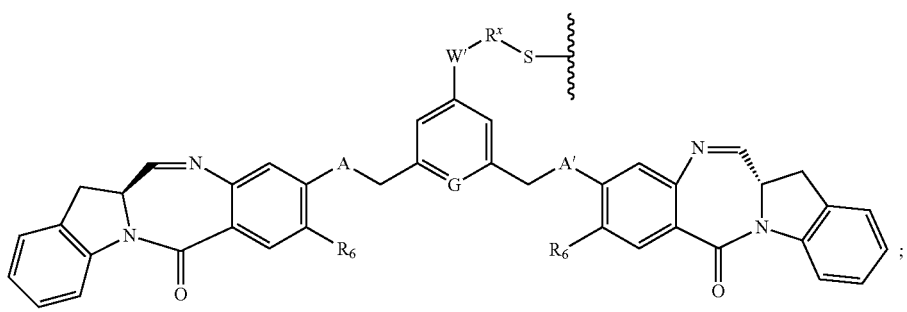
(IGN6)
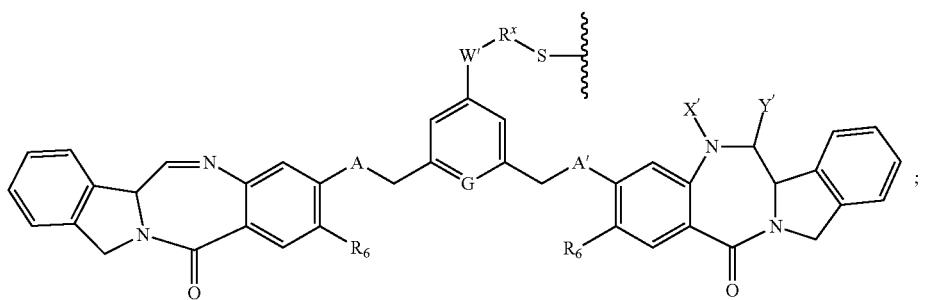
(IGN7')

-continued

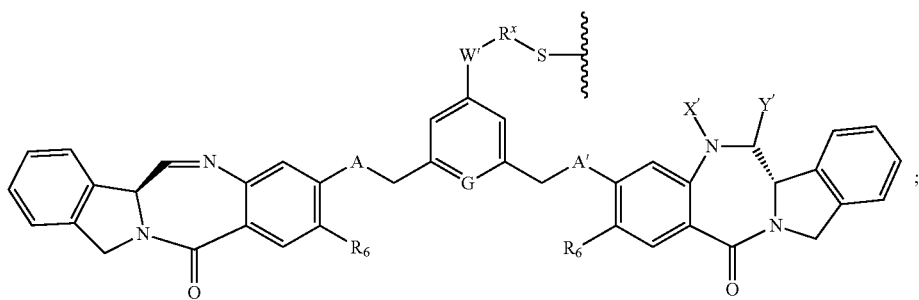
(IGN7)

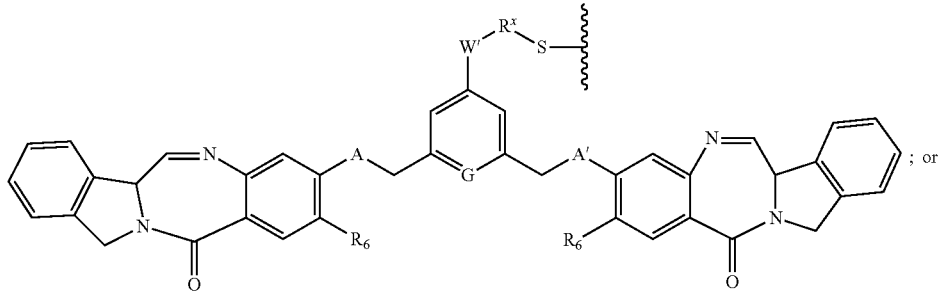
(IGN8')

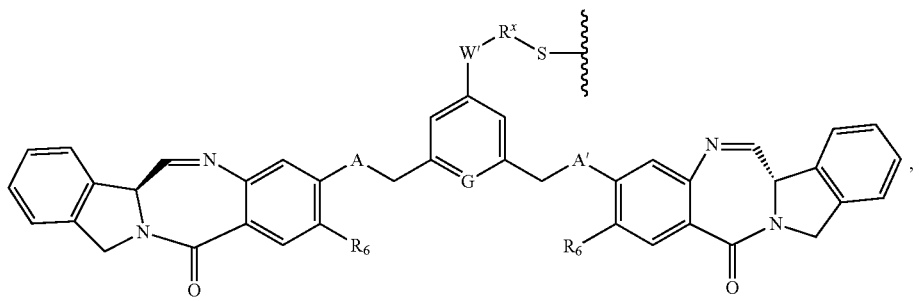
(IGN8)

or a pharmaceutically acceptable salt thereof, wherein:

X' is selected from the group consisting of —H, —OH, a substituted or unsubstituted linear, branched or cyclic alkyl, alkenyl or alkynyl having from 1 to 10 carbon atoms, phenyl, and an amine-protecting group;

Y' is selected from the group consisting of —H, an oxo group, a substituted or unsubstituted linear, branched or cyclic alkyl, alkenyl or alkynyl having from 1 to 10 carbon atoms;

A and A' are selected from —O— and —S—;

W' is absent, or selected from —O—, —N($R^e$)—, —N($R^e$)—C(=O)—, —N(C(=O)$R^e$)—, —S— or —$CH_2$—S—, —$CH_2NR^e$—;

$R^x$ is absent or selected from a linear, branched or cyclic alkyl having 1 to 10 carbon atoms;

$R^e$ is —H, a linear, branched or cyclic alkyl, alkenyl or alkynyl having 1 to 10 carbon atoms or —($CH_2$—$CH_2$—O)$_n$—$R^k$, wherein $R^k$ is a —H, a linear, branched cyclic alkyl having 1 to 6 carbon atoms, optionally bearing a secondary amino (e.g., —$NHR^{101}$) or tertiary amino (—$NR^{101}R^{102}$) group or a 5- or 6-membered nitrogen containing heterocycle, wherein $R^{101}$ and $R^{102}$ are each independently a linear, branched, or cyclic alkyl, alkenyl or alkynyl having 1 to 10 carbon atoms;

n is an integer from 1 to 24;

G is selected from —CH— or —N—;

$R_6$ is —H, —R, —OR, —SR, —NR'R", —$NO_2$, or halogen; and

R is —H, an optionally substituted linear, branched or cyclic alkyl, alkenyl or alkynyl having from 1 to 10 carbon atoms or a PEG group —($CH_2CH_2O$)$_n$—$R^c$, wherein n is an integer from 1 to 24, and $R^c$ is a linear or branched alkyl having 1 to 4 carbon atoms;

R' and R" are each independently selected from —H, —OH, —OR, —NRR$^{g'}$, —COR, an optionally substituted linear, branched or cyclic alkyl, alkenyl or alkynyl having from 1 to 10 carbon atoms, an optionally substituted aryl having from 6 to 18 carbon atoms, an optionally substituted 3- to 18-membered heterocyclic ring having 1 to 6 heteroatoms selected from O, S, N and P, a PEG group —($CH_2CH_2O$)$_n$—$R^c$, and $R^{g'}$ is —H, an optionally substituted linear, branched or cyclic alkyl, alkenyl or alkynyl having from 1 to 10 carbon atoms or a PEG group —($CH_2CH_2O$)$_n$—$R^c$.

In a more specific embodiment, D is represented by formula (IGN5') or (IGN5) above, or a pharmaceutically acceptable salt thereof.

In another specific embodiment, for formulas (IGN5')-(IGN8') and (IGN5)-(IGN8):

X' and Y' are both —H;

A and A' are both —O—;

$R_6$ is —OMe;

W' is —N($R^e$)— or —N($R^e$)—C(=O)—;

$R^e$ is —H, a linear or branched alkyl having 1 to 4 carbon atoms or —(CH$_2$—CH$_2$—O)$_n$—R$^k$, wherein $R^k$ is a —H, a linear or branched alkyl having 1 to 4 carbon atoms;

n is an integer from 2 to 6; and $R^x$ is a linear or branched alkyl having 1 to 6 carbon atoms.

In a 15$^{th}$ specific aspect, for the imine-containing cytotoxic agent of formula (A) or the conjugate of formula (B), D is represented by the following structural formula:

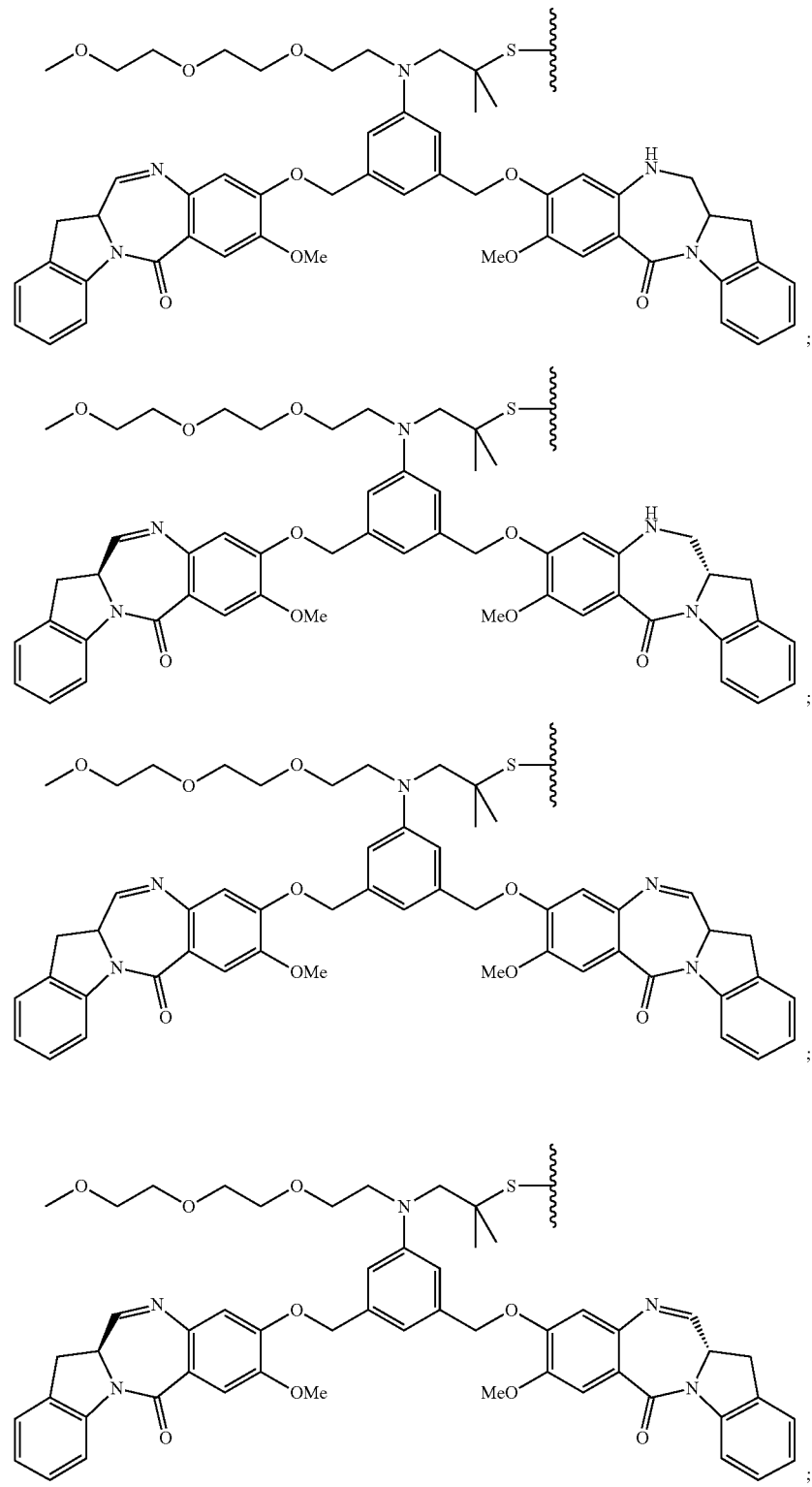

-continued
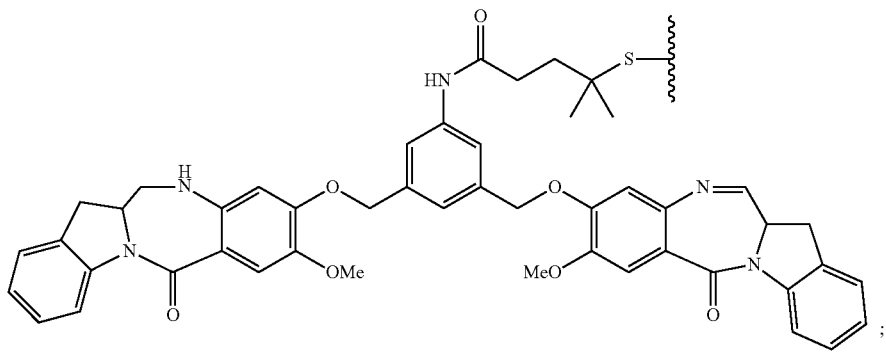;
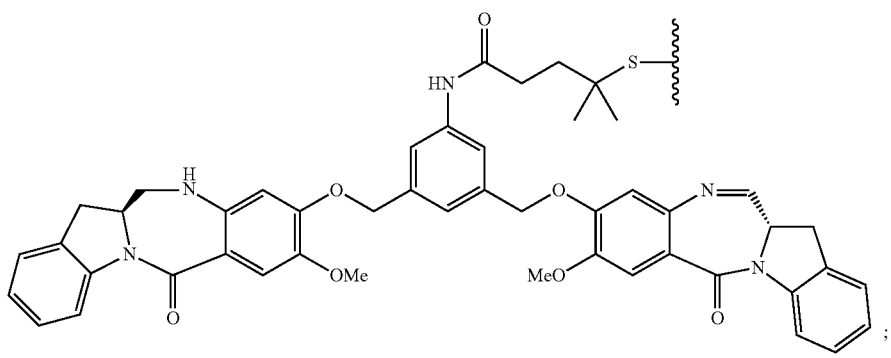;
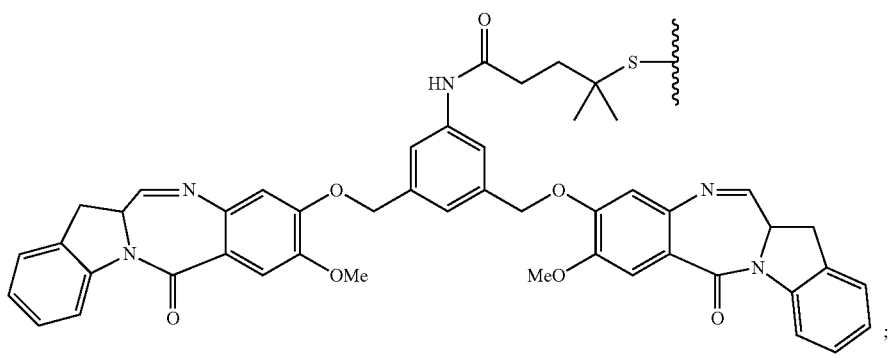;
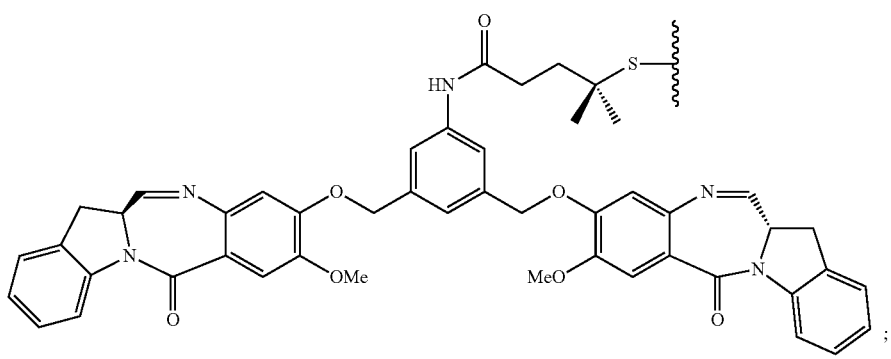;

or a pharmaceutically acceptable salt thereof, wherein the remaining variables are as described above for formula (A) or (B).

In a 16$^{th}$ specific aspect, for the imine-containing cytotoxic agent of formula (A) or the conjugate of formula (B), -L- is represented by the following structural formula:

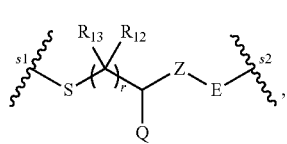
(L2)

wherein:

s1 is the site covalently linked to D, and s2 is the site covalently linked to the maleimide group;

E is —$(CR_{10}R_{11})_q$—, cycloalkyl, or cycloalkylalkyl;

Z is absent, —$SO_2NR_9$—, —$NR_9SO_2$—, —$C(=O)$—$NR_9$—, —$NR_9$—$C(=O)$—, —$C(=O)$—$O$—, —$O$—$C(=O)$—, —$C(=O)$—$NR_9$—$(CH_2CH_2O)_p$—, —$NR_9$—$C(=O)$—$(CH_2CH_2O)_p$—, —$(OCH_2CH_2)_p$—$C(=O)NR_9$—, or —$(OCH_2CH_2)_p$—$NR_9$—$C(=O)$—;

p is an integer from 1 to 24;

Q is H, a charged substituent, or an ionizable group;

$R_9$, $R_{10}$, $R_{11}$, $R_{12}$, and $R_{13}$, for each occurrence, are independently H or an optionally substituted alkyl; and, q and r, for each occurrence, are independently an integer between 0 and 10; and the remaining variables are as described above for formula (A) or formula (B), or in 14$^{th}$ or 15$^{th}$ specific aspect or any specific or more specific embodiments described therein.

In a more specific embodiment, q and r, are independently an integer from 1 to 6, more specifically, 1 to 3.

In another more specific embodiment, $R_9$, $R_{10}$, $R_{11}$, $R_{12}$, and $R_{13}$, for each occurrence, are independently H or a $C_{1-3}$alkyl. More specifically, $R_9$, $R_{10}$, $R_{11}$, $R_{12}$, and $R_{13}$ are all H.

In another more specific embodiment, p is an integer from 2 to 14. More specifically, p is an integer from 2 to 8, 2 to 6 or 2 to 4.

In a more specific embodiment, E is —$(CR^{10}R^{11})_q$—; and the remaining variables in formula (L2) are as described above in the 16$^{th}$ specific aspect.

In another more specific embodiment, E is

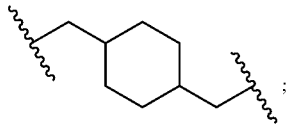 [SMILES: *CC1CCC(C*)CC1]

and the remaining variables in formula (L2) are as described above in the 16$^{th}$ specific aspect.

In yet another specific embodiment, Z is —$C(=O)$—$NR_9$— or —$NR_9$—$C(=O)$—; and the remaining variables in formula (L2) are as described above in the 16$^{th}$ specific aspect or any specific or more specific embodiments described above. Even more specifically, $R_9$ is H or Me. Alternatively, $R_9$ is H.

In yet another more specific embodiment, Q is i) H; ii) —$SO_3H$, —Z'—$SO_3H$, —$OPO_3H_2$, —Z'—$OPO_3H_2$, —$PO_3H_2$, —Z'—$PO_3H_2$, —$CO_2H$, —Z'—$CO_2H$, —$NR_{14}R_{15}$, or —Z'—$NR_{14}R_{15}$, or a pharmaceutically acceptable salt thereof; or, iii) —$N^+R_{14}R_{15}R_{16}X^-$ or —Z'—$N^+R_{14}R_{15}R_{16}X^-$; Z' is an optionally substituted alkylene, an optionally substituted cycloalkylene or an optionally substituted phenylene; $R_{14}$ to $R_{16}$ are each independently an optionally substituted alkyl; and $X^-$ is a pharmaceutically acceptable anion; and the remaining variables in formula (L2) are as described above in the 16$^{th}$ specific embodiment or any more specific embodiments described above. In some embodiments, Z' is an optionally substituted alkylene. In yet other embodiments, Z' is a $C_{1-3}$alkylene (e.g., —$CH_2$); and $R_{14}$ to $R_{16}$ are each independently a $C_{1-4}$alkyl.

In yet another ore specific embodiment, Q is H, or —$SO_3H$, or a pharmaceutically acceptable cation (e.g., sodium or potassium salt); and the remaining variables in formula (L2) are as described above in the 16$^{th}$ specific aspect or any specific or more specific embodiments described above.

In another more specific embodiment, for formula (L2):

$R_{12}$ and $R_{13}$, for each occurrence, are each independently H or $(C_1$-$C_3)$alkyl;

Q is H or —$SO_3H$ or a pharmaceutically acceptable salt thereof

Z is —$C(=O)$—$NR_9$— or —$NR_9$—$C(=O)$—;

$R_9$ is H or $(C_1$-$C_3)$alkyl;

E is —$(CR_{10}R_{11})_q$—.

$R_{10}$ and $R_{11}$, for each occurrence, are independently H or $(C_1$-$C_3)$alkyl; and q and r are each an integer from 1 to 5.

In a 17$^{th}$ specific aspect, for the imine-containing cytotoxic agent of formula (A) or the conjugate of formula (B), -L- is represented by any one of the following structural formulae:

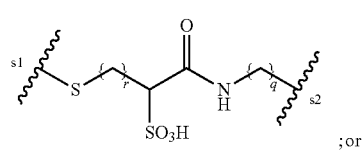
(L2a)
; or

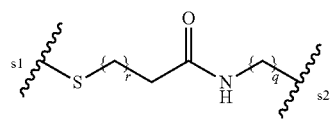
(L2b)

or a pharmaceutically acceptable salt (e.g., sodium or potassium salt) thereof, wherein s1 is the site covalently linked to D, and s2 is the site covalently linked to the maleimide group; q and r are each independently an integer from 1 to 6; and the remaining variables are as described above for formula (A) or formula (B), or in 14$^{th}$ or 15$^{th}$ specific aspect or any specific or more specific embodiments described therein. More specifically, q and r are each independently an integer from 1 to 3.

In a 18$^{th}$ specific aspect, for the imine-containing cytotoxic agent of formula (A) or the conjugate of formula (B), -L- is represented by any one of the following structural formulae:

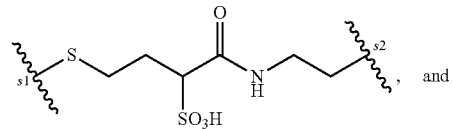
and

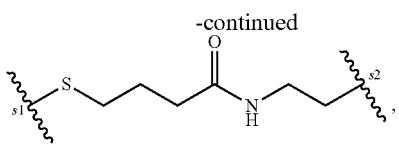

or a pharmaceutically acceptable salt (e.g., sodium or potassium salt) thereof, wherein s1 is the site covalently linked to D, and s2 is the site covalently linked to the maleimide group; and the remaining variables are as described above for formula (A) or formula (B), or in 14th or 15th specific aspect or any specific or more specific embodiments described therein.

In a 19th specific aspect, for the imine-containing cytotoxic agent of formula (A) or the conjugate of formula (B), -L- is represented by the following structural formula:

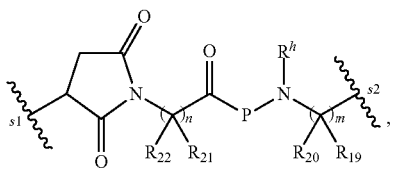

wherein:
s1 is the site covalently linked to D; s2 is the site covalently linked to the maleimide group;
$R_{19}$, $R_{20}$, $R_{21}$ and $R_{22}$, for each occurrence, are independently H or an optionally substituted alkyl;
m and n are each independently an integer between 0 and 10;
$R^h$ is H or an optionally substituted alkyl;
$P_L$ is an optionally substituted alkylene, —(CH$_2$—CH$_2$—O)$_j$— (wherein the oxygen atom is connected to the —(C=O)— group connected to P), an amino acid residue or a peptide containing 2 to 20 amino acid residues; and
j is an integer from 1 to 24; and the remaining variables are as described above for formula (A) or formula (B), or the 14th or 15th specific aspect, or any specific or more specific embodiments described therein.

In a 20th specific aspect, for formula (L3), $R_{19}$, $R_{20}$, $R_{21}$ and $R_{22}$ are each H or a (C$_1$-C$_3$)alkyl; m and n are each independently an integer between 1 and 6; and the remaining variables are as described above in the 19th specific embodiment or any specific or more specific embodiment described therein. More specifically, $R_{19}$, $R_{20}$, $R_{21}$ and $R_{22}$ are all H. Even more specifically, $R_{19}$, $R_{20}$, $R_{21}$ and $R_{22}$ are all H; and m and n are each independently an integer between 1 and 3.

In a 21st specific aspect, for formula (L3), $P_L$ is an amino acid residue or a peptide containing 2 to 10 amino acid residues; and the remaining variables are as described above in the 19th or 20th specific aspect or any specific or more specific embodiment described therein. More specifically, $P_L$ is a peptide containing 2 to 5 amino acid residues.

In some embodiments, each amino acid residue is the residue of an amino acid independently selected from: a naturally occurring amino acid, a synthetic amino acid, an amino acid analog, and an amino acid mimetic that functions in a manner similar to the naturally occurring amino acids.

In other embodiments, each amino acid residue is the residue of an amino acid independently selected from the group consisting of: Histidine, Alanine, Isoleucine, Arginine, Leucine, Asparagine, Lysine, Aspartic acid, Methionine, Cysteine, Phenylalanine, Glutamic acid, Threonine, Glutamine, Tryptophan, Glycine, Valine, Proline, Serine, Tyrosine, N-methyl-Histidine, N-methyl-Alanine, N-methyl-Isoleucine, N-methyl-Arginine, N-methyl-Leucine, N-methyl-Asparagine, N-methyl-Lysine, N-methyl-Aspartic acid, N-methyl-Methionine, N-methyl-Cysteine, N-methyl-Phenylalanine, N-methyl-Glutamic acid, N-methyl-Threonine, N-methyl-Glutamine, N-methyl-Tryptophan, N-methyl-Glycine, N-methyl-Valine, N-methyl-Proline, N-methyl-Serine, N-methyl-Tyrosine, hydroxyproline, γ-carboxyglutamate, selinocysteine, O-phosphoserine, homoserine, norleucine, methionine sulfoxide, methionine methyl sulfonium, citrulline, Ornithine, cysteine sulfonic acid, cysteine sulfinic acid, 3-aminoalanine, 3-dimethylaminoalanine, 2-amino-4-(dimethylamino)butanoic acid, 2,4-diaminobutanoic acid, 2-amino-6-(dimethylamino)hexanoic acid, 2-amino-5-(dimethylamino)pentanoic acid, and β-alanine, each independently as an L or D isomer. More specifically, each amino acid residue is the residue of an independently selected glycine or alanine.

In other embodiments, $P_L$ is a peptide cleavable by a protease. More specifically, $P_L$ is a peptide cleavable by a protease expressed in tumor tissue. Alternatively, $P_L$ is a peptide cleavable by a lysosomal protease.

In yet other embodiments, $P_L$ is selected from the group consisting of: Ala-Val, Val-Cit, Val-Lys, Phe-Lys, Lys-Lys, Ala-Lys, Phe-Cit, Leu-Cit, Ile-Cit, Trp-Cit, Phe-Ala, Phe-N[9]-tosyl-Arg, Phe-N[9]-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 1), β-Ala-Leu-Ala-Leu (SEQ ID NO: 2), Gly-Phe-Leu-Gly (SEQ ID NO: 3), Val-Arg, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala., Ala-Met, Met-Ala, Gln-Val, Asn-Ala, Gln-Phe, Gln-Ala, Gly-Gly-Gly, Ala-Ala-Ala, D-Ala-Ala-Ala, Ala-D-Ala-Ala, Ala-Ala-D-Ala, Ala-Val-Cit, Ala-Val-Ala, and β-Ala-Gly-Gly-Gly. More specifically, $P_L$ is Gly-Gly-Gly, Ala-Ala-Ala, D-Ala-Ala-Ala, Ala-D-Ala-Ala, Ala-Val-Ala, or β-Ala-Gly-Gly-Gly.

In a 22nd specific aspect, for the imine-containing cytotoxic agent of formula (A) or the conjugate of formula (B), -L- is represented by the following structural formula:

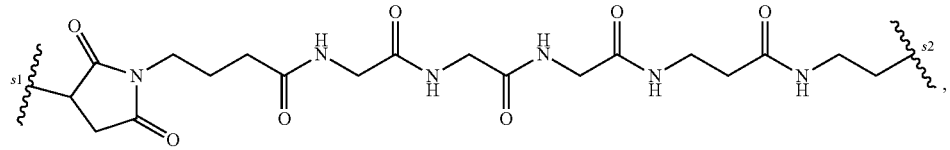 [SMILES: *CCNC(=O)CCNC(=O)CNC(=O)CNC(=O)CNC(=O)CCCN1C(=O)CC(*)C1=O]

or a pharmaceutically acceptable salt thereof, wherein s1 is the site covalently linked to D; s2 is the site covalently linked to the maleimide group; and the remaining variables are as described above for formula (A) or formula (B), or in the 14th or 15th specific aspect.

In a 23rd specific aspect, the imine-containing cytotoxic agent is represented by the following formula:
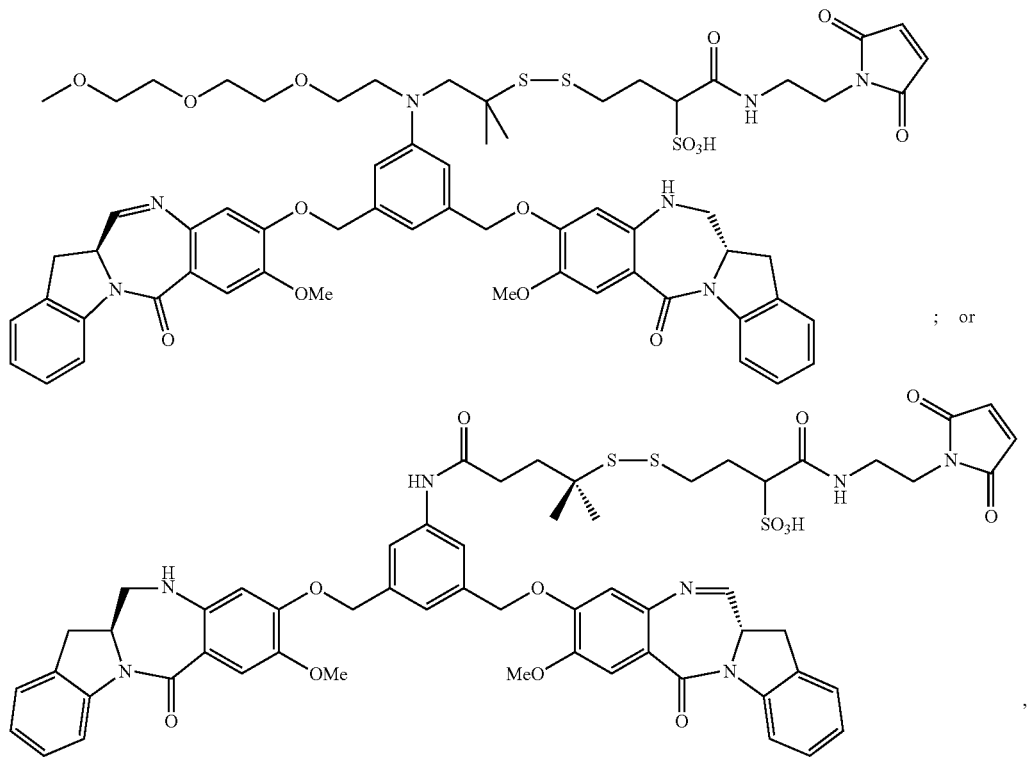
or a pharmaceutically acceptable salt thereof, and the modified cytotoxic agent is represented by the following formula:
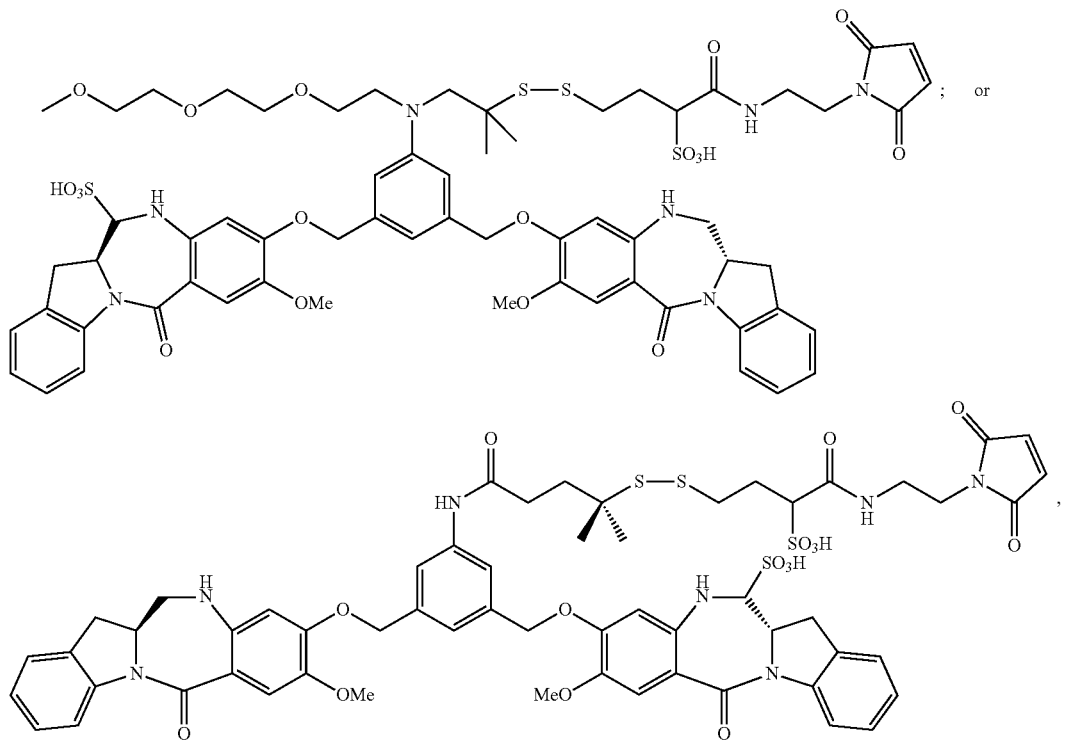
or a pharmaceutically acceptable salt thereof.

In a more specific embodiment, the modified cytotoxic agent is represented by the following formula:
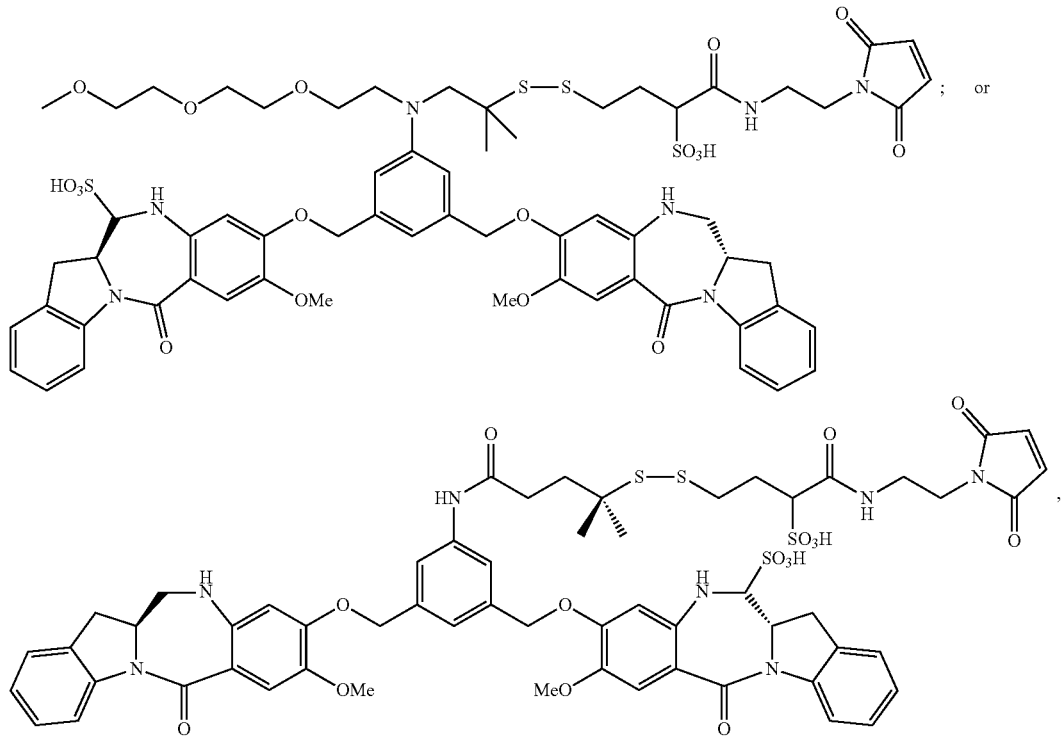
or a sodium or potassium salt thereof. Even more specifically, the modified cytotoxic agent is represented by the following formula:
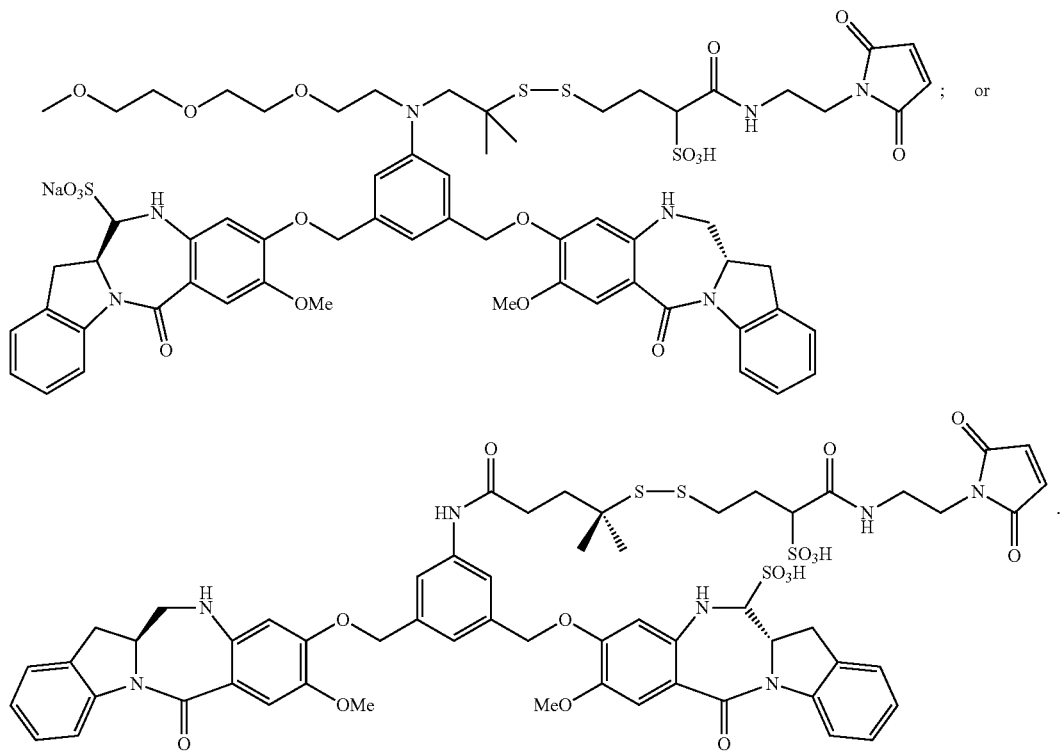

In some embodiments, the imine-containing cytotoxic agent is represented by the following formula:
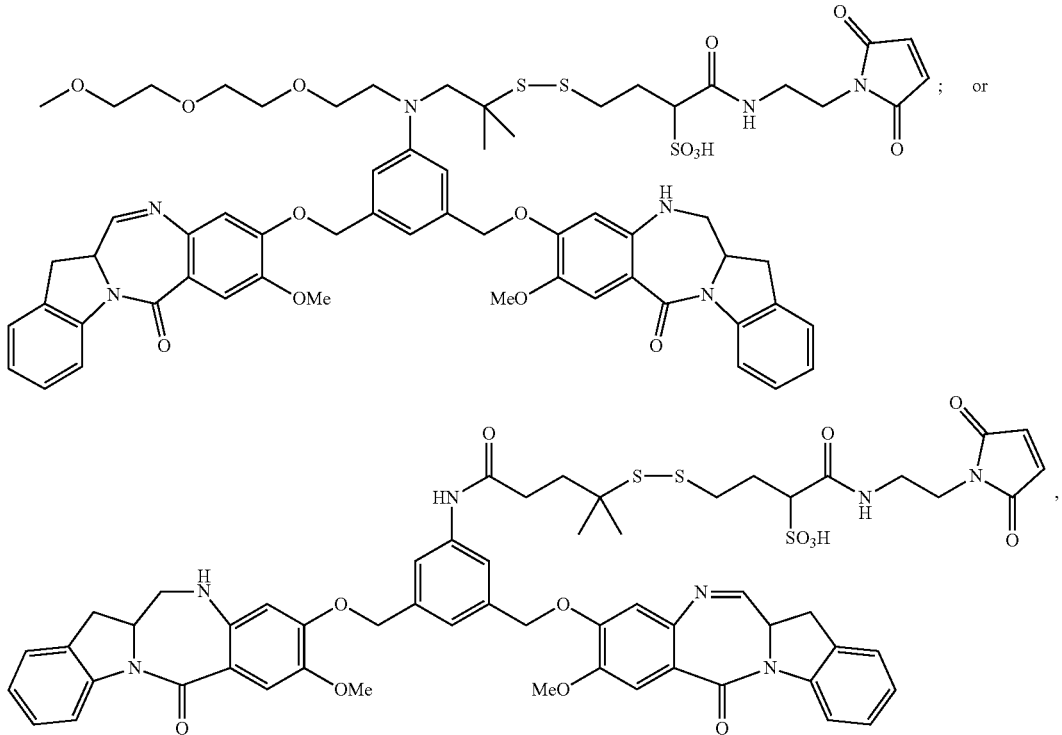
or a pharmaceutically acceptable salt thereof, and the modified cytotoxic agent is represented by the following formula:
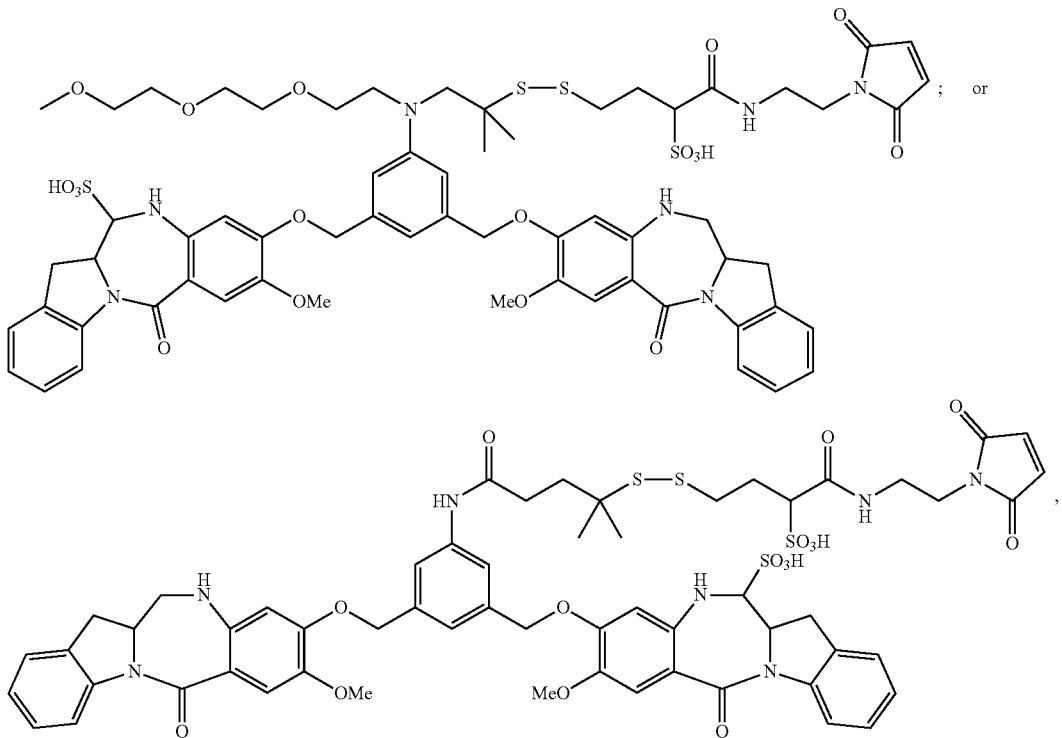
or a pharmaceutically acceptable salt thereof.

In a 24th specific aspect, the conjugate that can be prepared by the methods of the present invention is represented by the following structural formula:
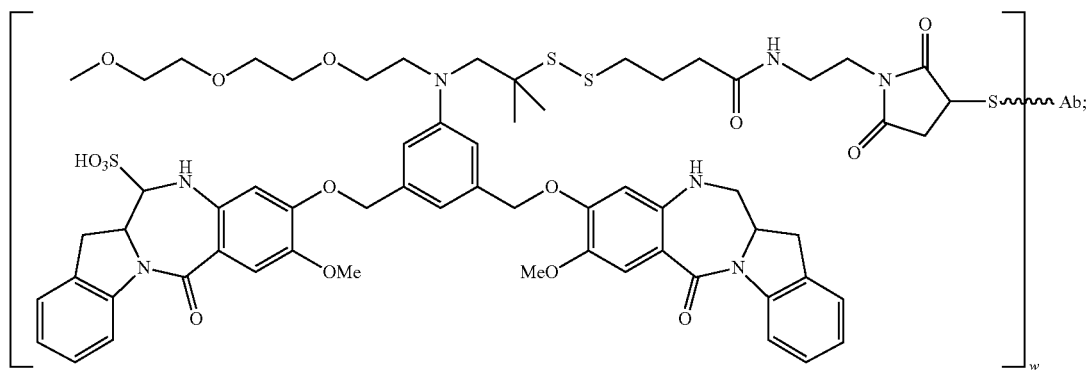
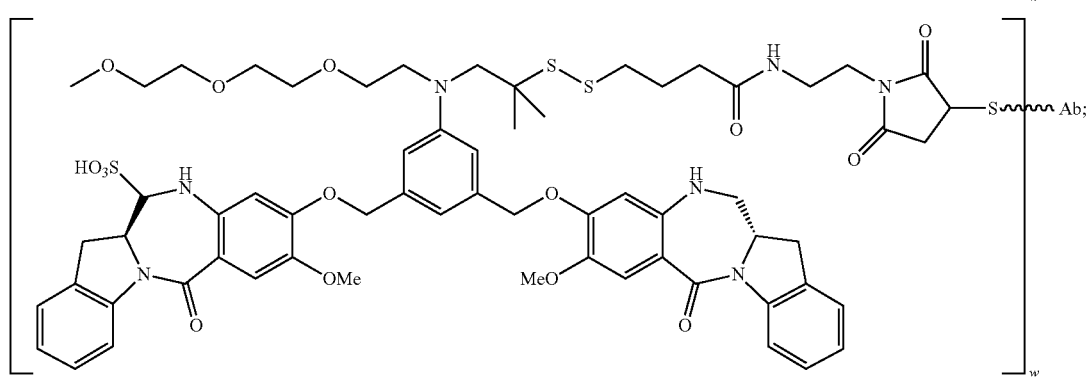
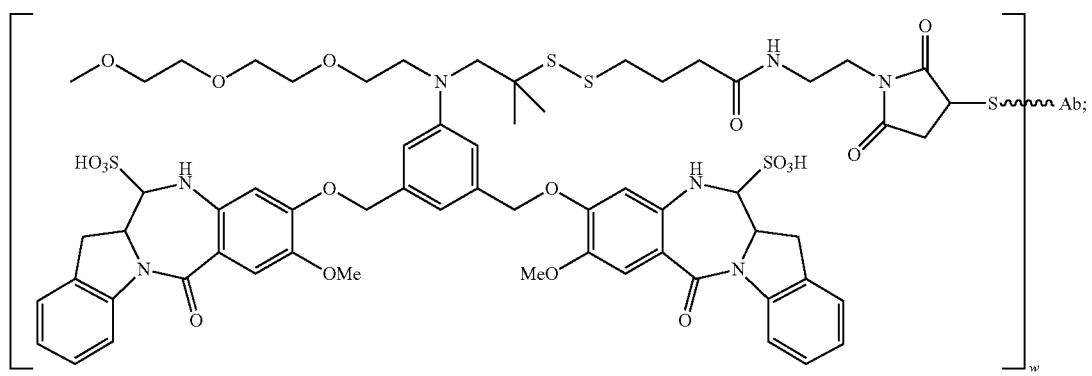
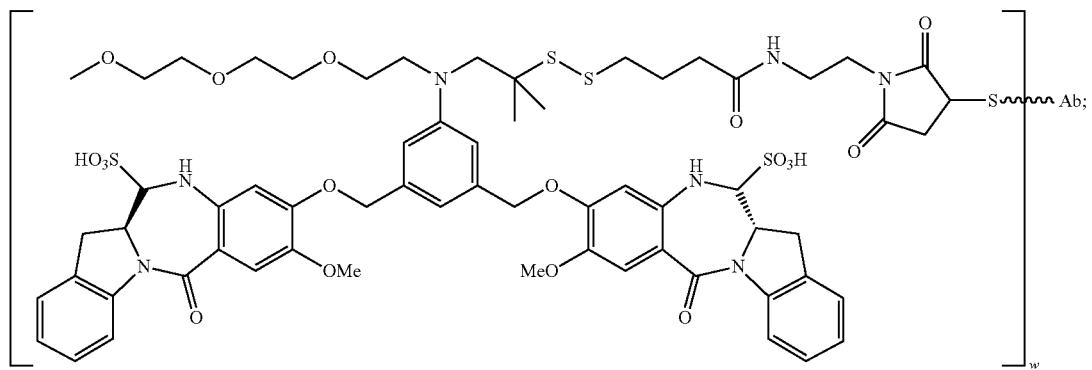

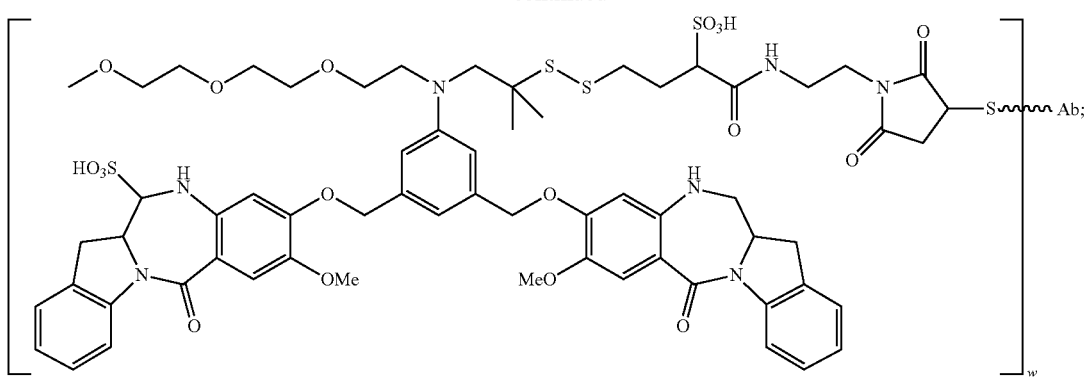
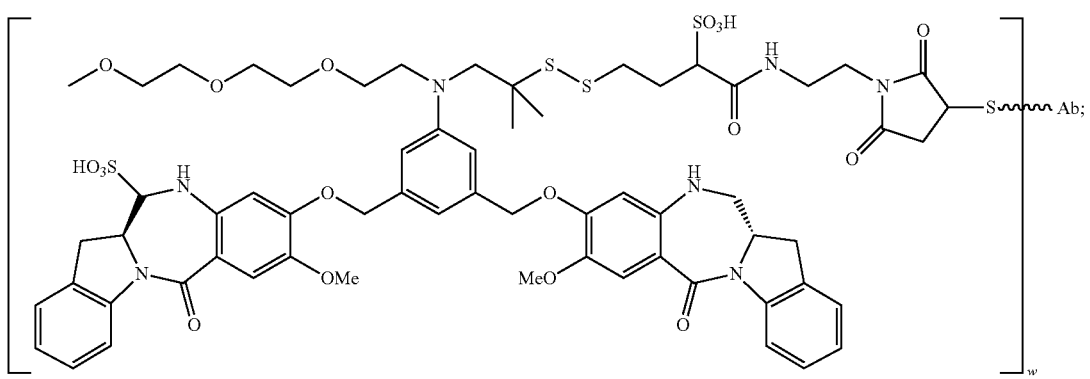
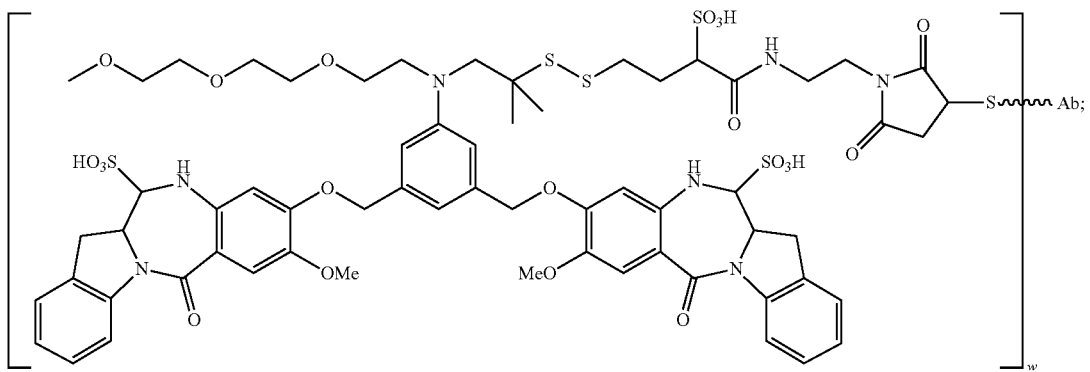
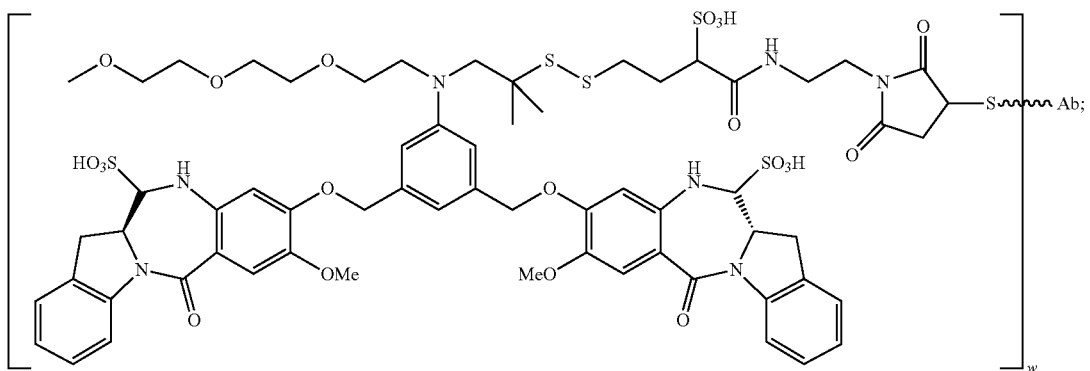

-continued
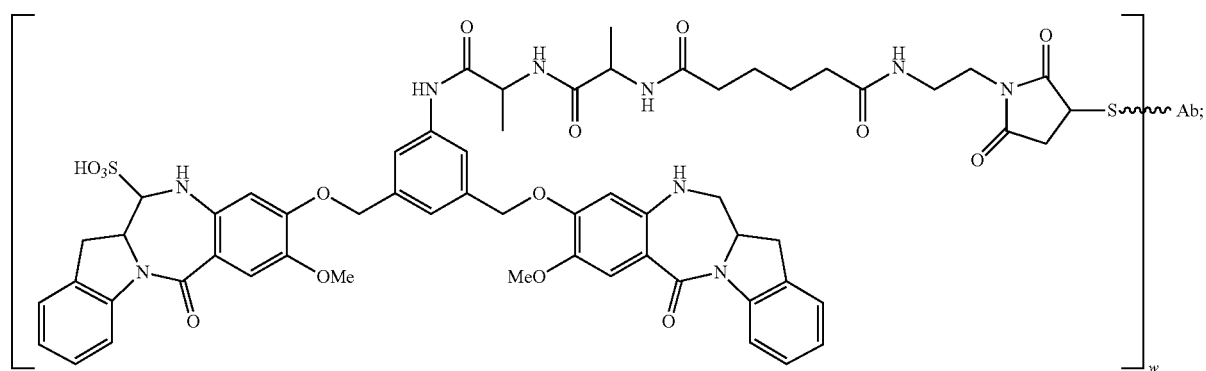
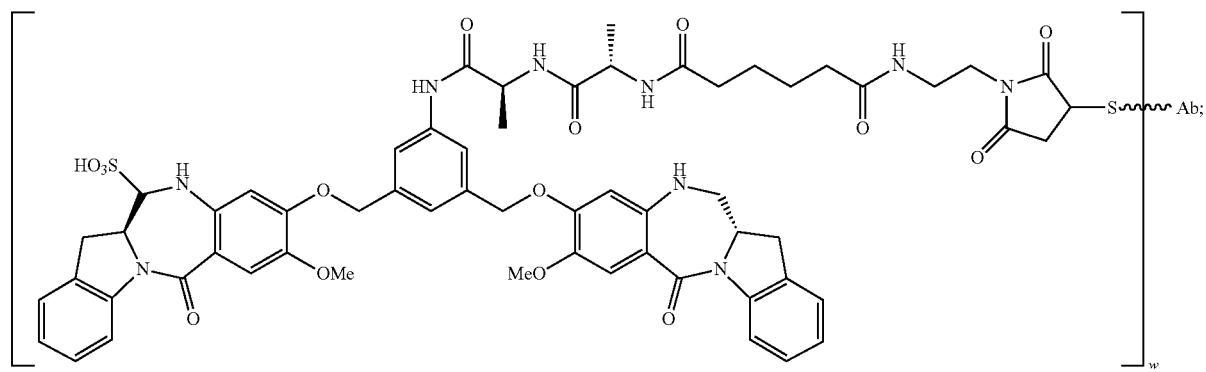
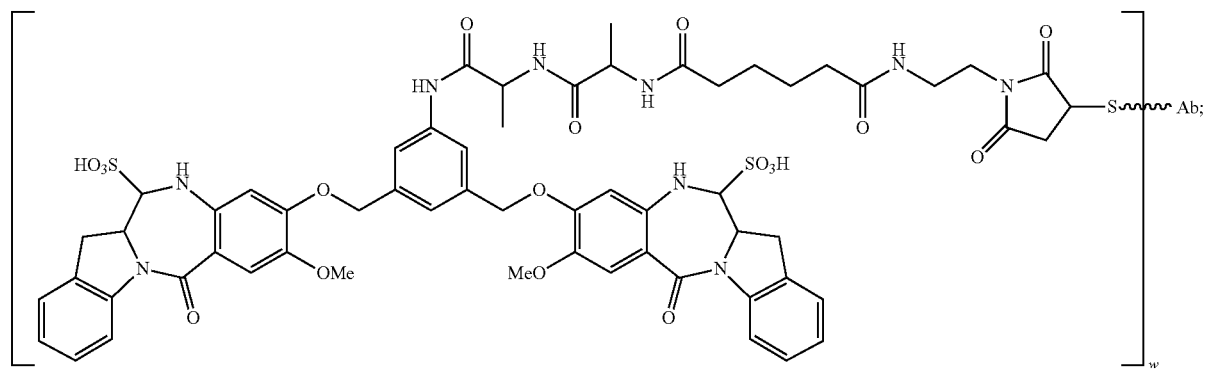
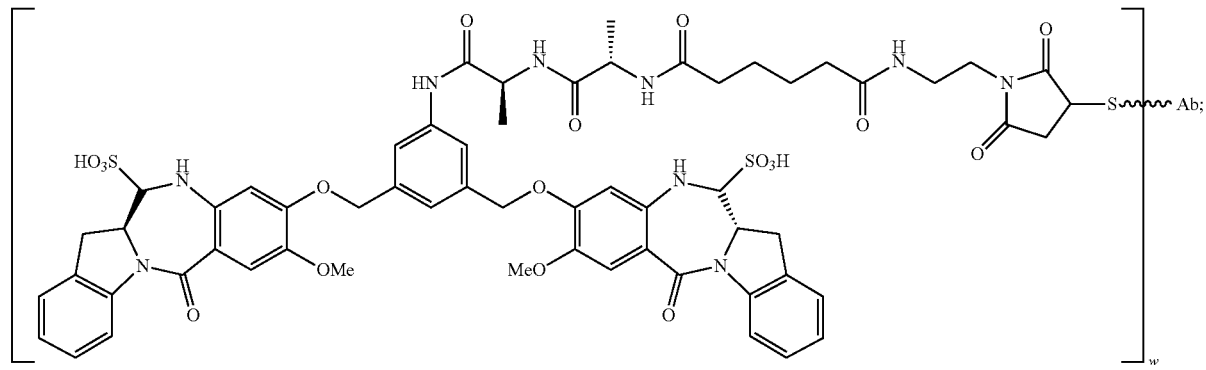

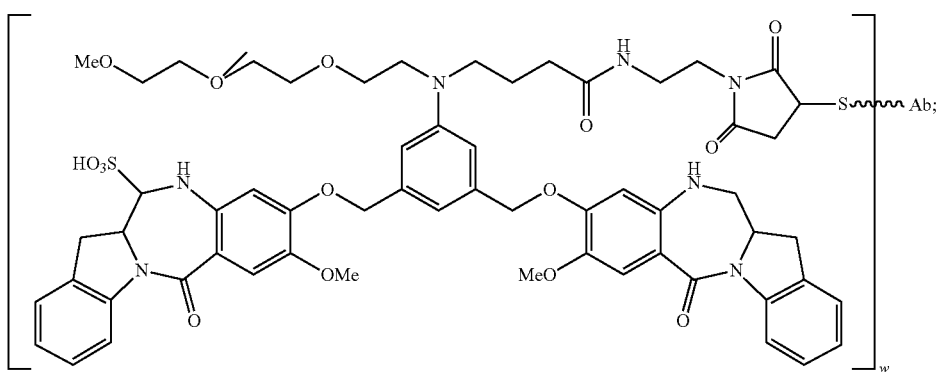
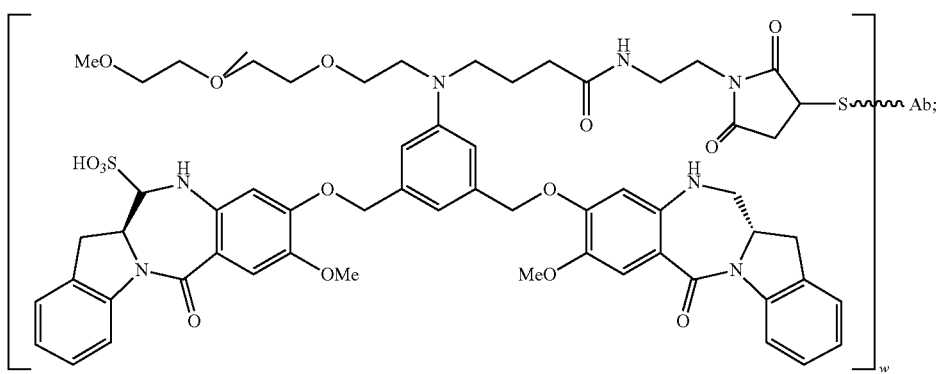
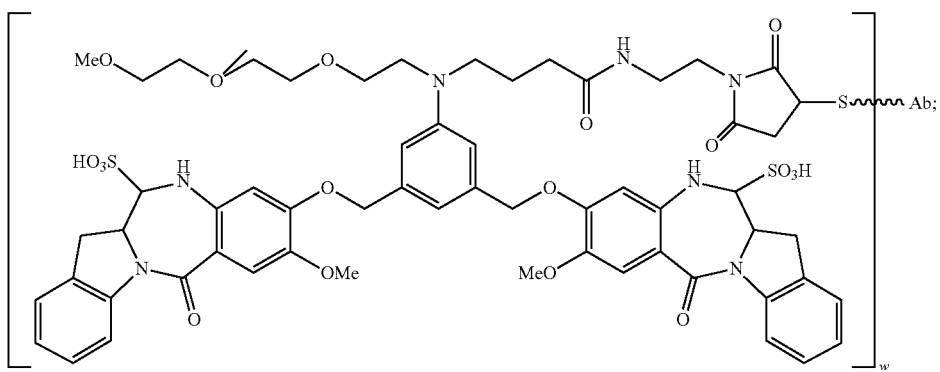
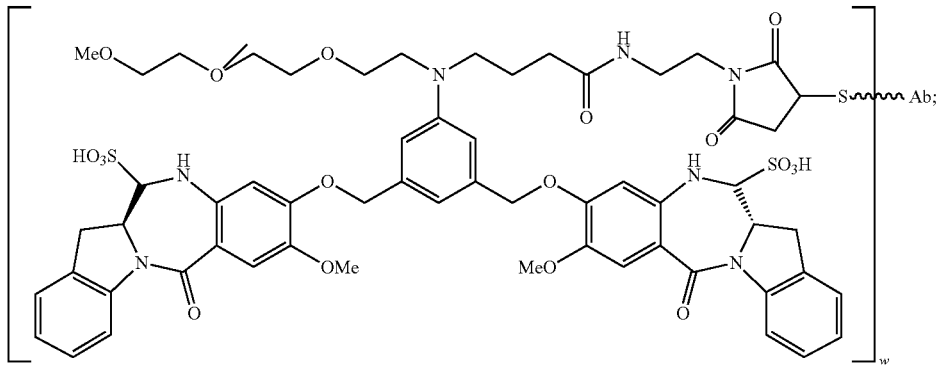

-continued
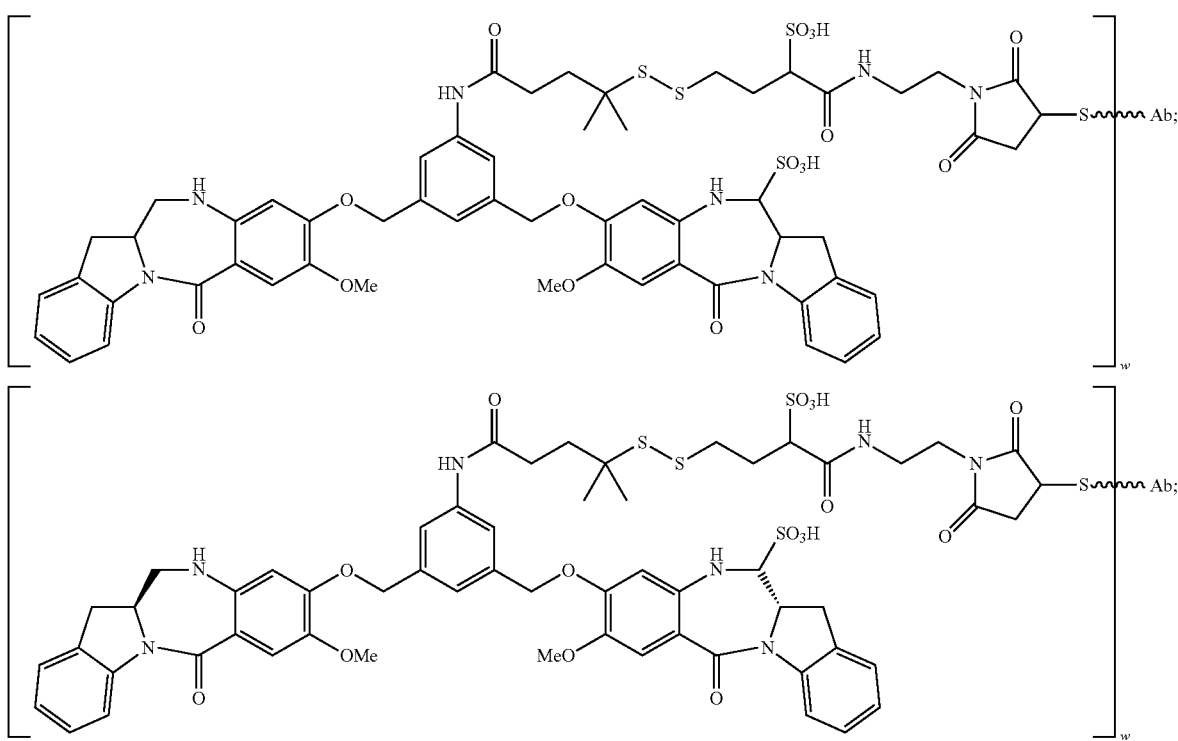
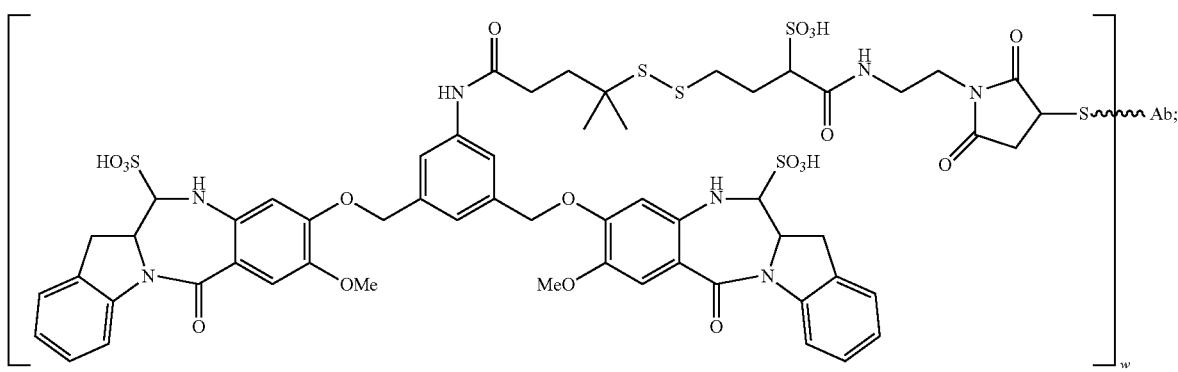
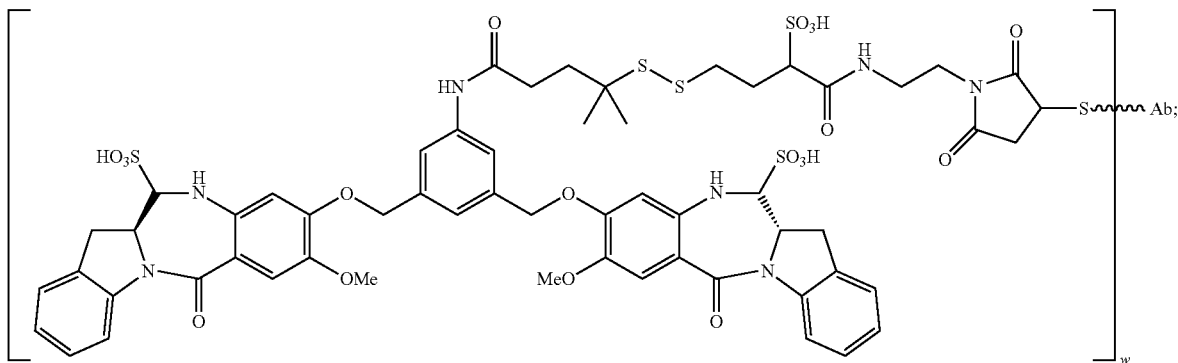

-continued

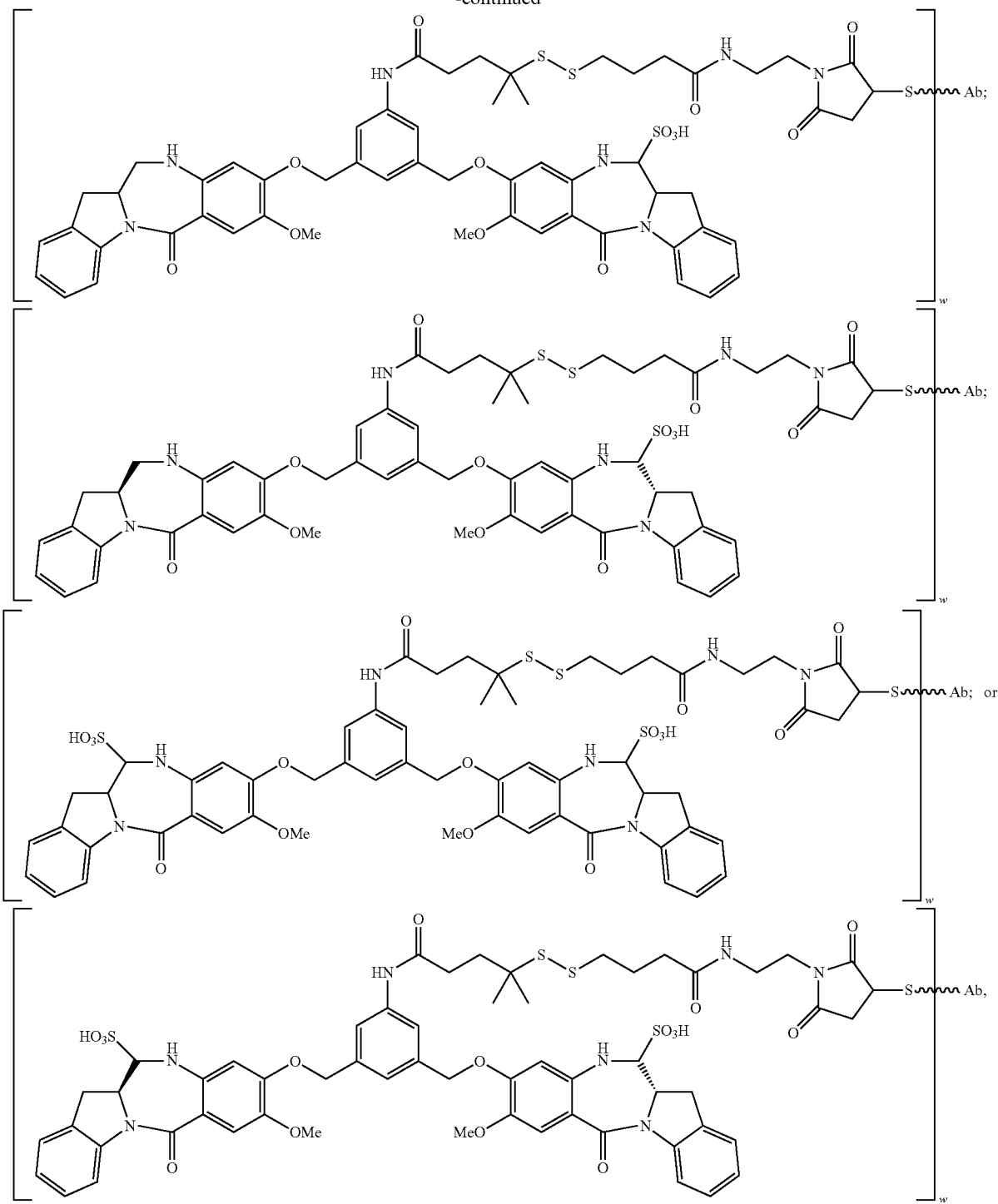

or a pharmaceutically acceptable salt (e.g., sodium or potassium salt) thereof.

In one aspect, for the imine-containing cytotoxic agent of formula (A) or the conjugate of formula (B), D is an imine-containing PBD compound.

In a 25th specific aspect, for the imine-containing cytotoxic agent of formula (A) or the conjugate of formula (B), D is represented by the following formula:

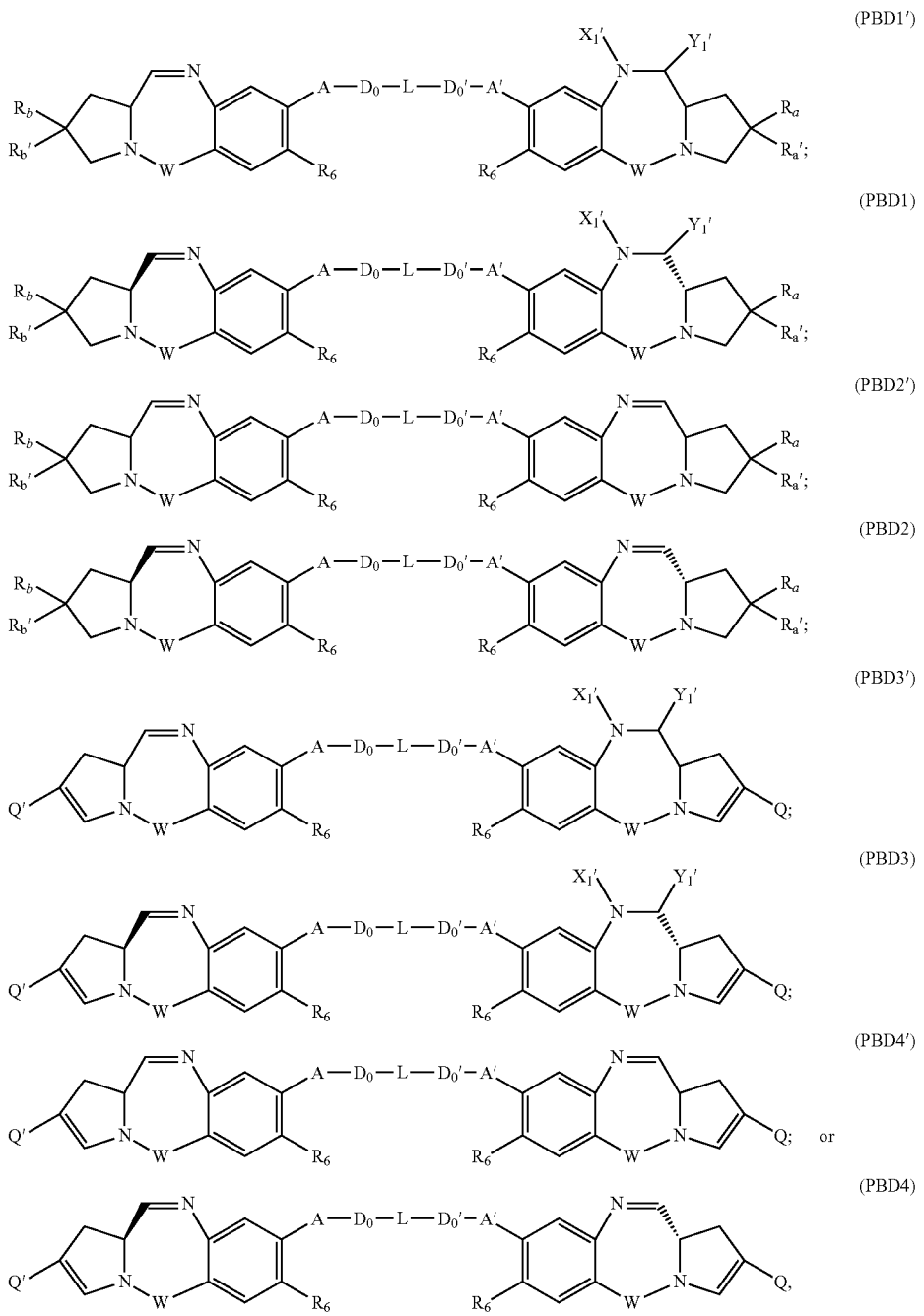

or a pharmaceutically acceptable salt thereof, wherein:

W is selected from C=O, C=S, CH$_2$, BH, SO and SO$_2$;

X$_1$' is selected from —H, an amine-protecting group, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y$_1$' is selected from —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms;

R$_6$ is —H, —R, —OR, —SR, —NR'R", —NO$_2$, or halogen;

A and A' are the same or different, and are independently selected from —O—, oxo (—C(=O)—), —CRR'O—, —CRR'—, —S—, —CRR'S—, —NR₅ and —CRR'N(R₅)—, R, for each occurrence, is independently selected from the group consisting of —H, an optionally substituted linear, branched or cyclic alkyl, alkenyl or alkynyl having from 1 to 10 carbon atoms, a polyethylene glycol unit —(CH₂CH₂O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —NR₂, —COR, an optionally substituted linear, branched or cyclic alkyl, alkenyl or alkynyl having from 1 to 10 carbon atoms, a polyethylene glycol unit —(CH₂CH₂O)$_n$—R$^c$, and an optionally substituted 3- to 18-membered heterocyclic ring having 1 to 6 heteroatoms independently selected from O, S, N and P;

R$^c$ is —H or a substituted or unsubstituted linear or branched alkyl having 1 to 4 carbon atoms, or the linking group with the reactive group bonded thereto;

n is an integer from 1 to 24;

R₅ for each occurrence is independently —H or an optionally substituted linear or branched alkyl having 1 to 10 carbon atoms;

D₀ and D₀' are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—OCH₂CH₂)$_n$—;

L is absent, a linker, a polyethylene glycol unit (—OCH₂CH₂)$_n$—, an optionally substituted linear, branched or cyclic alkyl or alkenyl having 1 to 10 carbon atoms, an optionally substituted phenyl group, an optionally substituted 3 to 18-membered heterocyclic ring or a 5- to 18-membered heteroaryl ring having 1 to 6 heteroatoms independently selected from O, S, N and P;

R$_a$, R$_{a'}$, R$_b$ and R$_{b'}$ are the same or different, and are independently selected from the group consisting of —H, halide, or an optionally substituted branched, linear or cyclic alkyl having 1 to 10 carbon atoms; or R$_a$ and R$_{a'}$, and/or R$_b$ and R$_{b'}$ together form a double bond containing group =B and =B' respectively;

=B and =B' are the same or different and independently selected from an optionally substituted branched or linear alkenyl or a carbonyl group;

Q is Q₁-Ar-Q₂;

Q' is Q₁'-Ar'-Q₂';

Q₁ and Q₁' are each independently absent, a linear, branched or cyclic alkyl from 1 to 6 carbon atoms or a —CH=CH unit;

Ar and Ar' are each independently absent, or represent an aryl group;

Q₂ and Q₂' are each independently selected from —H, a linker, a substituted or unsubstituted linear, branched or cyclic alkyl, alkenyl or alkynyl having from 1 to 10 carbon atoms, a polyethylene glycol unit —R$^c$—(OCH₂CH₂)$_n$—R$^c$, or a substituent selected from a halogen, guanidinium [—NH(C=NH)NH₂], —R, —OR, —NR'R", —NO₂, —NCO, —NR'COR", —NR'(C=O)OR", —SR, a sulfoxide represented by —SOR', a sulfone represented by —SO₂R', a sulfonate —SO₃M, a sulfate —OSO₃M, a sulfonamide represented by SO₂NR'R", cyano, an azido, —COR', —OCOR' or —OCONR'R"; and R$^{c'}$ is absent or selected from linear or branched alkyl, alkenyl or alkynyl having 1 to 5 carbon atoms.

In a 26$^{th}$ specific aspect, for the imine-containing cytotoxic agent of formula (A) or the conjugate of formula (B), D is selected from one of the following:

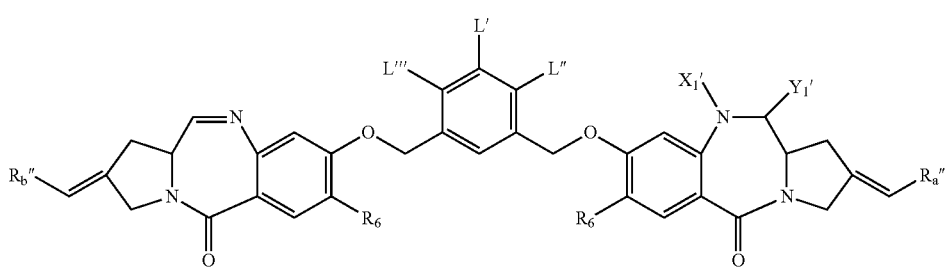

(PBD5')

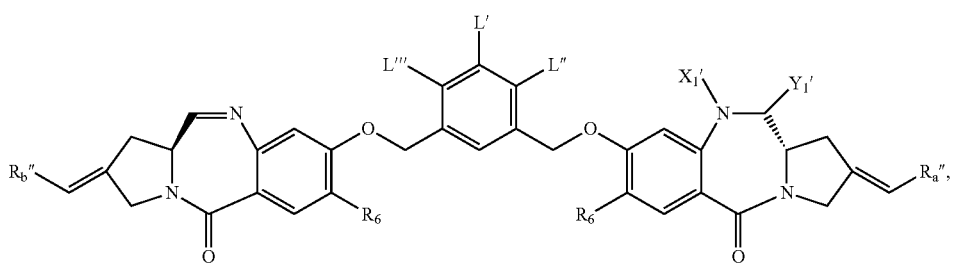

(PBD5)

-continued
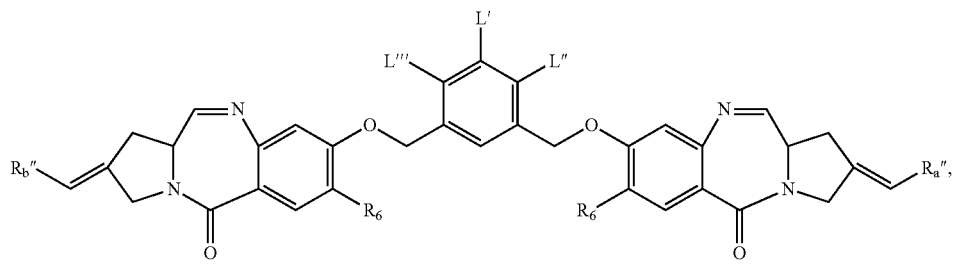
(PBD6′)
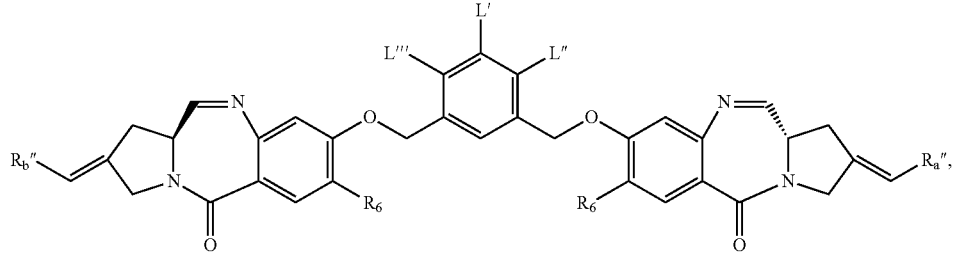
(PBD6)
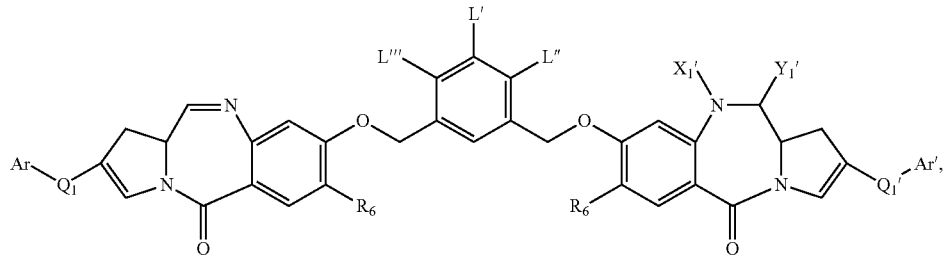
(PBD7′)
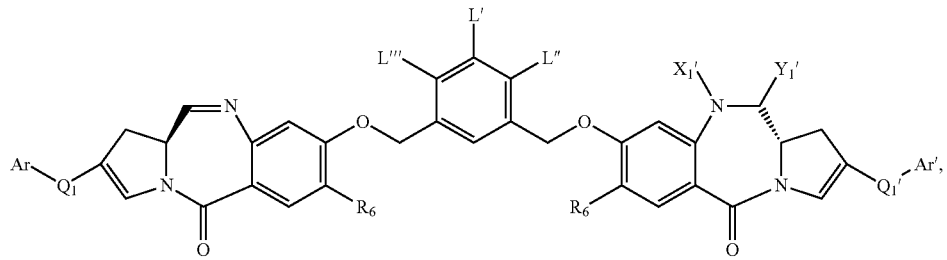
(PBD7)
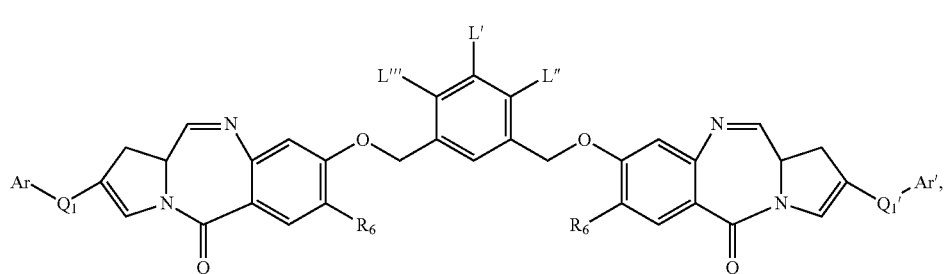
(PBD8′)
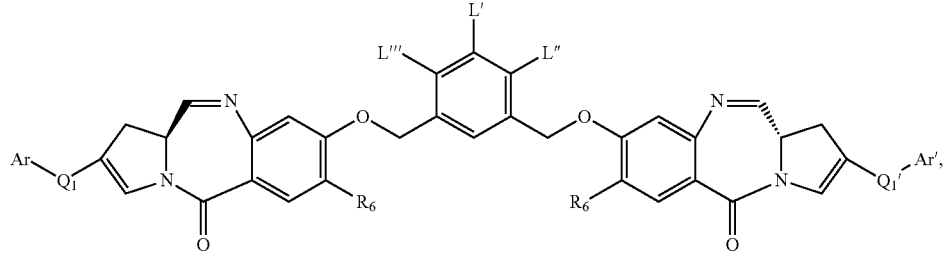
(PBD8)

-continued

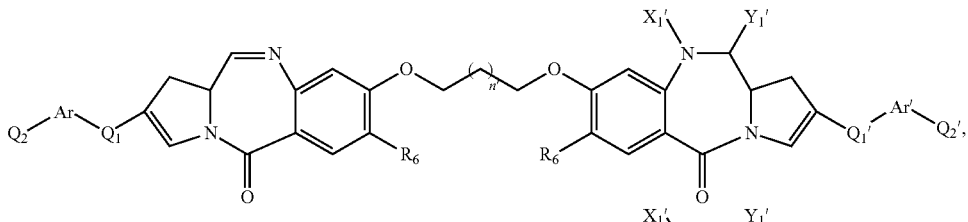
(PBD9')

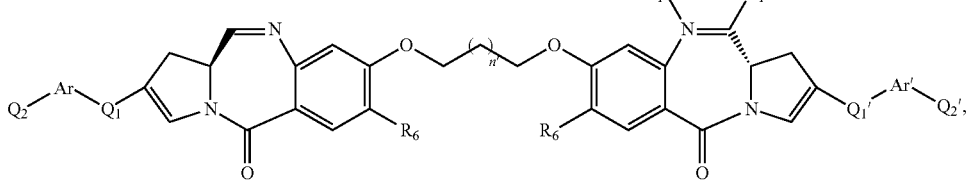
(PBD9)

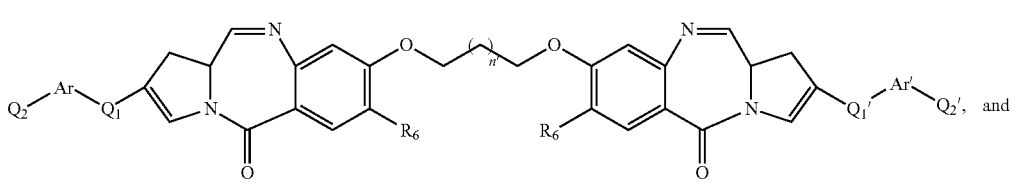
(PBD10')

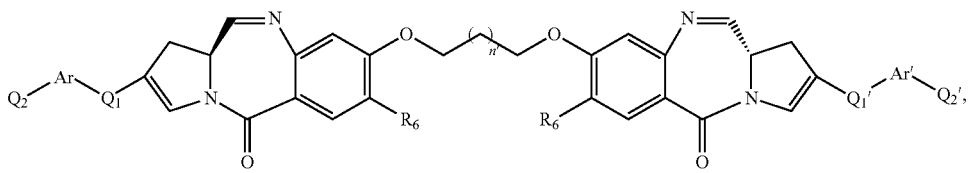
(PBD10)

or a pharmaceutically acceptable salt thereof, wherein:

one of L', L", and L'" in formula (PBD5'), (PBD6'), (PBD7'), (PBD8'), (PBD5), (PBD6), (PBD7) or (PBD8) is represented by the following formula:

 (A'), or

 (D');

and the other two are each independently selected from —H, an optionally substituted linear, branched or cyclic alkyl, alkenyl or alkynyl having 1 to 10 carbon atoms, a polyethylene glycol unit —(CH$_2$CH$_2$O)$_n$—R$^c$, halogen, guanidinium [—NH(C═NH)NH$_2$], —OR, —NR'R", —NO$_2$, —NR'COR", —SR, —SOR', —SO$_2$R', —SO$_3$H, —OSO$_3$H, —SO$_2$NR'R", cyano, an azido, —COR', —OCOR', and —OCONR'R";

one of Q$_2$ and Q$_2$' in formula (PBD9'), (PBD10'), (PBD9) or (PBD10) is represented by the following formula:

 (A'),

 (D'); or

 (E'), and the other one is selected from —H, —R, —OR, —NR'R", —NO$_2$, —NR'(C═O)OR", —SR, or —NO$_2$;

one of the Z$_1$ and Z$_2$ is —C(═O)—, and the other is —NR$_5$—;

P$_1$ is an amino acid residue or a peptide containing between 2 to 20 amino acid residues;

R$_{x1}$ is an optionally substituted linear, branched or cyclic alkyl, alkenyl or alkynyl having from 1 to 10 carbon atoms;

R$^e$ is —H, a linear, branched or cyclic alkyl, alkenyl or alkynyl having 1 to 10 carbon atoms or —(CH$_2$—CH$_2$—O)$_n$—R$^k$, wherein R$^k$ is a —H, a linear, branched cyclic alkyl having 1 to 6 carbon atoms, optionally bearing a secondary amino (e.g., —NHR$^{101}$) or tertiary amino (—NR$^{101}$R$^{102}$) group or a 5- or 6-membered nitrogen containing heterocycle, wherein R$^{101}$ and R$^{102}$ are each independently a linear, branched, or cyclic alkyl, alkenyl or alkynyl having 1 to 10 carbon atoms;

R$^c$ is —H or an optionally substituted linear or branched alkyl having 1 to 4 carbon atoms;

R$_5$ for each occurrence is independently —H or an optionally substituted linear or branched alkyl having 1 to 10 carbon atoms.

R$_a$" and R$_b$" are the same or different, and are selected from —H and -Me; and n' is selected from 0, 1, 2 and 3; and the remaining variables are as described in the 25$^{th}$ specific aspect.

In a 27$^{th}$ specific aspect, one of L', L" and L'" in formula (PBD5'), (PBD6'), (PBD7'), (PBD8'), (PBD5), (PBD6), (PBD7) or (PBD8) is represented by formula (A') or (D') and the other two are —H, an linear or branched alkyl having from 1 to 6 carbon atoms, halogen, —OH, (C$_1$-C$_6$)alkoxy or —NO$_2$; or one of Q$_2$ and Q$_2$' in formula (PBD9'), (PBD10'), (PBD9) or (PBD10) is represented by formula (A'), (D') or (E'); and the other is —H, an linear or branched alkyl having from 1 to 6 carbon atoms, halogen, —OH, (C$_1$-C$_6$)alkoxy or —NO$_2$; and the remaining variables are as described in the 26$^{th}$ specific aspect.

In a 28th specific aspect, L″ and L‴ are both —H; and L′ in formula (PBD5′), (PBD6′), (PBD7′), (PBD8′), (PBD5), (PBD6), (PBD7) or (PBD8) is represented by the following formula:

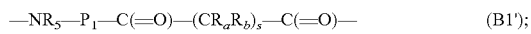  (B1′);

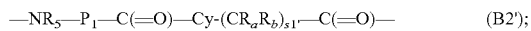  (B2′);

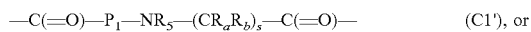  (C1′), or

  (C2′);

one of $Q_2$ and $Q_2'$ in formula (PBD9′), (PBD 10′), (PBD9) or (PBD10) is represented by the following formula:

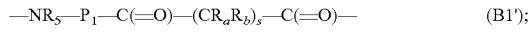  (B1′);

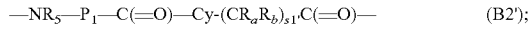  (B2′);

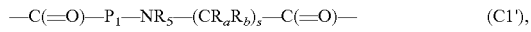  (C1′),

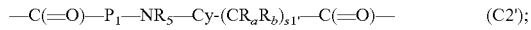  (C2′);

  (E1′); or

  (E2′);

wherein:

$R_a$ and $R_b$, for each occurrence, are each independently —H, ($C_1$-$C_3$)alkyl or a charged substituent or an ionizable group Q;

s is an integer from 1 to 6;

s1′ is 0 or an integer from 1 to 6; and

Cy is a cyclic alkyl having 5 or 6 ring carbon atoms optionally substituted with halogen, —OH, ($C_1$-$C_3$)alkyl, ($C_1$-$C_3$)alkoxy, or halo($C_1$-$C_3$)alkyl; and the remaining variables are as described in the 27th specific aspect. In some embodiments, $R_a$ and $R_b$ are both H; Cy in formulas (B2′) and (C2′) is cyclohexane; $R_5$ is H or Me; and s1′ is 0 or 1.

In a 29th specific aspect, $P_1$ is a peptide containing 2 to 10 amino acid residues; and the remaining variables are as described in the 28th specific aspect. In some embodiments, $P_1$ is a peptide containing 2 to 5 amino acid residues. In some embodiments, $P_1$ is Gly-Gly-Gly, Ala-Val, Val-Cit, Val-Lys, Phe-Lys, Lys-Lys, Ala-Lys, Phe-Cit, Leu-Cit, Ile-Cit, Trp, Cit, Phe-Ala, Phe-$N^9$-tosyl-Arg, Phe-$N^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 1), β-Ala-Leu-Ala-Leu (SEQ ID NO: 2), Gly-Phe-Leu-Gly (SEQ ID NO: 3), Val-Arg, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, Gln-Val, Asn-Ala, Gln-Phe and Gln-Ala. In some embodiments, $P_1$ is Gly-Gly-Gly, Ala-Val, Ala-Ala, Ala-D-Ala, D-Ala-Ala, or D-Ala-D-Ala.

In a 30th specific aspect, for the methods described in any one of the 25th, 26th, 27th, 28th or 29th specific aspect and embodiments described therein, $R_6$ is —OMe; $X_1'$ and $Y_1'$ are both —H; and A and A′ are —O—.

In a 31st specific aspect, for the imine-containing cytotoxic agent of formula (A) or the conjugate of formula (B), D is represented by the following structural formula:

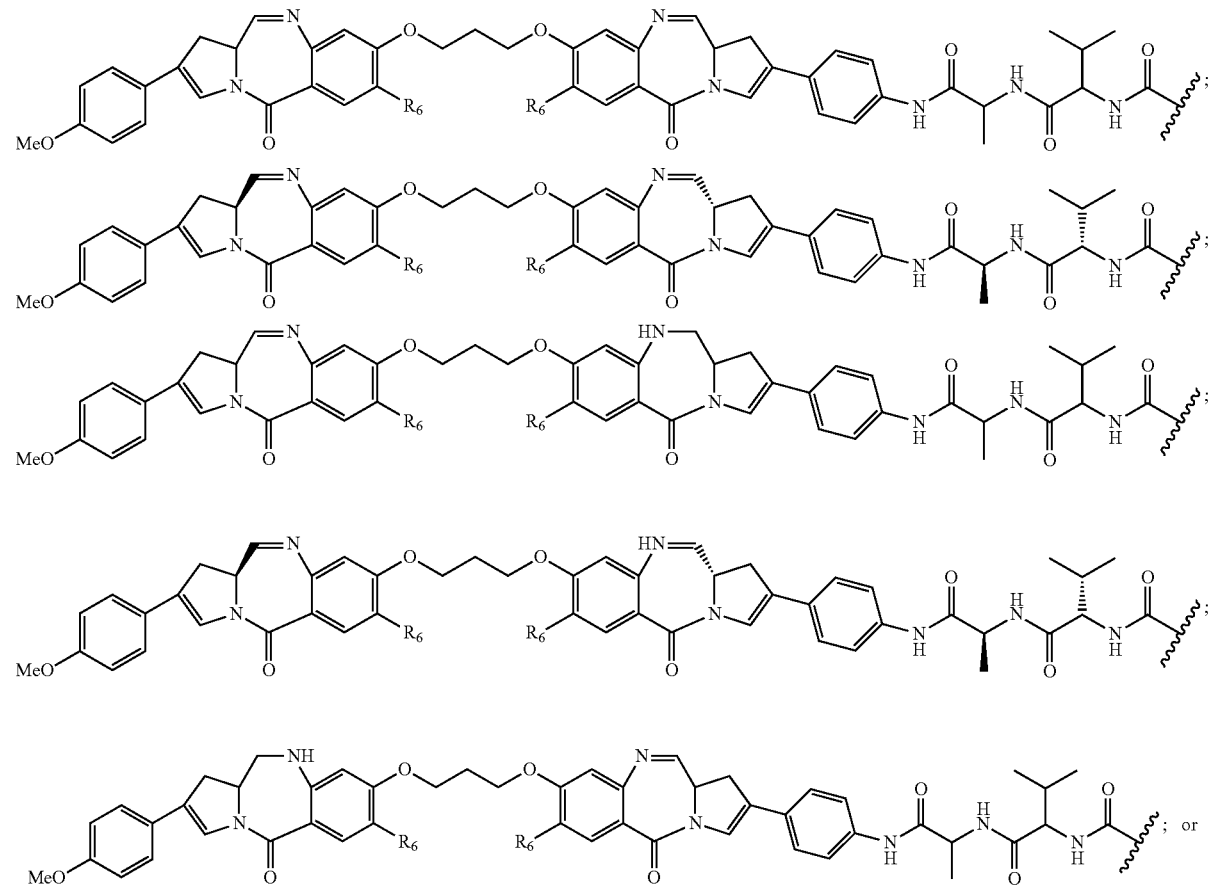

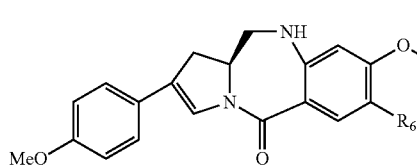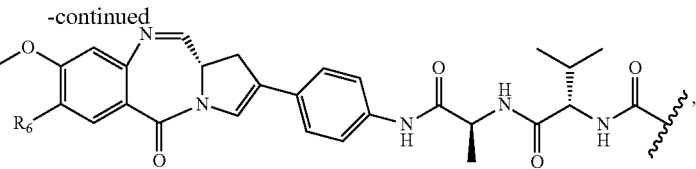

or a pharmaceutically acceptable salt thereof.

In a 32$^{nd}$ specific aspect, for the imine-containing cytotoxic agent of formula (A) or the conjugate of formula (B), -L- is represented by the following structural formula:

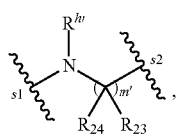

or a pharmaceutically acceptable salt thereof, wherein:
s1 is the site covalently linked to D; s2 is the site covalently linked to the maleimide group;
$R_{23}$ and $R_{24}$, for each occurrence, are independently H or an optionally substituted alkyl;
m' is an integer between 0 and 10; and
$R^{h'}$ is H or an optionally substituted alkyl; and the remaining variables are as describe above in the 25$^{th}$, 26$^{th}$, 27$^{th}$, 28$^{th}$, 29$^{th}$, 30$^{th}$, 31$^{st}$ or 32$^{nd}$ specific aspect.

In some embodiments, $R_{23}$ and $R_{24}$ are both H; and m' is an integer between 1 and 6.

In some embodiments, $R^{h'}$ is H.

In some embodiments, L is represented by the following structural formula:

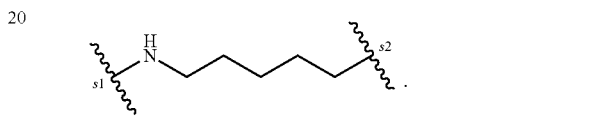

In a 34$^{th}$ specific aspect, the imine-containing cytotoxic agent is represented by the following formula:

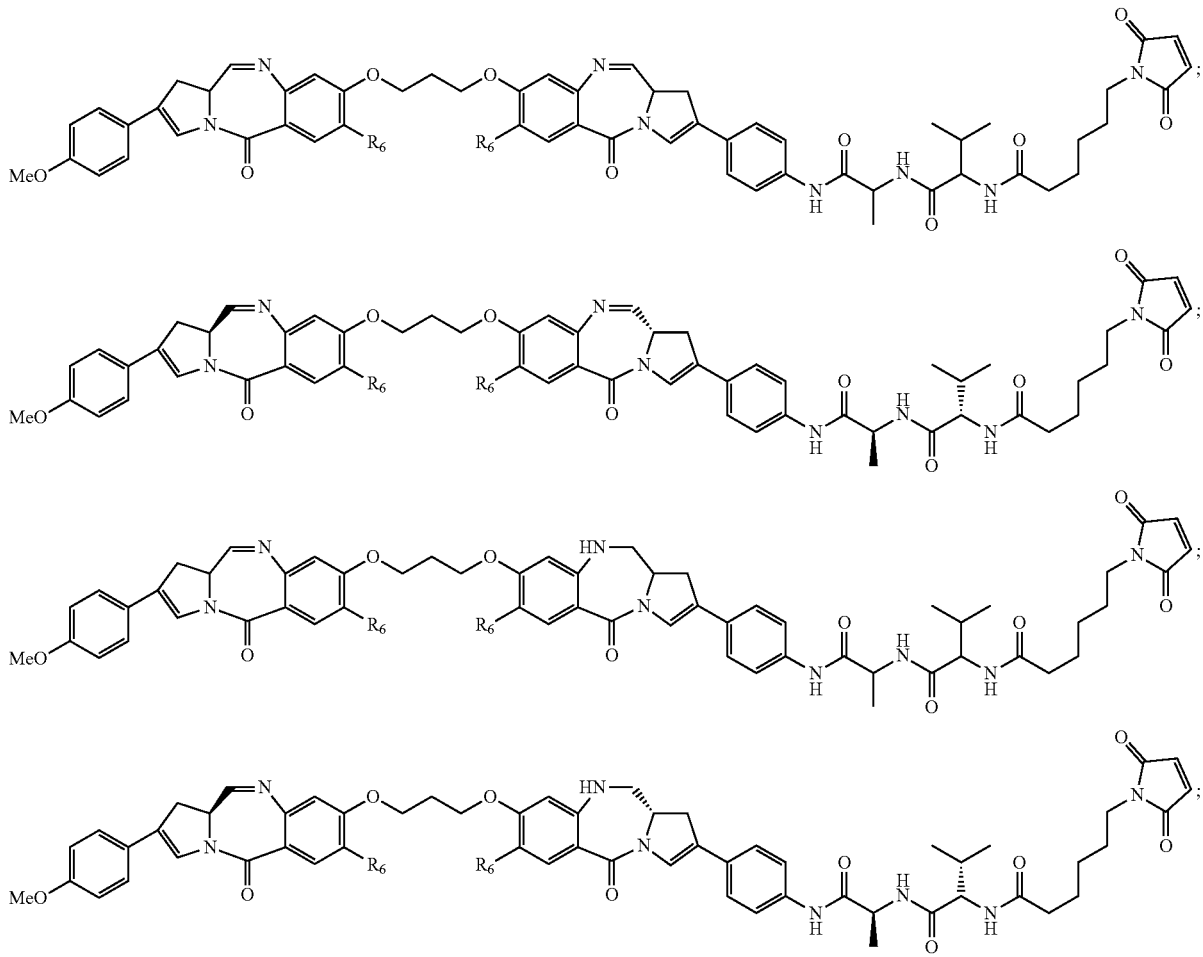

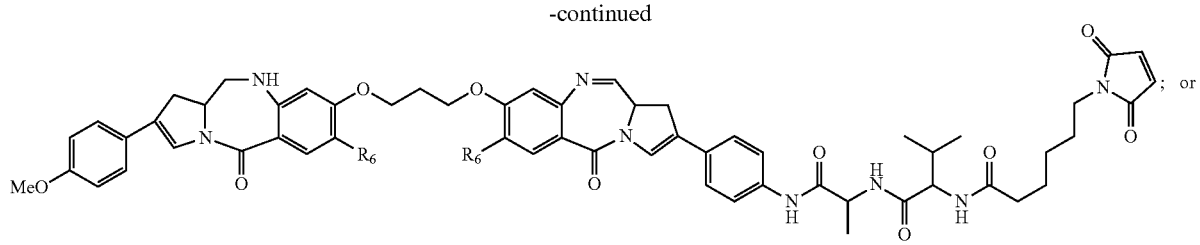

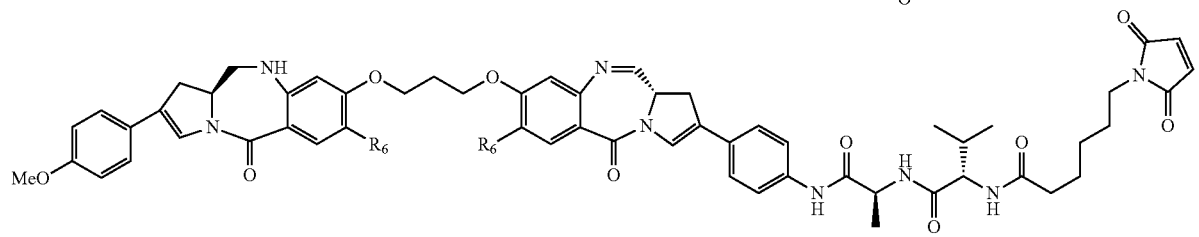

20 or a pharmaceutically acceptable salt thereof.

In some embodiments, the imine-containing cytotoxic agent is represented by the following formula:

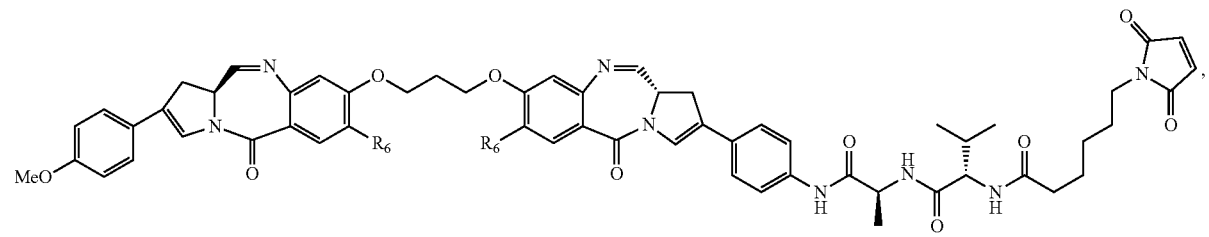

or a pharmaceutically acceptable salt thereof; the modified imine-containing cytotoxic agent is represented by the following formula:

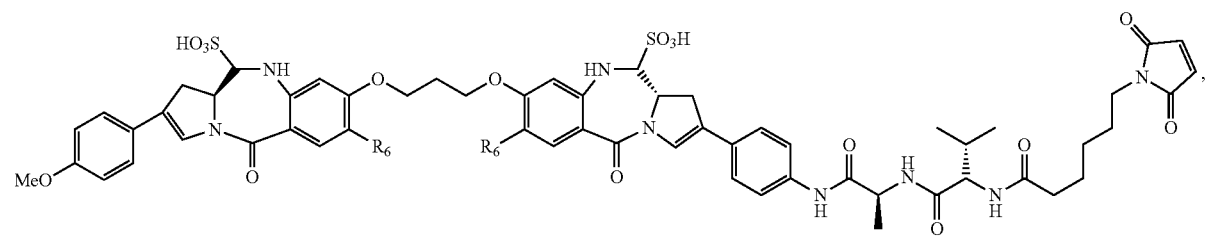

or a pharmaceutically acceptable salt thereof; and the conjugate is represented by the following formula:

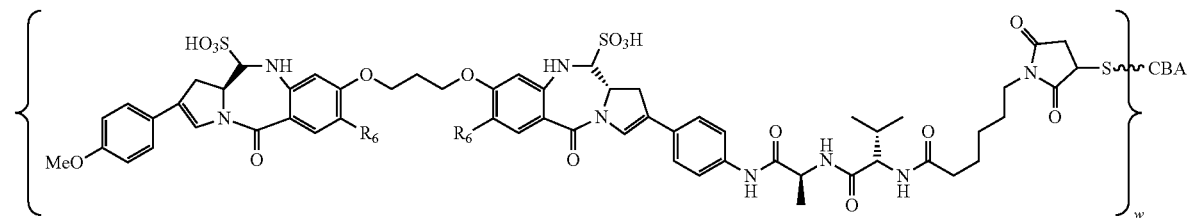

or a pharmaceutically acceptable salt thereof.

In a 35th specific aspect, for the imine-containing cytotoxic agent of formula (A) or the conjugate of formula (B), D is represented by the following formula:
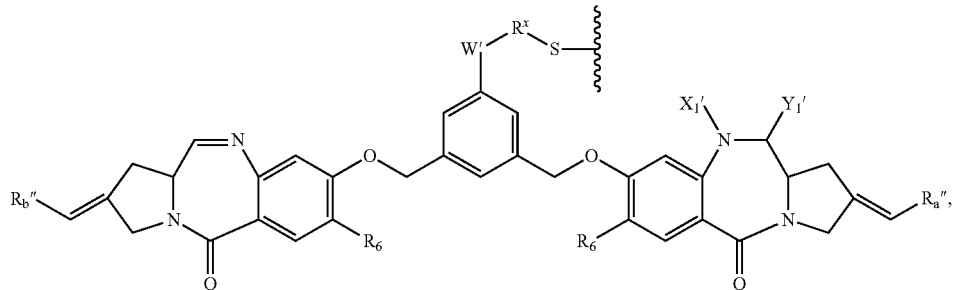
(PBD11')
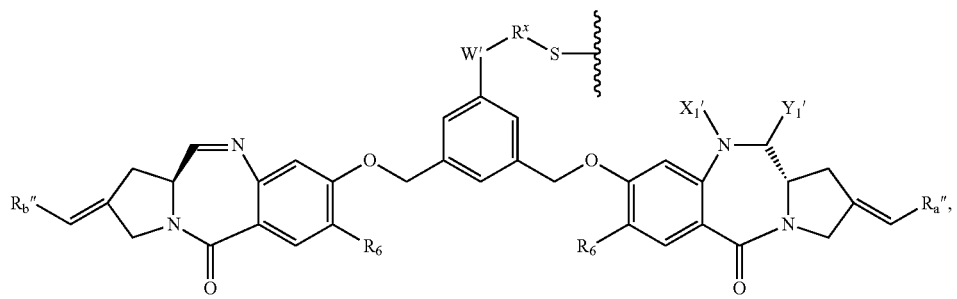
(PBD11)
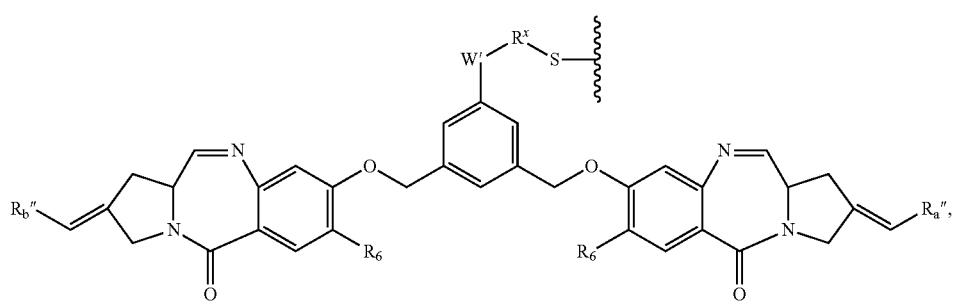
(PBD12')
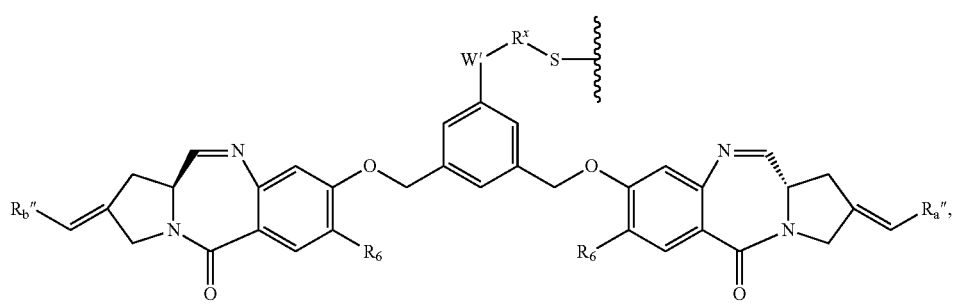
(PBD12)
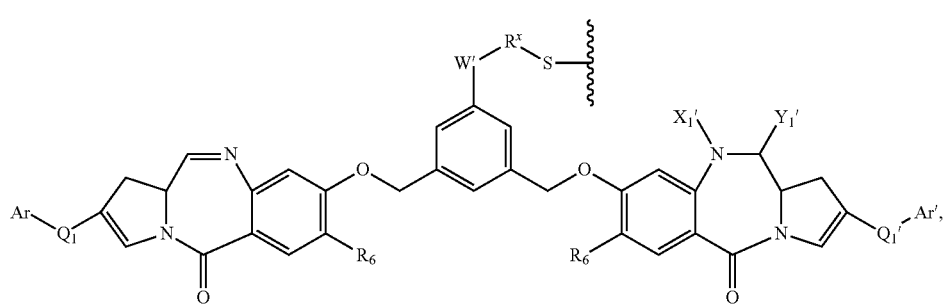
(PBD13')

-continued
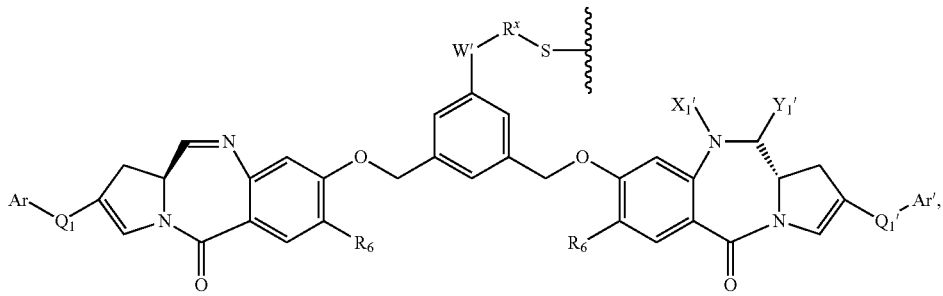
(PBD13)
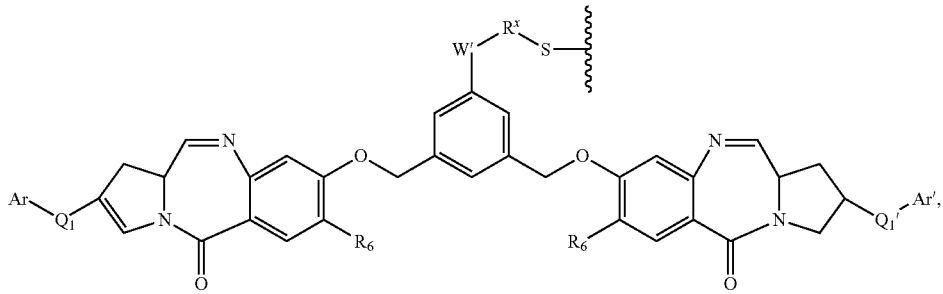
(PBD14′)
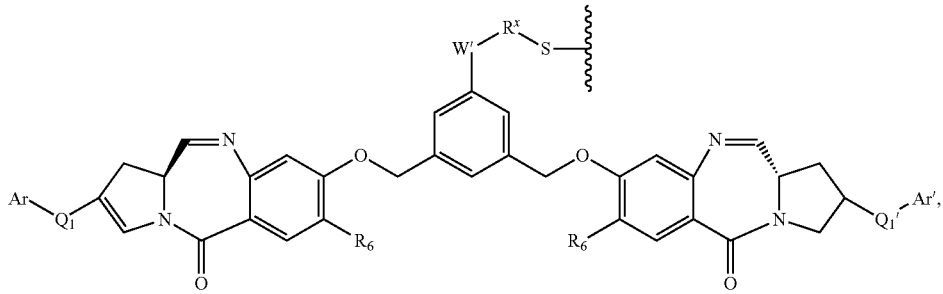
(PBD14)
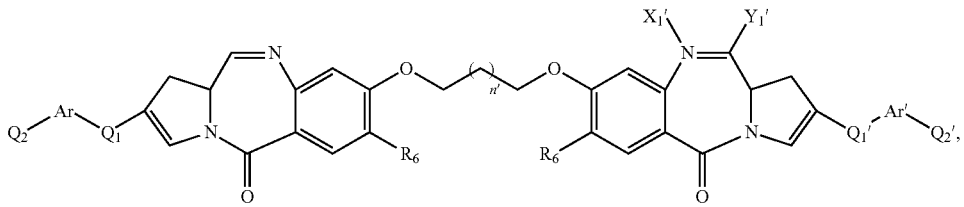
(PBD15′)
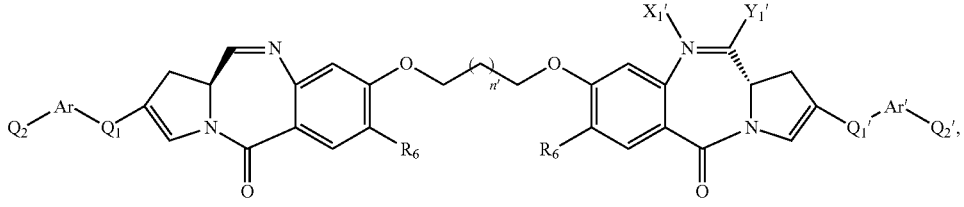
(PBD15)
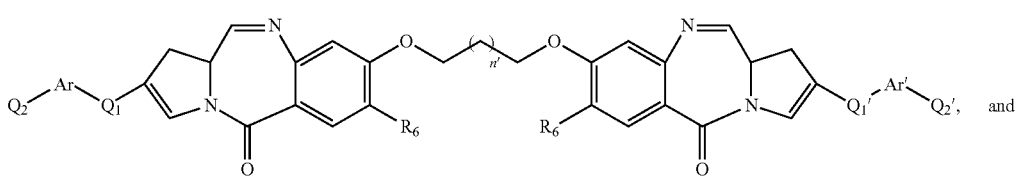
(PBD16′)
and (PBD16)

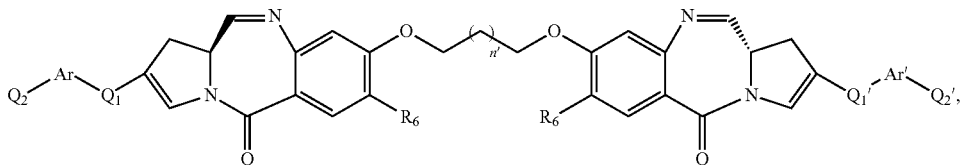

or a pharmaceutically acceptable salt thereof, wherein:

$X_1'$ is selected from the group consisting of —H, —OH, a substituted or unsubstituted linear, branched or cyclic alkyl, alkenyl or alkynyl having from 1 to 10 carbon atoms, phenyl, and an amine-protecting group;

$Y_1'$ is selected from the group consisting of —H, an oxo group, a substituted or unsubstituted linear, branched or cyclic alkyl, alkenyl or alkynyl having from 1 to 10 carbon atoms;

one of $Q_2$ and $Q_2'$ in formula (PBD15) or (PBD16) is —W'—$R^x$—S—; and the other is selected from —H, an optionally substituted linear, branched or cyclic alkyl, alkenyl or alkynyl having from 1 to 10 carbon atoms, a polyethylene glycol unit —(CH$_2$CH$_2$O)$_n$—$R^c$, halogen, guanidinium [—NH(C=NH)NH$_2$], —OR, —NR'R", —NO$_2$, —NR'COR", —SR, —SOR', —SO$_2$R', —SO$_3$H, —OSO$_3$H, —SO$_2$NR'R", cyano, an azido, —COR', —OCOR', and —OCONR'R";

W' is absent, or selected from —O—, —N($R^e$)—, —N($R^e$)—C(=O)—, —N(C(=O)$R^e$)—, —S— or —CH$_2$—S—, —CH$_2$NR$^e$—;

$R^x$ is absent or selected from a linear, branched or cyclic alkyl having 1 to 10 carbon atoms;

$R^e$ is —H, a linear, branched or cyclic alkyl, alkenyl or alkynyl having 1 to 10 carbon atoms or —(CH$_2$—CH$_2$—O)$_n$—$R^k$, wherein $R^k$ is a —H, a linear, branched cyclic alkyl having 1 to 6 carbon atoms, optionally bearing a secondary amino (e.g., —NHR$^{101}$) or tertiary amino (—NR$^{101}$R$^{102}$) group or a 5- or 6-membered nitrogen containing heterocycle, wherein R$^{101}$ and R$^{102}$ are each independently a linear, branched, or cyclic alkyl, alkenyl or alkynyl having 1 to 10 carbon atoms;

n is an integer from 1 to 24;

$R_6$ is —H, —R, —OR, —SR, —NR'R", —NO$_2$, or halogen; and

R is —H, an optionally substituted linear, branched or cyclic alkyl, alkenyl or alkynyl having from 1 to 10 carbon atoms or a PEG group —(CH$_2$CH$_2$O)$_n$—$R^c$, wherein n is an integer from 1 to 24, and $R^c$ is a linear or branched alkyl having 1 to 4 carbon atoms;

R' and R" are each independently selected from —H, —OH, —OR, —NRR$^{g'}$, —COR, an optionally substituted linear, branched or cyclic alkyl, alkenyl or alkynyl having from 1 to 10 carbon atoms, an optionally substituted aryl having from 6 to 18 carbon atoms, an optionally substituted 3- to 18-membered heterocyclic ring having 1 to 6 heteroatoms selected from O, S, N and P, a PEG group —(CH$_2$CH$_2$O)$_n$—$R^c$, and $R^{g'}$ is —H, an optionally substituted linear, branched or cyclic alkyl, alkenyl or alkynyl having from 1 to 10 carbon atoms or a PEG group —(CH$_2$CH$_2$O)$_n$—$R^c$.

In a 36$^{th}$ specific aspect, for formula (PBD11'), (PBD12'), (PBD13'), (PBD14'), (PBD15'), (PBD16'), (PBD11), (PBD12), (PBD13), (PBD14), (PBD15) or (PBD16), $X_1'$ and $Y_1'$ are both —H;

$R_6$ is —OMe;

W' is —N($R^e$)— or —N($R^e$)—C(=O)—;

$R^e$ is —H, a linear or branched alkyl having 1 to 4 carbon atoms or —(CH$_2$—CH$_2$—O)$_n$—$R^k$, wherein $R^k$ is a —H, a linear or branched alkyl having 1 to 4 carbon atoms;

n is an integer from 2 to 6; and $R^x$ is a linear or branched alkyl having 1 to 6 carbon atoms; and the remaining variables are as described in the 35$^{th}$ specific aspect.

In a 37$^{th}$ specific aspect, for the imine-containing cytotoxic agent of formula (A) or the conjugate of formula (B), L is represented by the following structural formula:

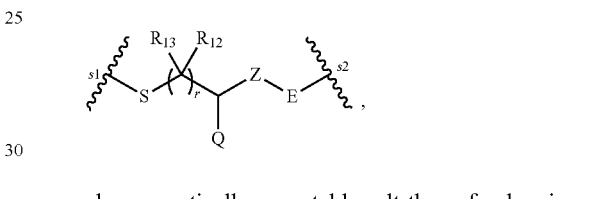

or a pharmaceutically acceptable salt thereof, wherein:

s1 is the site covalently linked to D, and s2 is the site covalently linked to the maleimide group;

E is —(CR$^{10}$R$^{11}$)$_q$—, cycloalkyl, or cycloalkylalkyl;

Z is absent, —SO$_2$NR$_9$—, —NR$_9$SO$_2$—, —C(=O)—NR$_9$—, —NR$_9$—C(=O)—, —C(=O)—O—, —O—C(=O)—, —C(=O)—NR$_9$—(CH$_2$CH$_2$O)$_p$—, —NR$_9$—C(=O)—(CH$_2$CH$_2$O)$_p$—, —(OCH$_2$CH$_2$)$_p$—C(=O)NR$_9$—, or —(OCH$_2$CH$_2$)$_p$—NR$_9$—C(=O)—;

p is an integer from 1 to 24;

Q is H, a charged substituent, or an ionizable group;

$R_9$, $R_{10}$, $R_{11}$, $R_{12}$, and $R_{13}$, for each occurrence, are independently H or an optionally substituted alkyl; and, q and r, for each occurrence, are independently an integer between 0 and 10; and the remaining variables are as described in the 35$^{th}$ or 36$^{th}$ specific aspect.

In some embodiments, E is —(CR$_{10}$R$_{11}$)$_q$—. In some embodiments, Z is —C(=O)—NR$_9$— or —NR$_9$—C(=O)—. In some embodiments, $R_9$ is —H. In some embodiments, $R_9$, $R_{10}$, $R_{11}$, $R_{12}$, and $R_{13}$ are all H; and q and r are each independently an integer between 1 and 6.

In some embodiments, for -L- described in the 37 specific aspect:

$R_{12}$ and $R_{13}$, for each occurrence, are each independently H or (C$_1$-C$_3$)alkyl;

Q is H or —SO$_3$H or a pharmaceutically acceptable salt thereof;

Z is —C(=O)—NR$_9$— or —NR$_9$—C(=O)—;

$R_9$ is H or (C$_1$-C$_3$)alkyl;

E is —(CR$_{10}$R$_{11}$)$_q$—.

$R_{10}$ and $R_{11}$, for each occurrence, are independently H or (C$_1$-C$_3$)alkyl; and q and r are each an integer from 1 to 5.

In a 38$^{th}$ specific aspect, for the imine-containing cytotoxic agent of formula (A) or the conjugate of formula (B), L is represented by any one of the following structural formulae:

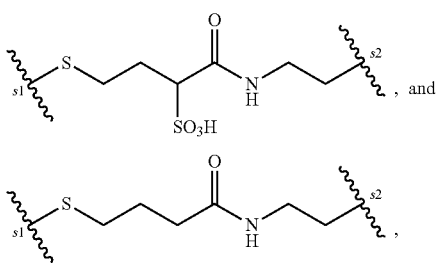

, and tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 1), β-Ala-Leu-Ala-Leu (SEQ ID NO: 2), Gly-Phe-Leu-Gly (SEQ ID NO: 3), Val-Arg, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala., Ala-Met, Met-Ala, Gln-Val, Asn-Ala, Gln-Phe, Gln-Ala, Gly-Gly-Gly, Ala-Ala-Ala, D-Ala-Ala-Ala, Ala-D-Ala-Ala, Ala-Ala-D-Ala, Ala-Val-Cit, Ala-Val-Ala, and β-Ala-Gly-Gly-Gly.

In some embodiments, L is represented by the following structural formula:

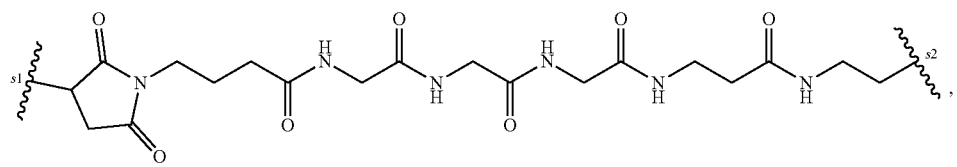

or a pharmaceutically acceptable salt thereof, and the remaining variables are as described in the 35$^{th}$ or 36$^{th}$ specific aspect.

In a 39$^{th}$ specific aspect, for the imine-containing cytotoxic agent of formula (A) or the conjugate of formula (B), L is represented by the following structural formula:

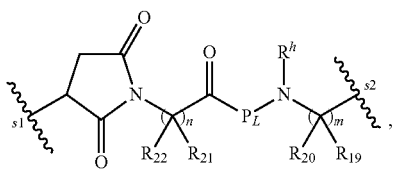

or a pharmaceutically acceptable salt thereof, wherein:

s1 is the site covalently linked to D; s2 is the site covalently linked to the maleimide group;

$R_{19}$, $R_{20}$, $R_{21}$ and $R_{22}$, for each occurrence, are independently H or an optionally substituted alkyl;

m and n are each independently an integer between 0 and 10;

$R^h$ is H or an optionally substituted alkyl;

$P_L$ is an optionally substituted alkylene, —(CH$_2$—CH$_2$—O)$_j$— (wherein the oxygen atom is connected to the —(C=O)— group connected to P), an amino acid residue or a peptide containing 2 to 20 amino acid residues; and j is an integer from 1 to 24; and the remaining variables are as described in the 35$^{th}$ or 36$^{th}$ specific aspect.

In some embodiments, $R_{19}$, $R_{20}$, $R_{21}$ and $R_{22}$ are each H; and m and n are each independently an integer between 1 and 6.

In some embodiments, $P_L$ is a peptide containing 2 to 10 amino acid residues. More specifically, $P_L$ is a peptide containing 2 to 5 amino acid residues. Even more specifically, $P_L$ is selected from the group consisting of: Ala-Val, Val-Ala, Val-Cit, Cit-Val. Val-Lys, Phe-Lys, Lys-Lys, Ala-Lys, Phe-Cit, Leu-Cit, Ile-Cit, Trp-Cit, Phe-Ala, Phe-N$^9$- or a pharmaceutically acceptable salt thereof.

In a 40$^{th}$ specific embodiment, for methods described herein, the imine-containing cytotoxic agent is represented by the following formula:

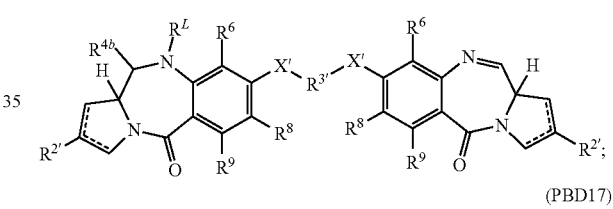

(PBD17′)

(PBD17)

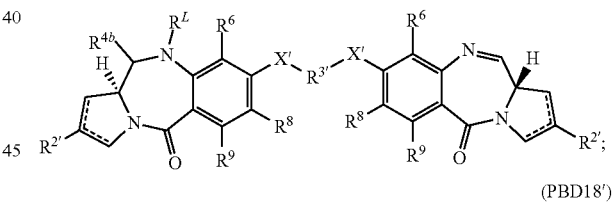

(PBD18′)

(PBD18)

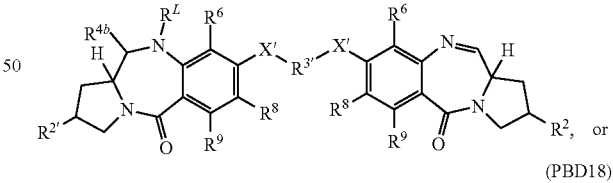

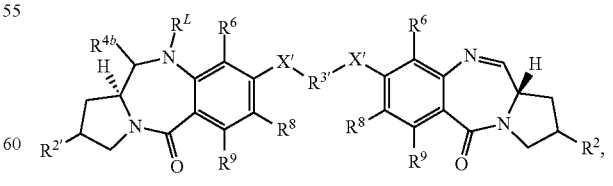

or a pharmaceutically acceptable salt thereof, wherein:

the dotted lines indicate the optional presence of a double bond;

$R^{3''}$ is a C$_{3-12}$ alkylene group, each X', for each occurrence, is independently —O—, —S— or —N(H)—, each $R^2$ is independently selected from —H, —OH, —CN, —$R^{1'}$, —$OR^{1'}$, —O—$SO_2$—$R^{1'}$, —$CO_2R^{1'}$, —$COR'$, or halo, or both $R^2$ taken together, are =O, =$CH_2$, =CH—$R^a$, or =$C(R^a)_2$;

each $R^{2'}$ is independently selected from —H, —OH, —CN, —R", —OR", —O—$SO_2$—R", —$CO_2$R", —COR' or halo;

$R^{4b}$ is a leaving group selected from —$OR^{6'}$, —$OCOR^{4'}$, —$OCOOR^{4'}$, —$OCONR^{4'}R^{5'}$, —$NR^{4'}R^{5'}$, —$NR^{4'}COR^{5'}$, —$NR^{4'}NR^{4'}R^{5'}$, an optionally substituted 5- or 6-membered nitrogen-containing heterocycle (e.g., piperidine, tetrahydropyrrole, pyrazole, morpholine), a guanidinum represented by —$NR^{4'}(C=NH)NR^{4'}R^{5'}$, an amino acid, or a peptide represented by —$NR^{6'}COP'$, wherein P' is an amino acid or a polypeptide containing between 2 to 20 amino acid units, —$SR^{6'}$, —$SOR^{4'}$, —$SO_2M$, —$SO_3M$, —$OSO_3M$, halogen, cyano and an azido;

$R^L$ is linker bearing a maleimide moiety that can form a covalent bond with a cell binding agent (CBA);

$R^6$ and $R^9$ are independently selected from —H, —$R^{1'}$, —OH, —$OR^{1'}$, —SH, —$SR^{1'}$, —$NH_2$, —$NHR^{1'}$, —$NR^{1'}R^{3'}$, —$NO_2$, $Me_3Sn$ and halo; and, $R^{1'}$ and $R^{3'}$ are each independently selected from optionally substituted $C_{1-12}$ alkyl, $C_{3-20}$ heterocyclyl or $C_{5-20}$ aryl groups, and optionally in relation to the group —$NR^{1'}R^{3'}$, $R^{1'}$ and $R^{3'}$ together with the nitrogen atom to which they are attached form an optionally substituted 4-, 5-, 6- or 7-membered heterocyclic ring; or any pair of adjacent groups from $R^6$ to $R^9$ together form a group —O—$(CH_2)_p$—O—, where p is 1 or 2;

$R^{4'}$ and $R^{5'}$ are each independently selected from —H, —OH, —$OR^{6'}$, —$NHR^{6'}$, —$NR^{6'}_2$, —$COR^{6'}$, an optionally substituted linear, branched or cyclic alkyl, alkenyl or alkynyl having from 1 to 10 carbon atoms, a polyethylene glycol unit —$(CH_2CH_2O)_n$—$R^b$, or an optionally substituted 3- to 18-membered heterocyclic ring having 1 to 6 heteroatoms independently selected from O, S, N or P;

$R^{6'}$, for each occurrence, is independently selected from the group consisting of —H, an optionally substituted linear, branched or cyclic alkyl, alkenyl or alkynyl having from 1 to 10 carbon atoms, a polyethylene glycol unit —$(CH_2CH_2O)_n$—$R^b$, an optionally substituted aryl having 6 to 18 carbon atoms, an optionally substituted 5- to 18-membered heteroaryl ring containing one or more heteroatoms independently selected from nitrogen, oxygen, or sulfur, and an optionally substituted 3- to 18-membered heterocyclic ring containing 1 to 6 heteroatoms independently selected from O, S, N or P;

$R^a$ is independently selected from —$R^{1'}$, —$CO_2R^{1'}$, —$COR^{1'}$, —CHO, —$CO_2H$, or halo;

$R^b$ is —H or a substituted or unsubstituted linear or branched alkyl having 1 to 4 carbon atoms;

M is H or a pharmaceutically acceptable cation; and n is an integer from 1 to 24.

In a 41$^{st}$ specific aspect, for the methods described herein, the imine-containing cytotoxic agent is represented by the following formula:

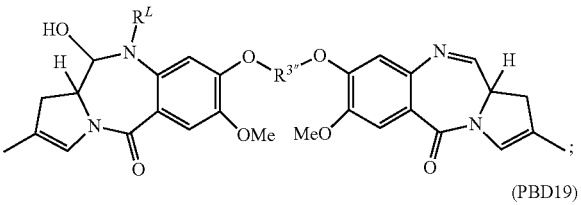

(PBD19')

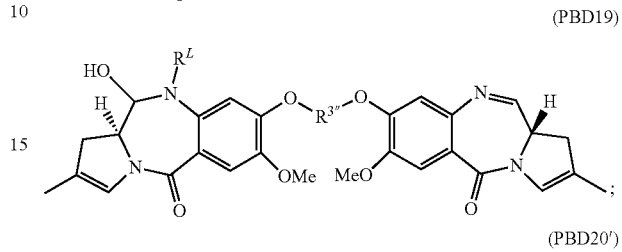

(PBD19)

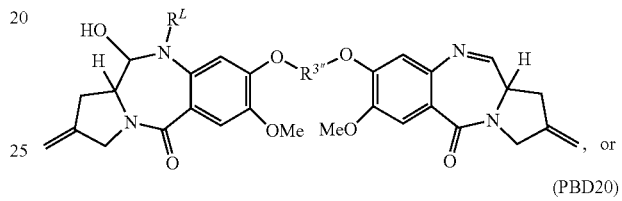

(PBD20')

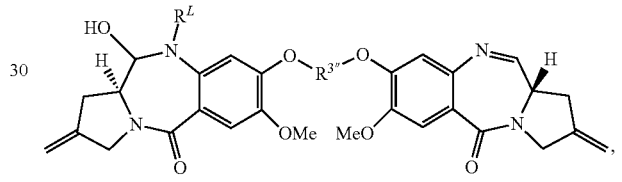

(PBD20)

or a pharmaceutically acceptable salt thereof, wherein $R^{3''}$ is a $C_{3-5}$alkylene; and the remaining variables are as described above in the 40$^{th}$ specific aspect.

In a 42$^{nd}$ specific aspect, for formula (PBD17'), (PBD18'), (PBD19'), (PBD20'), (PBD17), (PBD18), (PBD19) or (PBD20), $R^L$ is

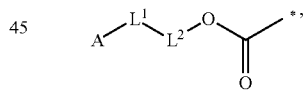

wherein $L^1$ is a cleavable linker, A is a connecting group bearing a maleimide capable of connecting $L^1$ to the cell binding agent, $L^2$ is a covalent bond or together with —OC(=O)— forms a self-immolative linker; and the remaining variables are as described above in the 40$^{th}$ or 41$^{st}$ specific aspect.

In a 43$^{rd}$ specific aspect, for $R^L$ described in the 42$^{nd}$ specific aspect, $L^1$ is a peptide containing 2 to 10 amino acid residues; and the remaining variables are as described above in the 42$^{nd}$ specific aspect. More specifically, $L^1$ is a peptide containing 2 to 5 amino acid residues. Even more specifically, $L^1$ is selected from the group consisting of Phe-Lys, Val-Ala, Val-Lys, Ala-Lys, Val-Cit, Phe-Cit, Leu-Cit, Ile-Cit, Phe-Arg, Trp-Cit, Lys-Lys, Phe-Ala, Phe-N9-tosyl-Arg, Phe-N9-nitro-Arg, Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Gly-Gly-Gly, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO:1), β-Ala-Leu-Ala-Leu (SEQ ID NO:2) and Gly-Phe-Leu-Gly (SEQ ID NO:3).

In a 44$^{th}$ specific aspect, for R$^L$ described in the 42$^{nd}$ specific aspect, —C(=O)O— and L$^2$ together form the group:

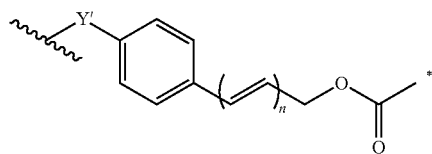

where the asterisk indicates the point of attachment to the N10 position, the wavy line indicates the point of attachment to the linker L$^1$, Y' is —NH—, —O—, —C(=O)NH— or —C(=O)O—, and n is 0 to 3; and the remaining variables are as described in the 42$^{nd}$ or 43$^{rd}$ specific aspect.

In a 45$^{th}$ specific aspect, for R$^L$ described in the 42$^{nd}$ specific aspect, —C(=O)O— and L$^2$ together form the group:

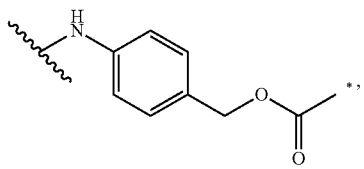 [SMILES: *Nc1ccc(COC(C)=O)cc1]

and the remaining variables are as described in the 42$^{nd}$ or 43$^{rd}$ specific aspect.

In a 46$^{th}$ specific aspect, for R$^L$ described in the 42$^{nd}$ specific aspect, L$^1$ and L$^2$ together with —OC(=O)— comprise a group selected from:

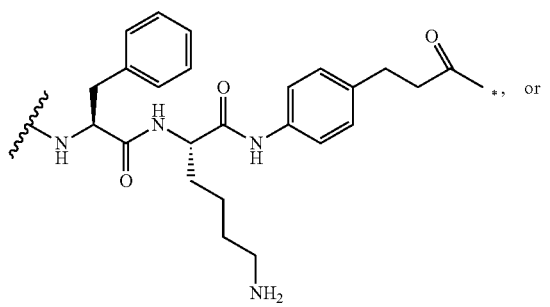

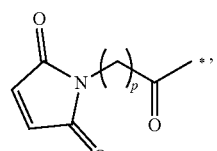

where the asterisk indicates the point of attachment to the N10 position, and the wavy line indicates the point of attachment to the remaining portion of the linker L$^1$ or the point of attachment to A.

In a 47$^{th}$ specific aspect, for R$^L$ described in the 42$^{nd}$ specific aspect, A is represented by one of the following:

(i)

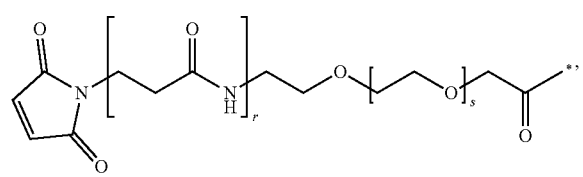

where the asterisk indicates the point of attachment to L$^1$, and p is 1 to 6; or (ii)

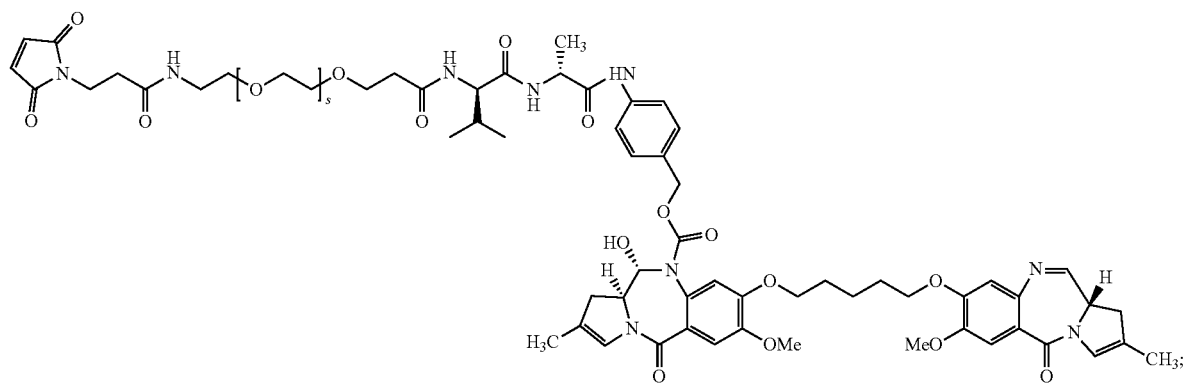

where the asterisk indicates the point of attachment to L$^1$, r is 0 or 1, and s is 0 to 30;

and the remaining variables are as described in the 42$^{nd}$, 43$^{rd}$, 44$^{th}$, 45$^{th}$ or 46$^{th}$ specific aspect.

In some embodiments, p is 4 to 6; r is 1; and s is 1 to 10.

In a 48$^{th}$ specific aspect, for methods described in the present invention, the imine-containing cytotoxic agent is represented by the following formula:

or a pharmaceutically acceptable salt thereof, the modified imine-containing cytotoxic agent is represented by the following formula:

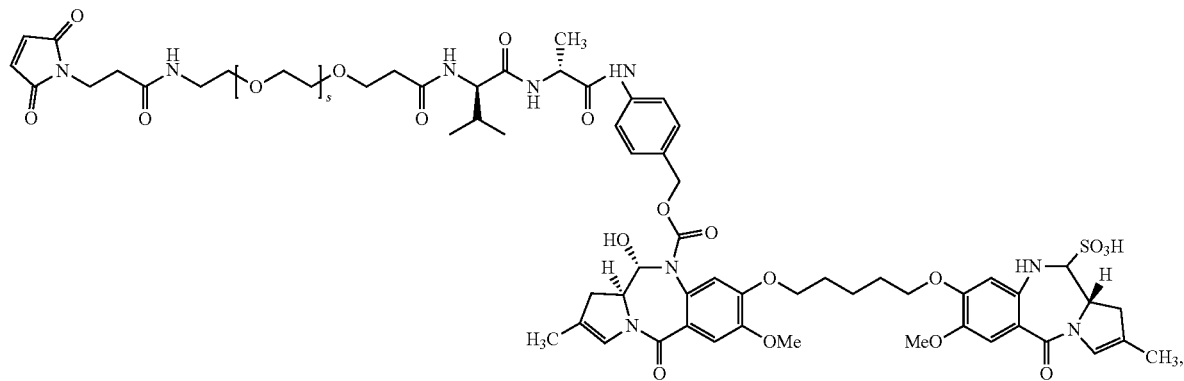

or a pharmaceutically acceptable salt thereof, and the conjugate is represented by the following formula:

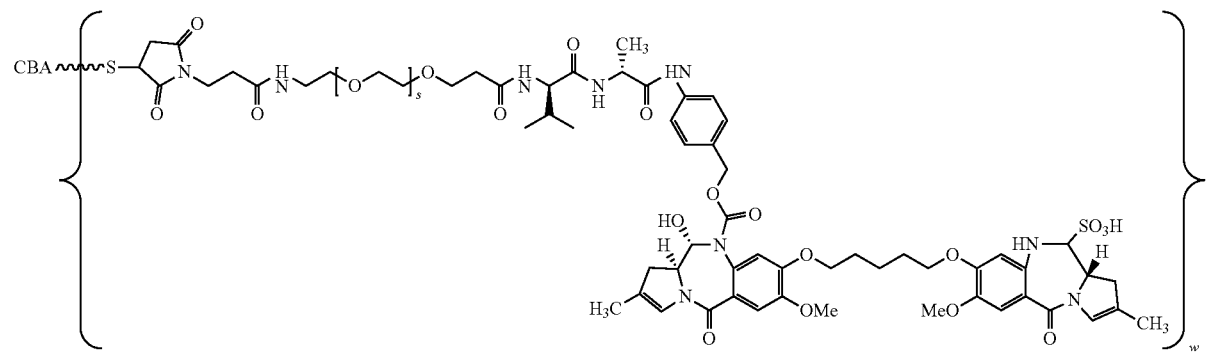

wherein s is 2 to 8; w is 1 or 2; and CBA is a cell-binding agent described herein. In some embodiments, s is 7.

In some embodiments, for methods described in the present invention, the imine-containing cytotoxic agent is represented by the following formula:

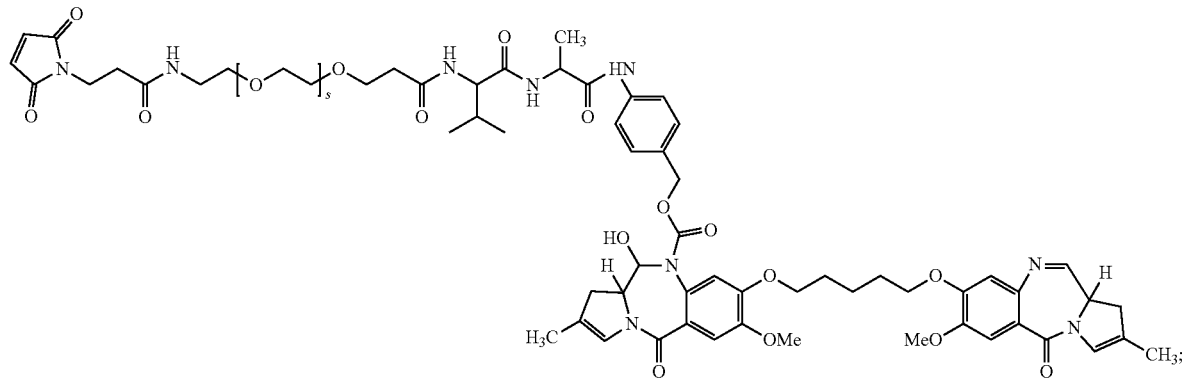

or a pharmaceutically acceptable salt thereof, the modified imine-containing cytotoxic agent is represented by the following formula:

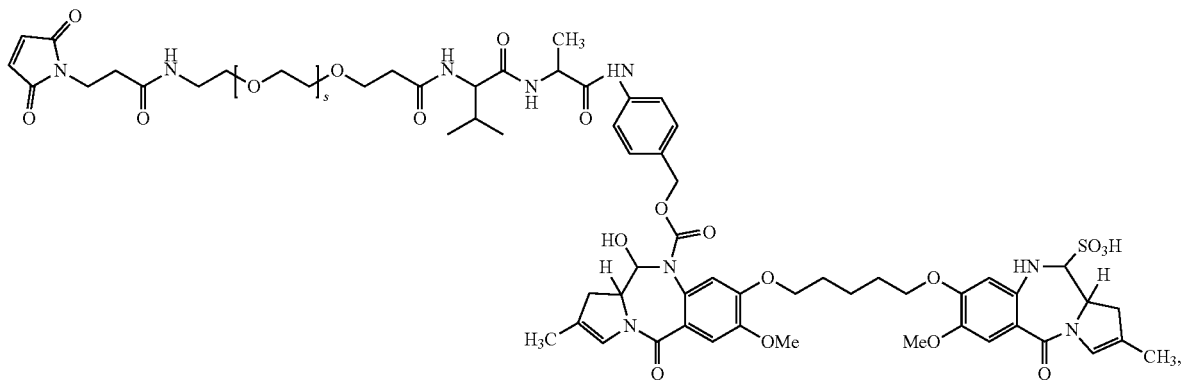
or a pharmaceutically acceptable salt thereof, and the conjugate is represented by the following formula:
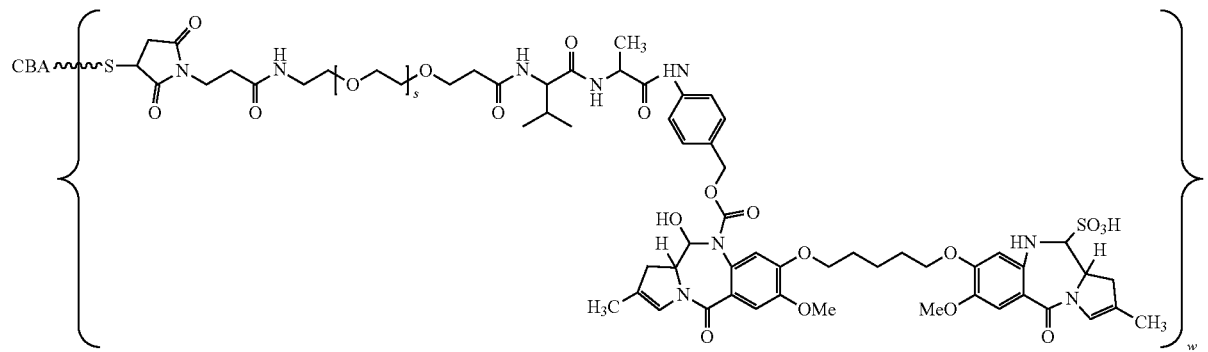
wherein s is 2 to 8; w is 1 or 2; and CBA is a cell-binding agent described herein. In some embodiments, s is 7.
In a 49$^{th}$ specific aspect, for methods described in the present invention, the imine-containing cytotoxic agent is represented by the following formula:
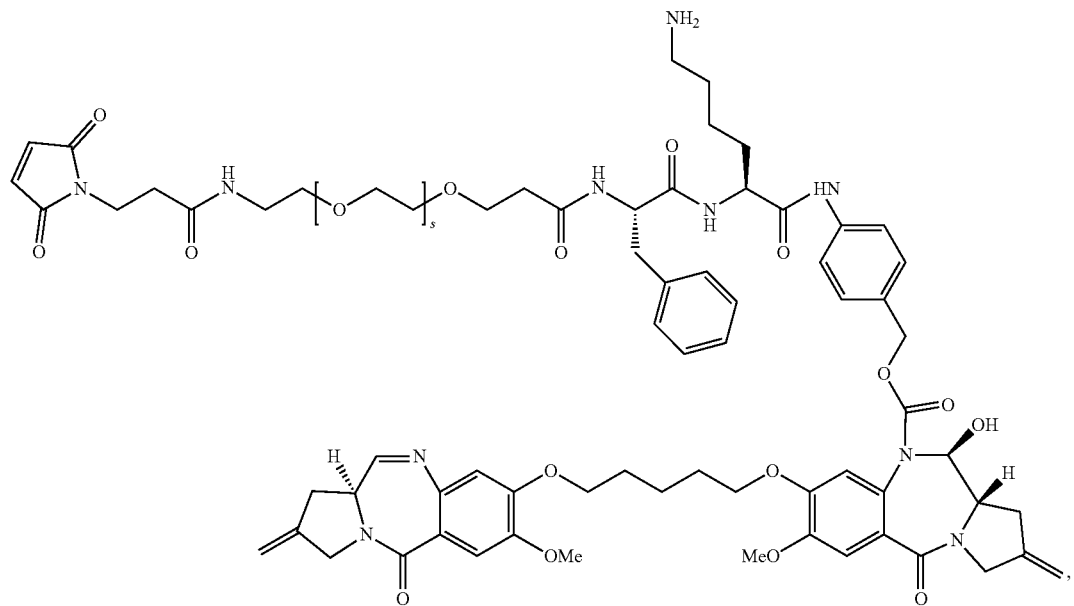

or a pharmaceutically acceptable salt thereof, the modified imine-containing cytotoxic agent is represented by the following formula:

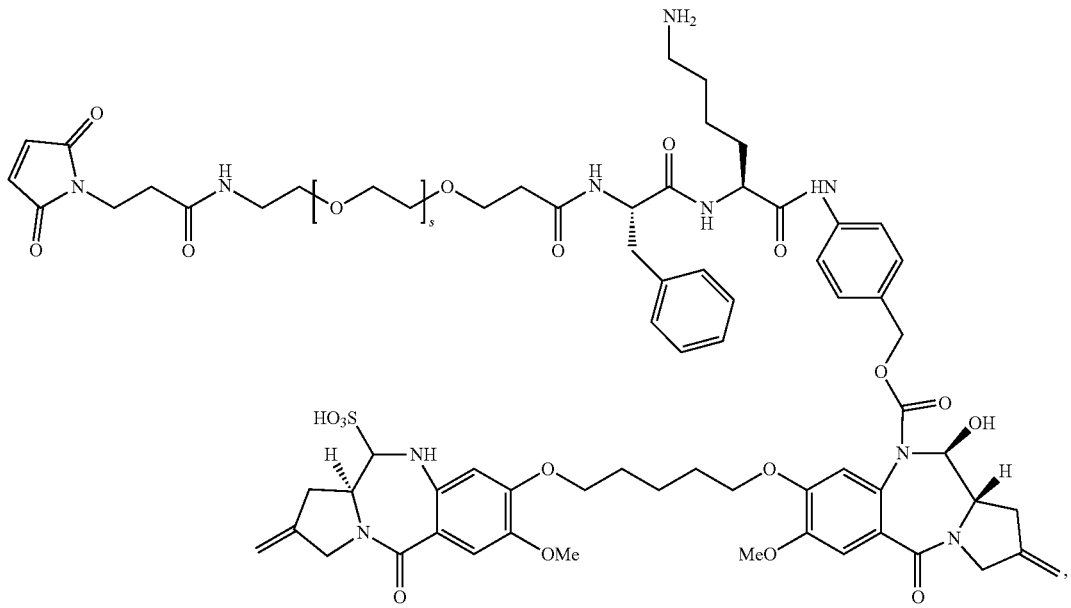

or a pharmaceutically acceptable salt thereof, and the conjugate is represented by the following formula:

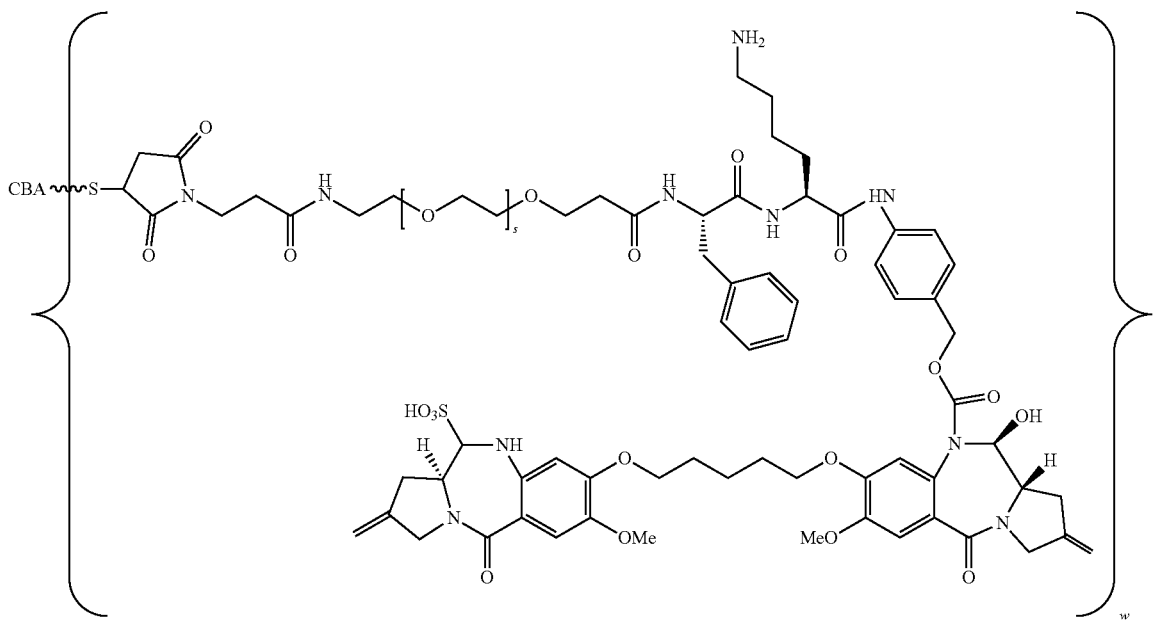

or a pharmaceutically acceptable salt thereof, wherein s is 2 to 8; w is 1 or 2; and CBA is a cell-binding agent described herein. In some embodiments, s is 7.

In some embodiments, for methods described in the present invention, the imine-containing cytotoxic agent is represented by the following formula:

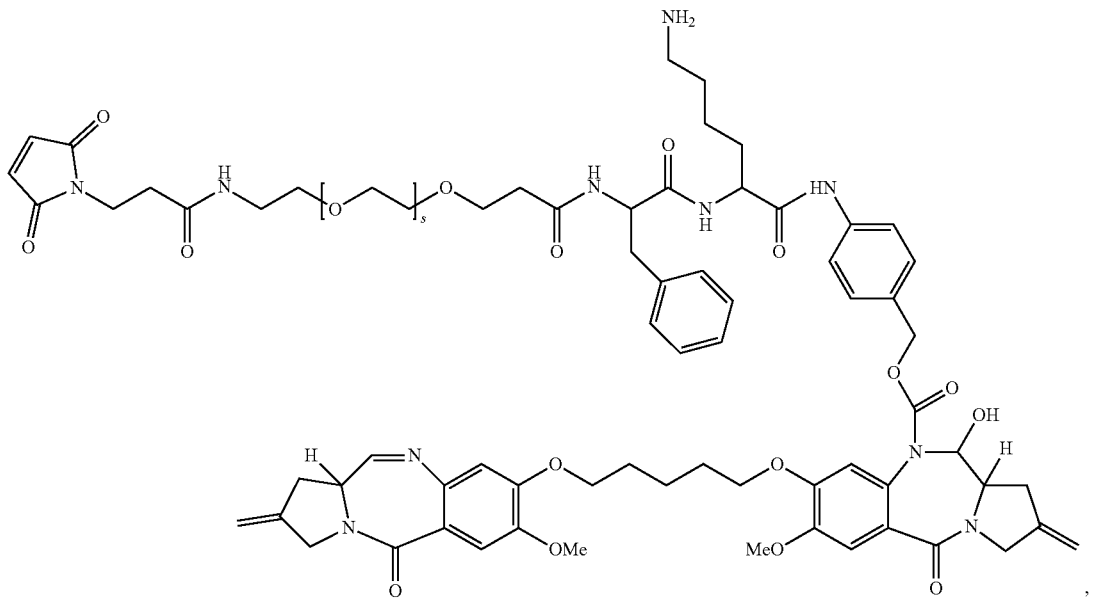
or a pharmaceutically acceptable salt thereof, the modified imine-containing cytotoxic agent is represented by the following formula:
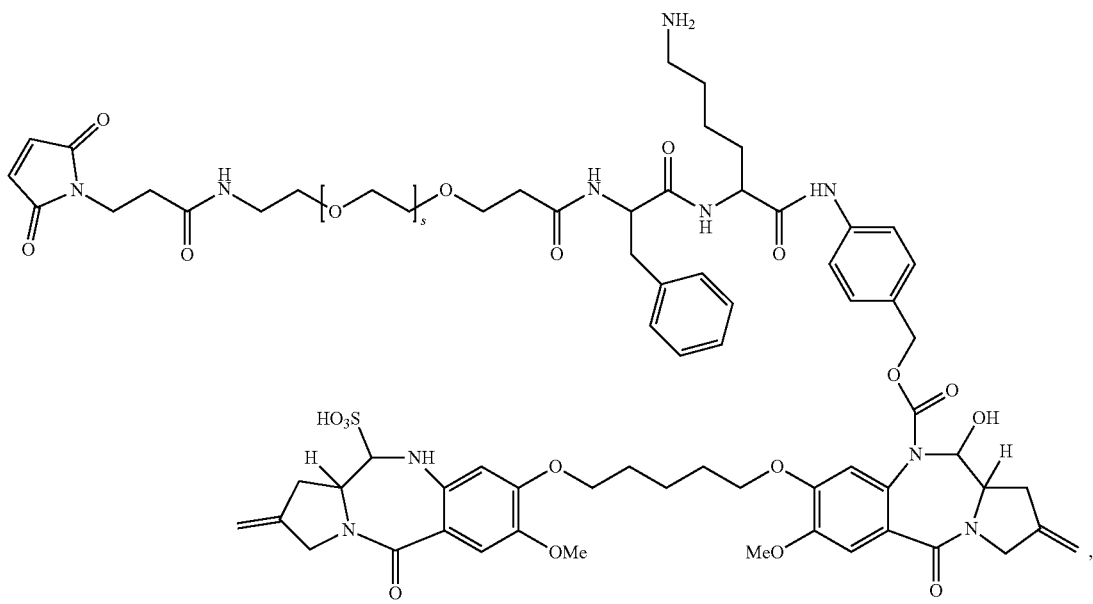
or a pharmaceutically acceptable salt thereof, and the conjugate is represented by the following formula:

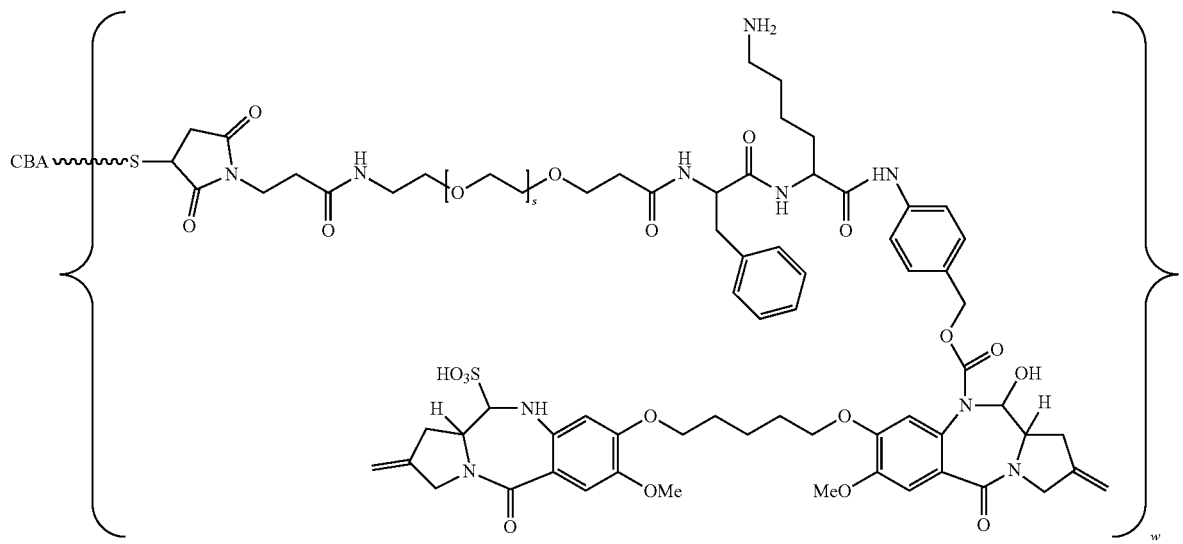

or a pharmaceutically acceptable salt thereof, wherein s is 2 to 8; w is 1 or 2; and CBA is a cell-binding agent described herein. In some embodiments, s is 7.

In some embodiments, the charged substituent or an ionizable group Q described in any embodiments above is i) —$SO_3H$, —Z'—$SO_3H$, —$OPO_3H_2$, —Z'—$OPO_3H_2$, —$PO_3H_2$, —Z'—$PO_3H_2$, —$CO_2H$, —Z'—$CO_2H$, —$NR_{11}R_{12}$, or —Z'—$NR_{11}Z_{12}$, or a pharmaceutically acceptable salt thereof; or, ii) —$N^+R_{14}R_{15}R_{16}X^-$ or —Z'—$N^+R_{14}R_{15}R_{16}X^-$; Z' is an optionally substituted alkylene, an optionally substituted cycloalkylene or an optionally substituted phenylene; $R_{14}$ to $R_{16}$ are each independently an optionally substituted alkyl; and $X^-$ is a pharmaceutically acceptable anion. More specifically, Q is —$SO_3H$ or a pharmaceutically acceptable salt thereof. Even more specifically, Q is —$SO_3Na$.

Cell-Binding Agents

In some embodiments, the cell-binding agent can be used in the present methods is an antibody having an engineered cysteine residue (e.g., at the EU/OU numbering position 442 of the heavy chain(s)). The engineered Cys residue can be located on one or both heavy chains of the antibody, or on one or both light chains of the antibody, or antigen-binding portion thereof, or a combination thereof. In some embodiments, the Cys residue is located at the EU/OU numbering position 442 of the antibody heavy chain(s). In some embodiments, the antibody is a cysteine engineered antibody as described herein.

In some embodiments, the antibody of the present invention is a monoclonal antibody, a chimeric antibody, a humanized antibody, a resurfaced antibody, or a human antibody.

In other embodiments, the cell-binding agent is an antibody, a single chain antibody, an antibody fragment that specifically binds to the target cell, a monoclonal antibody, a single chain monoclonal antibody, a monoclonal antibody fragment (or "antigen-binding portion") that specifically binds to a target cell, a chimeric antibody, a chimeric antibody fragment (or "antigen-binding portion") that specifically binds to the target cell, a domain antibody (e.g., sdAb), or a domain antibody fragment that specifically binds to the target cell.

In yet other embodiments, the cell-binding agent is a humanized antibody, a humanized single chain antibody, or a humanized antibody fragment (or "antigen-binding portion"). In a specific embodiment, the humanized antibody is huMy9-6 or another related antibody, which is described in U.S. Pat. Nos. 7,342,110 and 7,557,189. In another specific embodiment, the humanized antibody is an anti-folate receptor antibody described in U.S. Pat. No. 8,557,966. In yet other embodiments, the humanized antibody is an anti-CD123 antibody described in U.S. application Ser. No. 15/195,401, filed on Jun. 28, 2016, entitled "ANTI-CD123 ANTIBODIES AND CONJUGATES AND DERIVATIVES THEREOF." The teachings of all these applications are incorporated herein by reference in its entirety.

In some embodiments, the cell-binding agent is a resurfaced antibody, a resurfaced single chain antibody, a resurfaced antibody fragment (or "antigen-binding portion"), or a bispecific antibody.

Yet another aspect of the invention provides a recombinant antibody comprising a mature processed sequence of the heavy chain, light chain, or antigen-binding portion thereof, derived from any one of the subject recombinant antibody heavy chain (HC), light chain (LC), or antigen-binding portion thereof described herein.

For example, the recombinant antibody may be or may comprise an scFv-Fc, Fcab, mAb2, small modular immunopharmaceutical (SMIP), Genmab/unibody or duobody, minibody, IgGΔCH2, DVD-Ig, probody, intrabody, or a multispecificity antibody.

A DUOBODY® is a bispecific modified IgG1 antibody heterodimer. IgG1 hinge region that generally includes (i) a stable hinge region that contains a CPPC sequence and is non-permissive for Fab arm exchange in vivo and (ii) an IgG4-like CH3 domain that is modified to contain F405L and K409R residues, which renders it permissive for Fab arm exchange in vivo. (See, for example, WO2008119353 and WO2011131746).

In some embodiments, the recombinant antibody may comprise 1, 2, 3, or 4 of the mature processed sequence of the heavy chain, light chain, or antigen-binding portion thereof, each derived from any one of the subject recombinant antibody heavy chain (HC), light chain (LC), or antigen-binding portion thereof described herein.

In other embodiments, the recombinant antibody may be a heterodimeric antibody comprising a first heavy chain polypeptide and a second heavy chain polypeptide, wherein the Fc region of the first heavy chain polypeptide and the Fc region of the second heavy chain polypeptide meet at an interface, and the interface of the Fc region of the second heavy chain polypeptide comprises a protuberance which is positionable in a cavity in the interface of the Fc region of the first heavy chain polypeptide. In certain embodiments, the knob-into-hole technology to promote specific pairing of heavy chains in the bi-specific antibody may be further improved based on, for example, the CrossMab technology of Genentech/Roche, e.g., by swapping CH1 and Kappa constant regions to further reduce or eliminate light chain mis-pairing.

Alternatively, similar results can also be achieved using LC heterodimers, such as Zymeworks AZYMETRIC™ heterodimeric IgG1 light chain platform technology that fully complements multiple other biologics approaches, including common light chain, domain antibody, and single chain formats, in the development of fully bi-specific antibodies.

In some embodiments, the Fc region of the second heavy chain polypeptide has been altered from a template/original polypeptide to encode the protuberance, or the Fc region of the first heavy chain polypeptide has been altered from a template/original polypeptide to encode the cavity, or both.

In other embodiments, the protuberance and the cavity each comprises a naturally occurring amino acid residue.

In other embodiments, the Fc region of the second heavy chain polypeptide comprising the protuberance is generated by replacing an original residue from the interface of a template/original polypeptide with an import residue having a larger side chain volume than the original residue.

In yet other embodiments, the Fc region of the second heavy chain polypeptide comprising the protuberance is generated by a method comprising a step wherein nucleic acids encoding an original residue from the interface of said polypeptide is replaced with nucleic acids encoding an import residue having a larger side chain volume than the original.

In some embodiments, the antibody includes bispecific, multispecific, and monospecific antibody variants that include the antigen bind regions and the heavy chain constant domain, wherein the heavy chain constant domain is modified to include a Cys at position 442 of the EU/OU numbering.

In other embodiments, the antibody may bind to a ligand on the target cell, such as a cell-surface ligand, including cell-surface receptors.

Specific exemplary antigens or ligands may include renin; a growth hormone (e.g., human growth hormone and bovine growth hormone); a growth hormone releasing factor; a parathyroid hormone; a thyroid stimulating hormone; a lipoprotein; alpha-1-antitrypsin; insulin A-chain; insulin B-chain; proinsulin; a follicle stimulating hormone; calcitonin; a luteinizing hormone; glucagon; a clotting factor (e.g., factor vmc, factor IX, tissue factor, and von Willebrands factor); an anti-clotting factor (e.g., Protein C); an atrial natriuretic factor; a lung surfactant; a plasminogen activator (e.g., a urokinase, a human urine or tissue-type plasminogen activator); bombesin; a thrombin; hemopoietic growth factor; tumor necrosis factor-alpha and -beta; an enkephalinase; RANTES (i.e., the regulated on activation normally T-cell expressed and secreted); human macrophage inflammatory protein-1-alpha; a serum albumin (human serum albumin); Muellerian-inhibiting substance; relaxin A-chain; relaxin B-chain; prorelaxin; a mouse gonadotropin-associated peptide; a microbial protein (beta-lactamase); DNase; IgE; a cytotoxic T-lymphocyte associated antigen (e.g., CTLA-4); inhibin; activin; a vascular endothelial growth factor; a receptor for hormones or growth factors; protein A or D; a rheumatoid factor; a neurotrophic factor (e.g., bone-derived neurotrophic factor, neurotrophin-3, -4, -5, or -6), a nerve growth factor (e.g., NGF-β); a platelet-derived growth factor; a fibroblast growth factor (e.g., aFGF and bFGF); fibroblast growth factor receptor 2; an epidermal growth factor; a transforming growth factor (e.g., TGF-alpha, TGF-β1, TGF-β2, TGF-β3, TGF-β4, and TGF-β5); insulin-like growth factor-I and -II; des(1-3)-IGF-I (brain IGF-I); an insulin-like growth factor binding protein; melanotransferrin; EpCAM; GD3; FLT3; PSMA; PSCA; MUC1; MUC16; STEAP; CEA; TENB2; an EphA receptor; an EphB receptor; a folate receptor; FOLR1; mesothelin; cripto; an alpha$_v$beta$_6$; integrins; VEGF; VEGFR; EGFR; transferrin receptor; IRTA1; IRTA2; IRTA3; IRTA4; IRTA5; CD proteins (e.g., CD2, CD3, CD4, CD5, CD6, CD8, CD11, CD14, CD19, CD20, CD21, CD22, CD25, CD26, CD28, CD30, CD33, CD36, CD37, CD38, CD40, CD44, CD52, CD55, CD56, CD59, CD70, CD79, CD80. CD81, CD103, CD105, CD123, CD134, CD137, CD138, and CD152), one or more tumor-associated antigens or cell-surface receptors (see US Publication No. 2008/0171040 or US Publication No. 2008/0305044, incorporated in their entirety by reference); erythropoietin; an osteoinductive factor; an immunotoxin; a bone morphogenetic protein; an interferon (e.g., interferon-alpha, -beta, and -gamma); a colony stimulating factor (e.g., M-CSF, GM-CSF, and G-CSF); interleukins (e.g., IL-1 to IL-10); a superoxide dismutase; a T-cell receptor; a surface membrane protein; a decay accelerating factor; a viral antigen (e.g., a portion of the HIV envelope); a transport protein, a homing receptor; an addressin; a regulatory protein; an integrin (e.g., CD11a, CD11b, CD11c, CD18, an ICAM, VLA-4, and VCAM;) a tumor associated antigen (e.g., HER2, HER3 and HER4 receptor); endoglin; c-Met; c-kit; 1GF1R; PSGR; NGEP; PSMA; PSCA; TMEFF2; LGRS; B7H4; and fragments of any of the above-listed polypeptides.

In some embodiments, the cell-binding agent is an anti-folate receptor antibody. More specifically, the anti-folate receptor antibody is a humanized antibody that specifically binds a human folate receptor 1, wherein the antibody comprises: (a) a heavy chain CDR1 comprising GYFMN (SEQ ID NO: 4); a heavy chain CDR2 comprising RIHPYDGDTFYNQXaa$_1$FXaa$_2$Xaa$_3$ (SEQ ID NO: 5); and a heavy chain CDR3 comprising YDGSRAMDY (SEQ ID NO: 6); and (b) a light chain CDR1 comprising KASQS-VSFAGTSLMH (SEQ ID NO: 7); a light chain CDR2 comprising RASNLEA (SEQ ID NO: 8); and a light chain CDR3 comprising QQSREYPYT (SEQ ID NO: 9); wherein Xaa$_1$ is selected from K, Q, H, and R; Xaa$_2$ is selected from Q, H, N, and R; and Xaa$_3$ is selected from G, E, T, S, A, and V. Preferably, the heavy chain CDR2 sequence comprises

```
                                        (SEQ ID NO: 10)
                RIHPYDGDTFYNQKFQG.
```

In other embodiments, the anti-folate receptor antibody is a humanized antibody or antigen binding fragment thereof that specifically binds the human folate receptor 1 comprising the heavy chain having the amino acid sequence of

```
QVQLVQSGAEVVKPGASVKISCKASGYTFTGYFMNWVKQSPGQSLEWIGR

IHPYDGDTFYNQKFQGKATLTVDKSSNTAHMELLSLTSEDFAVYYCTRYD
```

-continued

GSRAMDYWGQGTTVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTV

In other embodiments, the anti-folate receptor antibody is a humanized antibody or antigen binding fragment thereof that specifically binds the human folate receptor 1 comprising the light chain having the amino acid sequence of (SEQ ID NO: 12)
DIVLTQSPLSLAVSLGQPAIISCKASQSVSFAGTSLMHWYHQKPGQQPRL

LIYRASNLEAGVPDRFSGSGSKTDFTLNISPVEAEDAATYYCQQSREYPY

TFGGGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC;
or (SEQ ID NO: 13)
DIVLTQSPLSLAVSLGQPAIISCKASQSVSFAGTSLMHWYHQKPGQQPRL

LIYRASNLEAGVPDRFSGSGSKTDFTLTISPVEAEDAATYYCQQSREYPY

TFGGGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC.

In other embodiments the anti-folate receptor antibody is a humanized antibody or antigen binding fragment thereof that specifically binds the human folate receptor 1 comprising the heavy chain having the amino acid sequence of SEQ ID NO: 11, and the light chain having the amino acid sequence of SEQ ID NO: 12 or SEQ ID NO: 13. Preferably, the antibody comprises the heavy chain having the amino acid sequence of SEQ ID NO: 11 and the light chain having the amino acid sequence of SEQ ID NO: 13 (huMov19).

In other embodiments, the anti-folate receptor antibody is a humanized antibody or antigen binding fragment thereof comprising an engineered Cys residue (e.g., C442) and a heavy chain variable domain at least about 90%, 95%, 99% or 100% identical to QVQLVQSGAEVVKPGASVKISCK-ASGYTFTGYFMNWVKQSPGQSLEWIGRIHPYDGDT FYNQKFQGKATLTVDKSSNTAHMELLSLTSED-FAVYYCTRYDGSRAMDYWGQGTTVT VSS (SEQ ID NO: 14), and a light chain variable domain at least about 90%, 95%, 99% or 100% identical to (SEQ ID NO: 15)
DIVLTQSPLSLAVSLGQPAIISCKASQSVSFAGTSLMHWYHQKPGQQPRL
LIYRASNLEAGVPDRFSGSGSKTDFTLNISPVEAEDAATYYCQQSREYPY
TFGGGTKLEIKR;
or (SEQ ID NO: 16)
DIVLTQSPLSLAVSLGQPAIISCKASQSVSFAGTSLMHWYHQKPGQQPRL
LIYRASNLEAGVPDRFSGSGSKTDFTLTISPVEAEDAATYYCQQSREYPY
TFGGGTKLEIKR.

In a specific embodiment, the humanized antibody is huMy9-6 or another related antibody, which is described in U.S. Pat. Nos. 7,342,110 and 7,557,189. In another specific embodiment, the humanized antibody is an anti-folate receptor antibody (e.g., huMov19) described in U.S. Pat. No. 8,577,966. In certain embodiments the humanized antibody is an anti-CD37 antibody (e.g., anti-CD37-3) described in U.S. Pat. No. 8,765,917. In certain embodiments, the humanized antibody is an anti-EGFR antibody described in U.S. Pat. No. 8,790,649. In other embodiments, the antibody is an anti-EGFR antibody. In some embodiments, the anti-EGFR antibody is a non-antagonist antibody, including, for example, the antibodies described in WO2012058592, herein incorporated by reference. In other embodiments, the anti-EGFR antibody is a non-functional antibody, for example, humanized ML66. More specifically, the anti-EGFR antibody is huML66.

In some embodiments, the antibody is an anti-CD123 antibody, such as a humanized huCD123 antibody as described in U.S. application Ser. No. 15/195,401, filed on Jun. 28, 2016, entitled "ANTI-CD123 ANTIBODIES AND CONJUGATES AND DERIVATIVES THEREOF" (entire contents, including all sequences and drawings, incorporated herein). In a specific embodiment, the anti-CD123 antibody the antibody or antigen-binding fragment thereof comprises: a) at least one heavy chain variable region or fragment thereof comprising three sequential complementarity-determining regions (CDR) CDR1, CDR2, and CDR3, respectively, wherein, CDR1 has the sequence of SSIMH (SEQ ID NO:17), CDR2 has the sequence of YIKPYNDGT-KYNEKFKG (SEQ ID NO:18), and, CDR3 has the sequence of EGGNDYYDTMDY (SEQ ID NO:19); and b) at least one light chain variable region or fragment thereof comprising three sequential complementarity-determining regions (CDR) CDR1, CDR2, and CDR3, respectively, wherein, CDR1 has the sequence of RASQDINSYLS (SEQ ID NO:20), CDR2 has the sequence of RVNRLVD (SEQ ID NO:21), and, CDR3 has the sequence of LQYDAFPYT (SEQ ID NO:22).

In another specific embodiments, the anti-CD123 antibody or antigen-binding fragment thereof comprises an engineered Cys residue (e.g., C442); an immunoglobulin heavy chain variable domain at least about 90%, 95%, 99% or 100% identical to QXQLVQSGAEVKKPGASVK-VSCKASGYIFTSSIMHWVRQAPGQGLEWIGYIK-PYNDGT KYNEKFKGRATLTSDRSTSTAYMELSSL-RSEDTAVYYCAREGGNDYYDTMDYWGQGT LVTVSS (SEQ ID NO:23); and an immunoglobulin light chain variable region having the amino acid sequence at least about 90%, 95%, 99% or 100% identical to (SEQ ID NO: 24)
DIQMTQSPSSLSASVGDRVTITCRASQDINSYLSWFQQKPGKAPKTLIYR
VNRLVDGVPSRFSGSGSGNDYTLTISSLQPEDFATYYCLQYDAFPYTFGQ
GTKVEIKR.

In certain embodiments, Xaa, the second residue from the N-terminus of SEQ ID NO: 23, is Phe. In other embodiments, Xaa is Val.

In certain embodiments, the anti-CD123 antibody or antigen-binding fragment thereof may comprise: an immunoglobulin heavy chain region having the amino acid sequence of (SEQ ID NO: 25)
QVQLVQSGAEVKKPGASVKVSCKASGYIFTSSIMHWVRQAPGQGLEWIGY

IKPYNDGTKYNEKFKGRATLTSDRSTSTAYMELSSLRSEDTAVYYCAREG

GNDYYDTMDYWGQGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLCLSP

G;

and an immunoglobulin light chain region having the amino acid sequence of (SEQ ID NO: 26)
DIQMTQSPSSLSASVGDRVTITCRASQDINSYLSWFQQKPGKAPKTLIYR

VNRLVDGVPSRFSGSGSGNDYTLTISSLQPEDFATYYCLOYDAFPYTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

Compositions and Methods of Use

The present invention also includes the cell-binding agent-cytotoxic agent conjugates prepared by any methods of the present invention, a composition (e.g., a pharmaceutical composition) comprising the cell-binding agent-cytotoxic agent conjugates prepared by any methods of the present invention and a carrier (a pharmaceutically acceptable carrier). The present conjugates and compositions are useful for inhibiting abnormal cell growth or treating a proliferative disorder in a mammal (e.g., human). The present invention includes a method of inhibiting abnormal cell growth or treating a proliferative disorder in a mammal (e.g., human) comprising administering to said mammal a therapeutically effective amount of the conjugates prepared by the methods of the present invention described above or a composition thereof, alone or in combination with a second therapeutic agent.

In some embodiments, the proliferative disorder is cancer. Cancer can include a hematological cancer or a solid tumor. More specifically, the cancer is leukemia (e.g., acute myeloid leukemia (AML), acute lymphoblastic leukemia (ALL) such as acute B lymphoblastic leukemia (B-ALL), chronic myelogenous leukemia (CML), chronic lymphocytic leukemia (CLL)) or lymphoma, melanoma, lung cancer (e.g., non-small cell lung cancer), ovarian cancer, endometrial cancer, peritoneal cancer, pancreatic cancer, breast cancer, prostate cancer, and cervical cancer.

The present invention also provides methods of treatment comprising administering to a subject in need of treatment an effective amount of any of the conjugates described above.

Similarly, the present invention provides a method for inducing cell death in selected cell populations comprising contacting target cells or tissue containing target cells with an effective amount of a cytotoxic agent comprising any of the conjugates described above. The target cells are cells to which the cell-binding agent can bind.

If desired, other active agents, such as other anti-tumor agents, may be administered along with the conjugate.

Suitable pharmaceutically acceptable carriers, diluents, and excipients are well known and can be determined by those of ordinary skill in the art as the clinical situation warrants. Examples of suitable carriers, diluents and/or excipients include: (1) Dulbecco's phosphate buffered saline, pH about 7.4, containing or not containing about 1 mg/mL to 25 mg/mL human serum albumin, (2) 0.9% saline (0.9% w/v NaCl), and (3) 5% (w/v) dextrose; and may also contain an antioxidant such as tryptamine and a stabilizing agent such as Tween 20.

EXAMPLES

Example 1. Preparation of Imine-Containing Cytotoxic Agents

The following solvents, reagents, protecting groups, moieties and other designations may be referred to by their abbreviations in parenthesis:

| | |
|---|---|
| Me | methyl |
| i-Pr | isopropyl |
| Ph | phenyl |
| Ala | alanine |
| DI water | deionized water |
| g | grams |
| h | hour |
| min | minutes |
| mg | milligrams |
| mL | milliliters |
| μg | micrograms |
| μL | microliters |
| sat or sat'd | saturated |
| THF | tetrahydrofuran |
| Et | ethyl |
| Bu | butyl |
| Ac | acetyl |
| aq | aqueous |
| DCM/$CH_2Cl_2$ | dichloromethane |
| DMA | N,N-dimethylacetamide |
| DMF | N,N-dimethylformamide |
| EtOAc | ethylacetate |
| LC | liquid chromatography |
| mmol | millimoles |
| μmol | micromoles |
| MeOH | methanol |
| RT or rt | room temperature (ambient, about 25° C.) |
| TEA | triethylamine ($Et_3N$) |
| Pr | propyl |
| t-Bu | tert-butyl |
| AcOH/HOAc | acetic acid |
| ACN/$CH_3CN$ | acetonitrile |
| Boc/BOC | tert-butoxycarbonyl |
| DIEA or DIPEA | N,N-diisopropylethylamine |
| EDC | 1-ethyl-3-(3-dimethylaminopropyl) carbodiimide |
| ESI or ES | electrospray ionization |
| HPLC | high-performance liquid chromatography |
| LCMS | liquid chromatography mass spectrometry |
| MS | mass spectrometry |
| NHS | N-hydroxy succinamide |
| NMR | nuclear magnetic resonance spectrascopy |
| RPHPLC or RP-HPLC | reverse phase high-performance liquid chromatography |

A. Synthesis of N1-(2-(2,5-dioxo-2,5-dihydro-1H-pyrrol-1-yl)ethyl)-N6-((S)-1-(((S)-1-((3-((((S)-8-methoxy-6-oxo-11,12,12a,13-tetrahydro-6H-benzo[5,6][1,4]diazepino[1,2-a]indol-9-yl)oxy)methyl)-5-(a(S)-8-methoxy-6-oxo-12a,13-dihydro-6H-benzo[5,6][1,4]diazepino[1,2-a]indol-9-yl)oxy)methyl)phenyl)amino)-1-oxopropan-2-yl)amino)-1-oxopropan-2-yl)adipamide, Compound D1

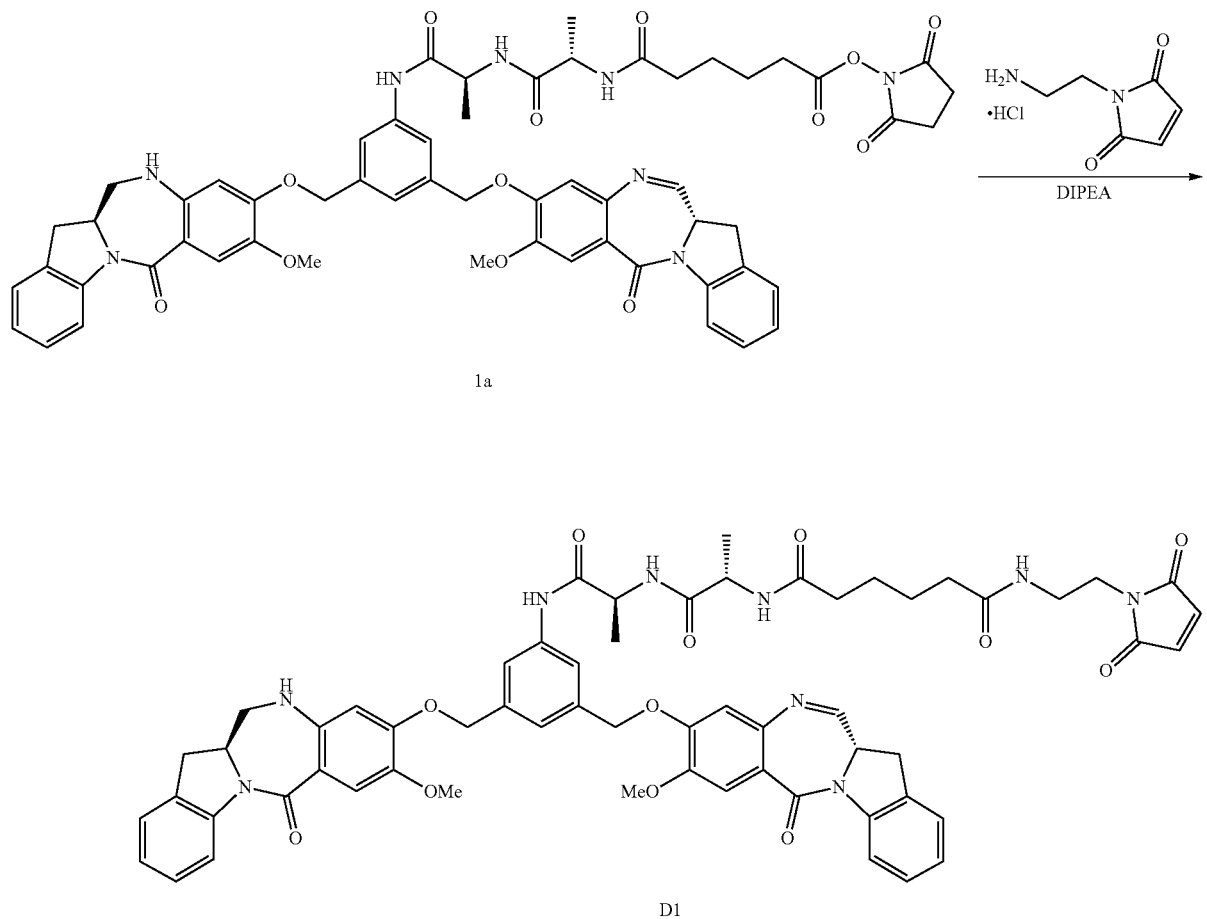 [SMILES: COc1cc2c(cc1OCc1cc(COc3cc4c(cc3OC)C(=O)N3c5ccccc5C[C@H]3CN4)cc(NC(=O)[C@H](C)NC(=O)[C@H](C)NC(=O)CCCCC(=O)ON3C(=O)CCC3=O)c1)N=C[C@@H]1Cc3ccccc3N1C2=O ; Cl ; NCCN1C(=O)C=CC1=O ; COc1cc2c(cc1OCc1cc(COc3cc4c(cc3OC)C(=O)N3c5ccccc5C[C@H]3CN4)cc(NC(=O)[C@H](C)NC(=O)[C@H](C)NC(=O)CCCCC(=O)NCCN3C(=O)C=CC3=O)c1)N=C[C@@H]1Cc3ccccc3N1C2=O ; "D1"]

NHS ester 1a (8.2 mg, 7.6 μmol) (prepared according to procedures described in US 2016/0082114, incorporated herein by reference) and 1-(2-aminoethyl)-1H-pyrrole-2,5-dione hydrochloride (2.2 mg, 0.011 mmol) were dissolved in anhydrous dichloromethane (305 μL) at room temperature. DIPEA (2.66 μL, 0.015 mmol) was added and the reaction and was stirred for 3.5 hours. The reaction mixture was concentrated and was purified by RPHPLC (C18 column, $CH_3CN/H_2O$, gradient, 35% to 55%). The desired product fractions were frozen and lyophilized to give maleimide, compound D1 as a solid white powder (5.3 mg, 58% yield). LCMS=5.11 min (8 min method). MS (m/z): 1100.6 $(M+1)^+$.

B. Synthesis of N-(2-(2,5-dioxo-2,5-dihydro-1H-pyrrol-1-yl)ethyl)-11-(3-(a(S)-8-methoxy-6-oxo-11,12,12a,13-tetrahydro-6H-benzo[5,6][1,4]diazepino[1,2-a]indol-9-yl)oxy)methyl)-5-((((S)-8-methoxy-6-oxo-12a,13-dihydro-6H-benzo[5,6][1,4]diazepino[1,2-4]indol-9-yl)oxy)methyl)phenyl)-13,13-dimethyl-2,5,8-trioxa-14,15-dithia-11-azanonadecan-19-amide, Compound D2

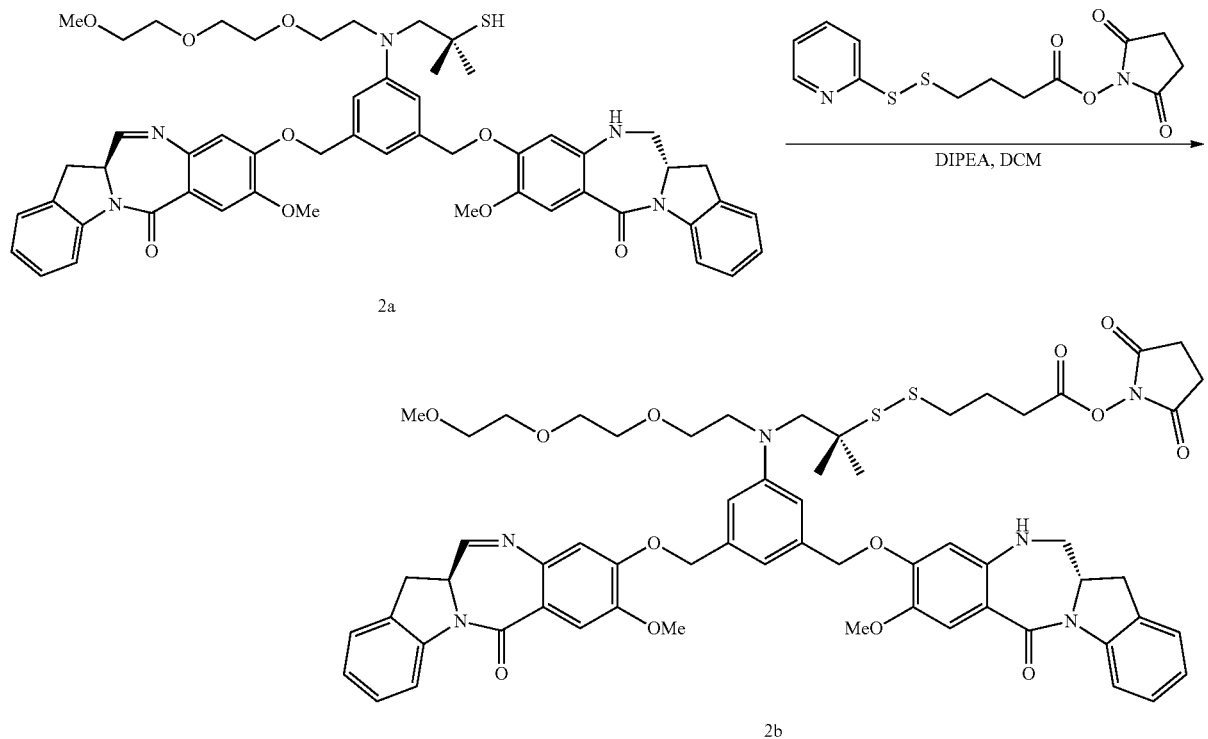

To a solution of the free thiol 2a (40 mg, 0.042 mmol) and NHS 4-(2-pyridyldithio)butanate (35 mg, 80% purity, 0.085 mmol) in anhydrous dichloromethane (0.5 mL) was added anhydrous diisopropylethylamine (0.015 mL, 0.085 mmol) and was stirred at room temperature for 16 hours. The reaction mixture was quenched with saturated ammonium chloride and diluted with dichloromethane. The obtained mixture was separated in a separatory funnel. The organic layer was washed with brine, dried over anhydrous sodium sulfate, filtered and stripped under reduced pressure. The residue was purified by semi-preparative reverse phase HPLC (C18 column, $CH_3CN/H_2O$). The fractions that contained pure product were combined, frozen and lyophilized to give the desired NHS ester, 2b (29.7 mg, 60% yield). LCMS=9.1 min (15 min method). MS (m/z): 1157.3 $(M+1)^+$.

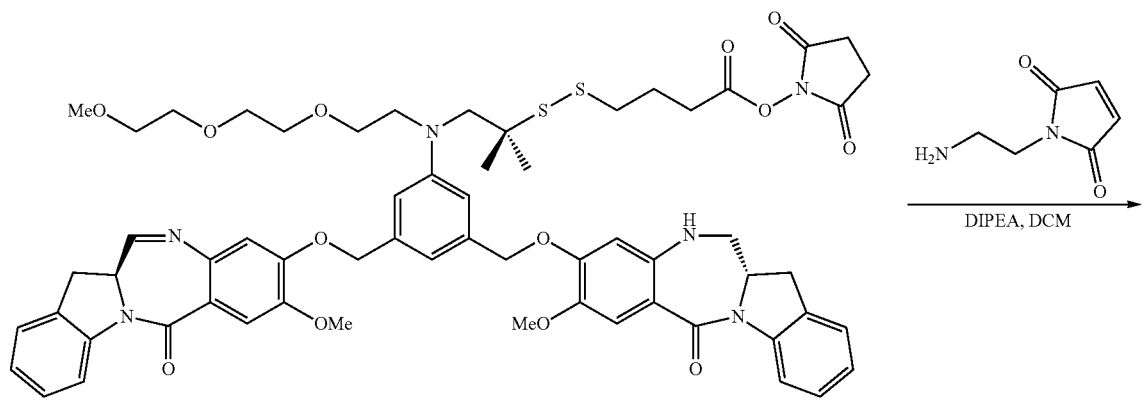

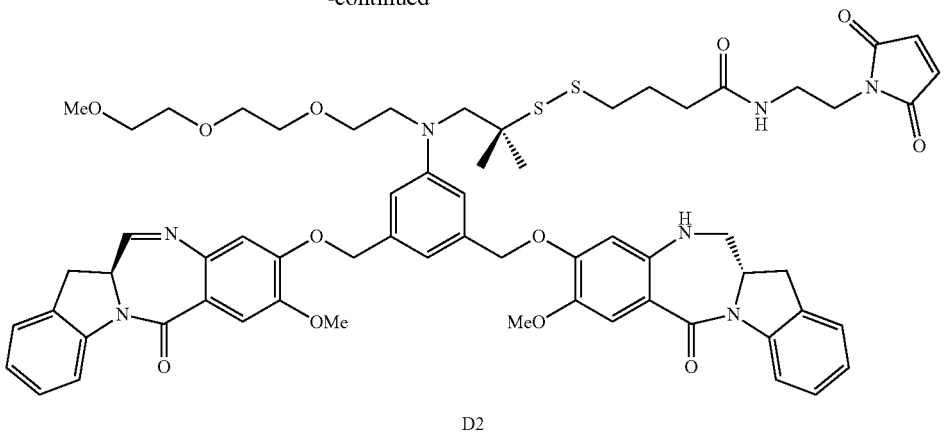

D2

To a solution of the NHS ester, 2b (12.3 mg, 0.011 mmol) and N-(2-aminoethyl)maleimide hydrochloride (2.0 mg, 0.011 mmol) in anhydrous dichloromethane (0.3 mL) was added DIPEA (0.0022 mL, 0.013 mmol). The mixture was stirred at room temperature for 3 hours then it was stripped under reduced pressure. The residue was purified by semi-preparative reverse phase HPLC (C18 column, $CH_3CN$/$H_2O$). The fractions that contained pure product were combined, frozen and lyophilized to give the desired maleimide, compound D2 (10 mg, 80% yield). LCMS=8.3 min (15 min method). MS (m/z): 1181.8 $(M+1)^+$.

C. Synthesis of 1-((2-(2,5-dioxo-2,5-dihydro-1H-pyrrol-1-yl)ethyl)amino)-4-((5-((3-(a(S)-8-methoxy-6-oxo-11,12,12a,13-tetrahydro-6H-benzo[5,6][1,4]diazepino[1,2-a]indol-9-yl)oxy)methyl)-5-((((S)-8-methoxy-6-oxo-12a,13-dihydro-6H-benzo[5,6][1,4]diazepino[1,2-a]indol-9-yl)oxy)methyl)phenyl)amino)-2-methyl-5-oxopentan-2-yl)disulfanyl)-1-oxobutane-2-sulfonic Acid, Compound D3

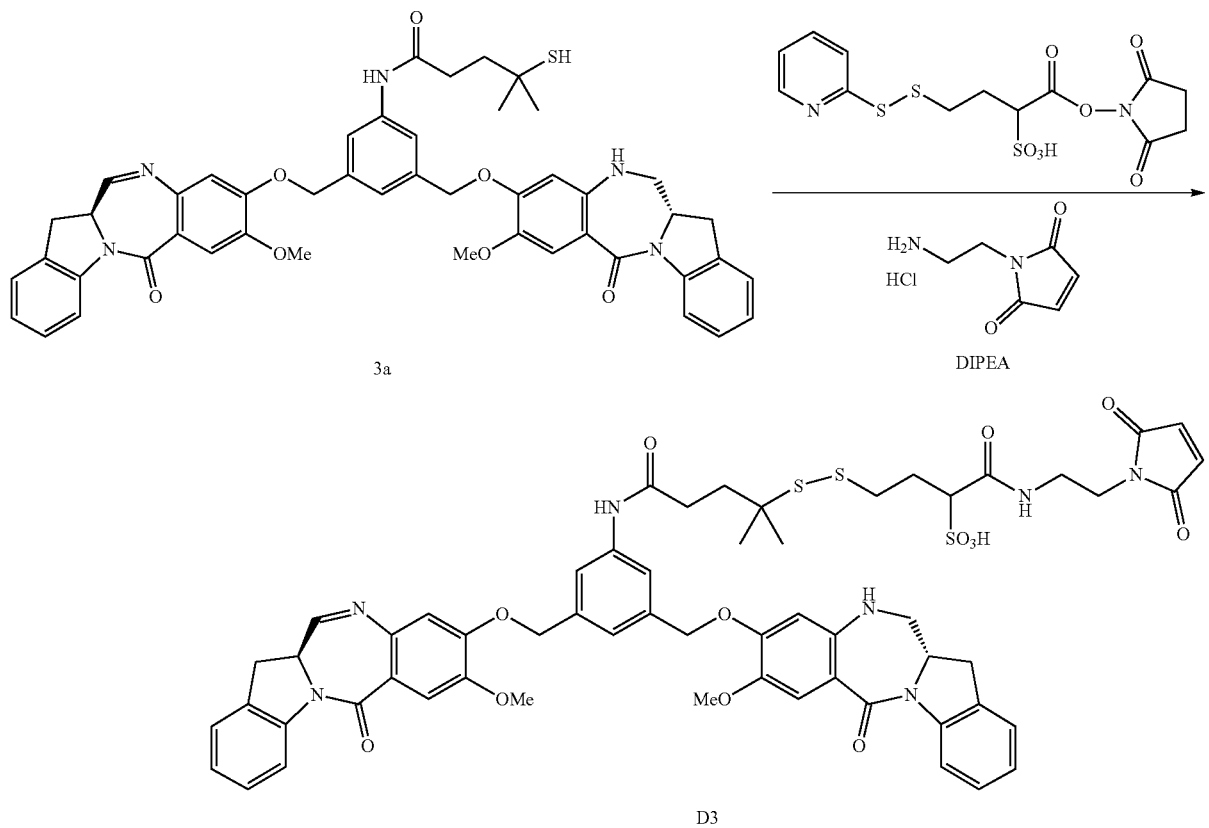

To a suspension of the free thiol, 3a (88 mg, 0.105 mmol) and 1-((2,5-dioxopyrrolidin-1-yl)oxy)-1-oxo-4-(pyridin-2-yldisulfanyl)butane-2-sulfonic acid (64.0 mg, 0.158 mmol) in anhydrous dichloromethane (2.10 mL) was added DIPEA (55.0 µL, 0.315 mmol) under nitrogen at room temperature. The mixture stirred for 16 hours and then 1-(2-aminoethyl)-1H-pyrrole-2,5-dione hydrochloride (55.6 mg, 0.315 mmol), anhydrous dichloromethane (1.0 mL) and DIPEA (0.055 mL, 0.315 mmol) were added. The mixture stirred for an additional 5 hours at room temperature upon which the reaction was concentrated in vacuo. The resulting residue was purified by RP-HPLC (C18, $CH_3CN/H_2O$). Fractions containing desired product were frozen and lyophilized to give maleimide, compound D3 (20 mg, 16% yield) as a white solid. LCMS=4.92 min (8 min method). MS (m/z): 1158.6 $(M+1)^+$.

D. Synthesis of N-(2-(2,5-dioxo-2,5-dihydro-1H-pyrrol-1-yl)ethyl)-11-(3-((((S)-8-methoxy-6-oxo-11,12,12a,13-tetrahydro-6H-benzo[5,6][1,4]diazepino[1,2-a]indol-9-yl)oxy)methyl)-5-((((S)-8-methoxy-6-oxo-12a,13-dihydro-6H-benzo[5,6][1,4]diazepino[1,2-a]indol-9-yl)oxy)methyl)phenyl)-2,5,8-trioxa-11-azapentadecan-15-amide, Compound D4

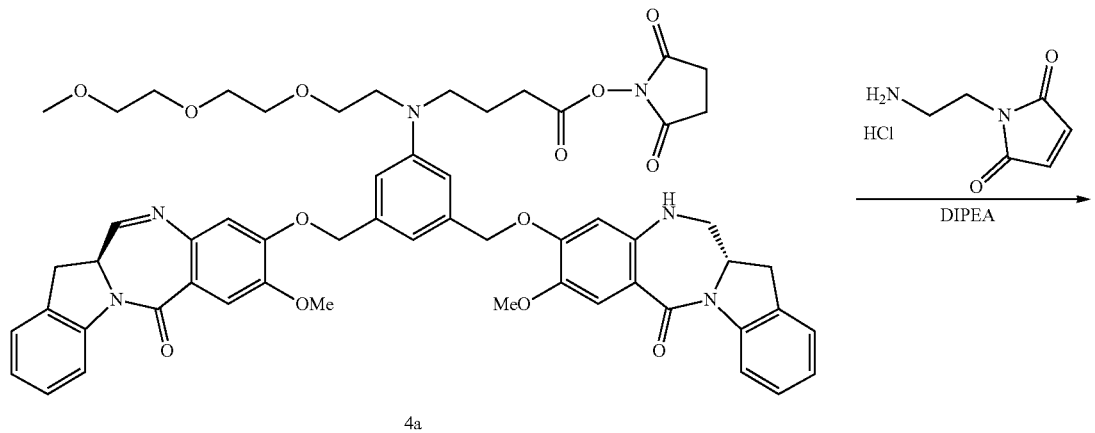

4a

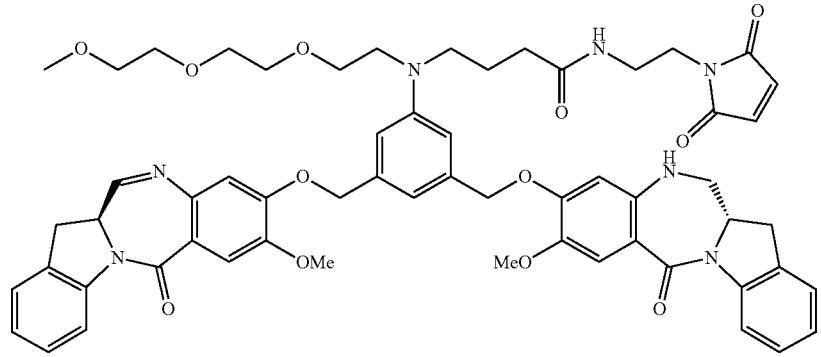

D4

To a solution of NHS ester, 4a (5 mg, 4.82 µmol) and 1-(2-aminoethyl)-1H-pyrrole-2,5-dione hydrochloride (1.7 mg, 9.64 µmol) in anhydrous dichloromethane (200 µL) was added DIPEA (1.512 µL, 8.68 µmol) under nitrogen. The mixture was stirred at room temperature for 4 hours and then concentrated in vacuo. The resulting residue was purified by RP-HPLC (C18, $CH_3CN/H_2O$). Fractions containing desired product were frozen and lyophilized to give maleimide, compound D4 (3.5 mg, 68% yield). LCMS=4.61 min (15 min method). MS (m/z): 1062.8 $(M+1)^+$.

Example 2. Selective Sulfonation of Imine-Containing Cytotoxic Agent Bearing Maleimide Group To a mixture of 50 mM sodium succinate pH 3.3 (116.5 mL) and DMA (98.5 mL) was added D1 (263.6 mg) dissolved in 21.4 mL of DMA. Subsequently 3.4 mL of a 100 mM sodium bisulfite solution (1.4 equivalents) in water containing 1 v/v % DMA was introduced into the reaction. The homogenous mixture was allowed to react for 2 h at 25° C., at which time completeness of the reaction was assayed by UPLC-MS. The reaction mixture is suitable for conjugation without further purification. As shown in FIG. 1, UPLC-MS analysis of the reaction mixture shows 92.5% imine-sulfo D1, 1.9% unreacted D1, 0.8% maleimide-sulfo D1, and 4.8% di-sulfo D1. ESI-MS negative ion mode $[M-H]^-$ calcd. for imine-sulfo D1 ($C_{60}H_{62}N_9O_{15}S^-$): 1180.41; found: 1180.03.

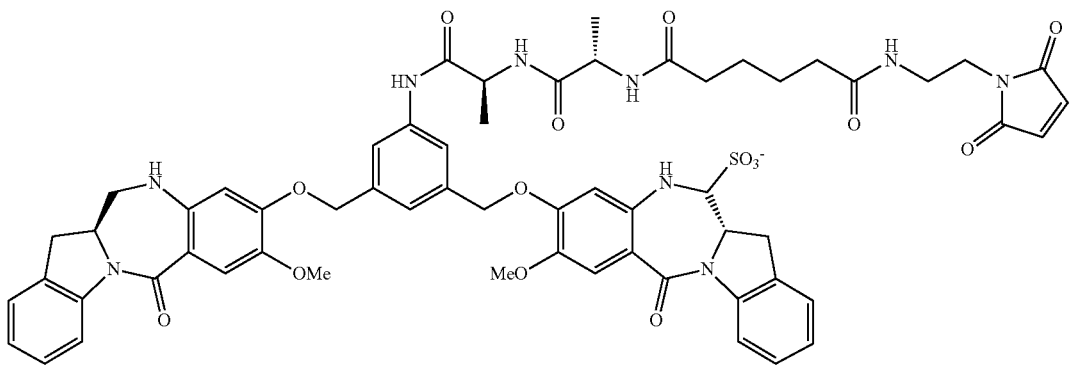

imine-sulfo D1

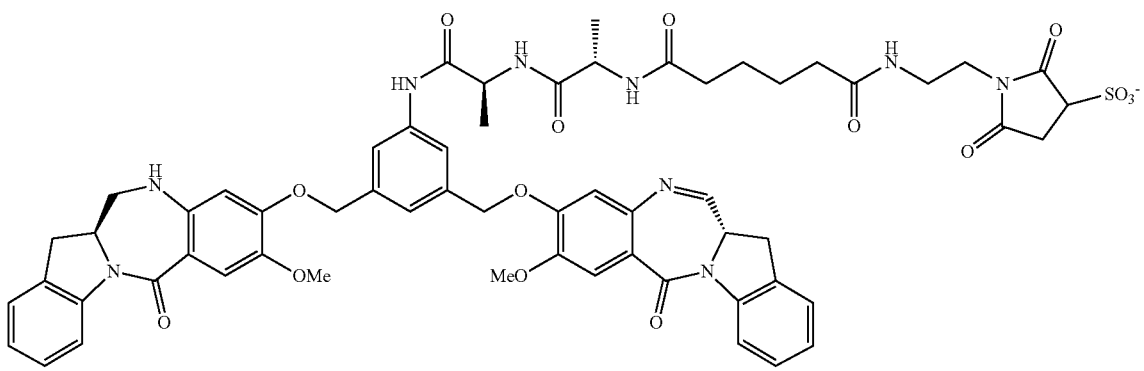

maleimide-sulfo D1

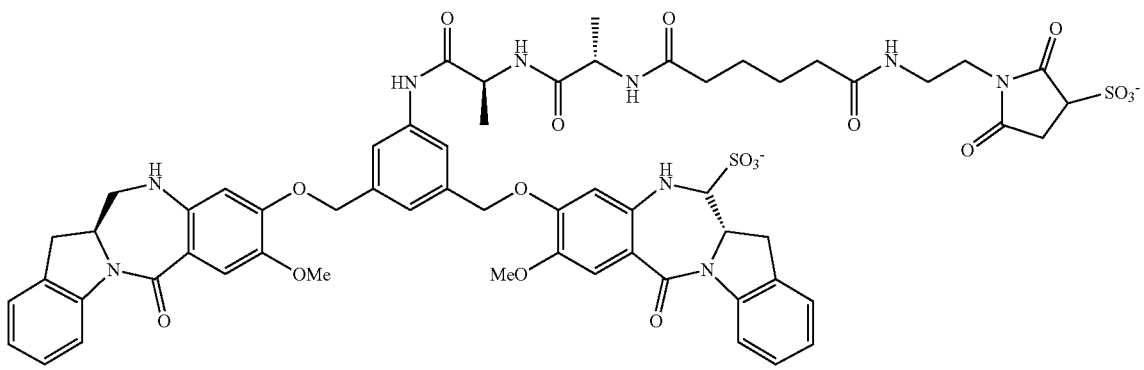

di-sulfo D1

Example 3. Effect of Sodium Bisulfite on Selective Sulfonation

As indicated in Table 1, to the required volume of 50 mM sodium succinate pH 3.3 buffer was added the following reagents in the following order: DMA (38.8 uL), the required volume of 20 or 40 mM aqueous sodium bisulfite stock containing 1 v/v % DMA, and 8.9 mM D1 in DMA (11.2 uL). The resulting reaction mixture containing 50% DMA by volume was allowed to react for 20 h at 25° C. The reaction products were analyzed by UPLC-MS. The relative abundances of the observed di-sulfo D1, maleimide-sulfo D1, imine-sulfo D1, and unsulfonated D1 products are shown in Table 1.

TABLE 1

| | | Sodium Bisulfite stock | | D1 Reaction products (%) | | | | Total |
|---|---|---|---|---|---|---|---|---|
| Reaction | Sodium Succinate buffer (uL) | Total equivalents | Stock concentration (mM) | Volume added (uL) | Di-sulfo | Maleimide-sulfo | Imine-sulfo | Unsul-fonated | reactive maleimide remaining |
| 1 | 46 | 0.8 | 20 | 4 | 0.6 | 1.4 | 35.9 | 62.1 | 98.0 |
| 2 | 45 | 1.0 | 20 | 5 | 1.1 | 1.4 | 53.4 | 44.2 | 97.6 |
| 3 | 44 | 1.2 | 20 | 6 | 2.0 | 1.2 | 69.6 | 27.2 | 96.8 |
| 4 | 43 | 1.4 | 20 | 7 | 2.6 | 1.1 | 79.1 | 17.2 | 96.3 |
| 5 | 42 | 1.6 | 20 | 8 | 5.0 | 1.1 | 85.7 | 8.2 | 93.9 |
| 6 | 41 | 1.8 | 20 | 9 | 8.3 | 1.2 | 84.6 | 5.9 | 90.5 |
| 7 | 45 | 2.0 | 40 | 5 | 8.7 | 0.8 | 88.2 | 2.3 | 90.5 |
| 8 | 44 | 2.4 | 40 | 6 | 13.0 | 0.9 | 83.9 | 2.2 | 86.1 |
| 9 | 43 | 2.8 | 40 | 7 | 16.4 | 1.1 | 79.8 | 2.7 | 82.5 |
| 10 | 42 | 3.2 | 40 | 8 | 19.8 | 1.5 | 75.8 | 2.9 | 78.7 |
| 11 | 41 | 3.6 | 40 | 9 | 22.9 | 1.8 | 71.9 | 3.4 | 75.3 |

Example 4. Effect of pH on Selective Sulfonation

As detailed in Table 2, to 44.0 uL of 50 mM sodium succinate buffer with the indicated pH was added the following reagents in the following order: 20 mM aqueous sodium bisulfite stock (6.0 uL) containing 1% v/v DMA, DMA (38.8 uL), and 8.9 mM D1 in DMA (11.2 uL). The resulting reaction mixture containing 50% DMA by volume was allowed to react for 4 h at 25° C. The reaction products were analyzed by UPLC-MS. The relative abundances of the observed di-sulfo, maleimide-sulfo, imine-sulfo, and unsulfonated D1 products are shown in Table 2.

TABLE 2

| | | | DGN549-C Reaction products (%) | | | | Total |
|---|---|---|---|---|---|---|---|
| Reaction | Sodium Succinate buffer pH | Sodium Bisulfite (Total equivalents) | Di-sulfo | Maleimide-sulfo | Imine-sulfo | Unsul-fonated | reactive maleimide remaining |
| 1 | 2.9 | 1.2 | 0.7 | 1.0 | 68.5 | 29.8 | 98.3 |
| 2 | 3.1 | 1.2 | 0.8 | 1.3 | 65.0 | 33.0 | 97.9 |
| 3 | 3.3 | 1.2 | 1.1 | 1.7 | 66.9 | 30.3 | 97.1 |
| 4 | 3.4 | 1.2 | 1.3 | 1.4 | 66.5 | 30.7 | 97.3 |
| 5 | 3.7 | 1.2 | 2.3 | 2.7 | 65.6 | 29.4 | 94.9 |

Example 5. Selective Sulfonation with or without Buffer

As detailed in Table 3, to 21.6 uL of DMA was added 22.0 uL of water or 50 mM sodium succinate buffer with the indicated pH, 20 mM aqueous sodium bisulfite stock (3.0 uL) containing 1 v/v % DMA, and 14.5 mM D1 in DMA (3.4 uL). The resulting reaction mixture containing 50% DMA by volume was allowed to react for 6 h at 25° C. The reaction products were analyzed by UPLC-MS. The relative abundances of the observed di-sulfo, maleimide-sulfo, imine-sulfo, and unsulfonated D1 products are shown in Table 3.

TABLE 3

| | | | D1 Reaction products (%) | | | | Total |
|---|---|---|---|---|---|---|---|
| Reaction | Sodium Succinate buffer pH | Sodium Bisulfite (Total equivalents) | Di-sulfo | Maleimide-sulfo | Imine-sulfo | Unsul-fonated | reactive maleimide remaining |
| 1 | 3.5 | 1.2 | 0.8 | 0.5 | 86.9 | 11.8 | 98.7 |
| 2 | 4.0 | 1.2 | 4.8 | 2.9 | 70.0 | 22.8 | 92.8 |
| 3 | water only | 1.2 | 2.8 | 1.8 | 75.8 | 19.6 | 95.4 |

Figure 2:
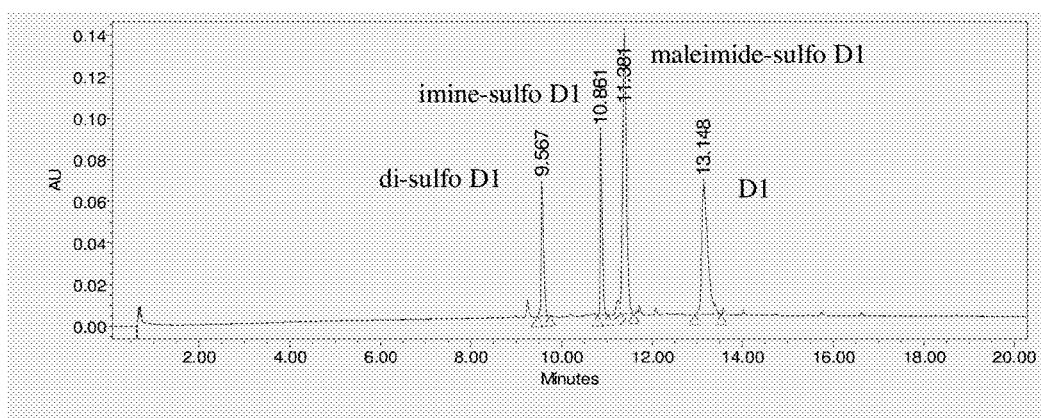
FIG. 2 shows an UPLC chromatogram of the reaction mixture of imine-containing cytotoxic agent D1 with sodium bisulfite at pH 4.75.

Similarly, as detailed in Table 4, to 47.6 uL of DMA was added 55.6 uL of water or pH 4.75 50 mM sodium succinate buffer, 20 mM aqueous sodium bisulfite stock (6.9 uL) containing 1 v/v % DMA, and 8.4 mM D1 in DMA (14.9 uL). The resulting reaction mixture containing 50% DMA by volume was allowed to react for 24 h at 25° C. The reaction products were analyzed by UPLC-MS (see FIG. 2). The relative abundances of the observed di-sulfo, maleimide-sulfo, imine-sulfo, and unsulfonated DGN549-C products are indicated in Table 4.

TABLE 4

| Reaction | Sodium Succinate buffer pH | Sodium Bisulfite (Total equivalents) | D1 Reaction products (%) | | | | Total reactive maleimide remaining |
| --- | --- | --- | --- | --- | --- | --- | --- |
| | | | Di-sulfo | Maleimide-sulfo | Imine-sulfo | Unsul-fonated | |
| 1 | 4.75 | 1.1 | 9.8 | 40.7 | 13.4 | 36.1 | 49.5 |
| 3 | water only | 1.1 | 1.5 | 0.9 | 73.8 | 23.8 | 97.6 |

In another experiment, as detailed in Table 5, to 24.6 uL of DMA was added the indicated volume of water, the indicated volume of 20 mM aqueous sodium bisulfite stock. The pH of these solutions was as indicated in Table 5. To these mixtures was added 11.2 mM D1 in DMA (5.4 uL). The resulting reaction mixtures containing 50% DMA by volume were allowed to react for 1 to 2 h at 25° C. The reaction products were analyzed by UPLC-MS. The relative abundances of the observed di-sulfo, maleimide-sulfo, imine-sulfo, and unsulfonated D1 products are indicated in Table 5.

TABLE 5

| Reaction | Water (uL) | Sodium Bisulfite stock | | | Observed reaction pH | DGN549-C Reaction products (%) | | | | Total reactive maleimide remaining |
| --- | --- | --- | --- | --- | --- | --- | --- | --- | --- | --- |
| | | Total equivalents | Stock concentration (mM) | Volume added (uL) | | Di-sulfo | Maleimide-sulfo | Imine-sulfo | Unsul-fonated | |
| 1 | 21.0 | 3.0 | 20 | 9.0 | 4.2 | 6.9 | — | 90.9 | 2.2 | 93.1 |
| 2 | 15.0 | 5.0 | 20 | 15.0 | 4.2 | 20.5 | — | 78.0 | 1.5 | 79.5 |

"—" means not observed by UPLC.

Example 6. Preparation of Antibody-Cytotoxic Agent Conjugates

The sulfonation reaction mixture (240 mL, 3.5 equiv.) prepared according to Example 2 was subsequently introduced into a 50 mM potassium phosphate pH 6.0 solution containing 10 g of anti-CD123 antibody with reduced C442 engineered cysteine residues. At a final concentration of 2 mg/mL antibody and 15 v/v % DMA, the conjugation reaction was allowed to proceed for 18 h at 25° C. SEC analysis of the reaction product gives ADC with a DAR (drug to antibody ratio) of 1.9 and a % HMW (percentage of high molecule weight species) of 4.4% vs. 3.7% prior to conjugation.

Conjugates with two other humanized monoclonal antibodies with reduced C442 engineered cysteine residues were also prepared according to similar procedures described above.

Figure 3:
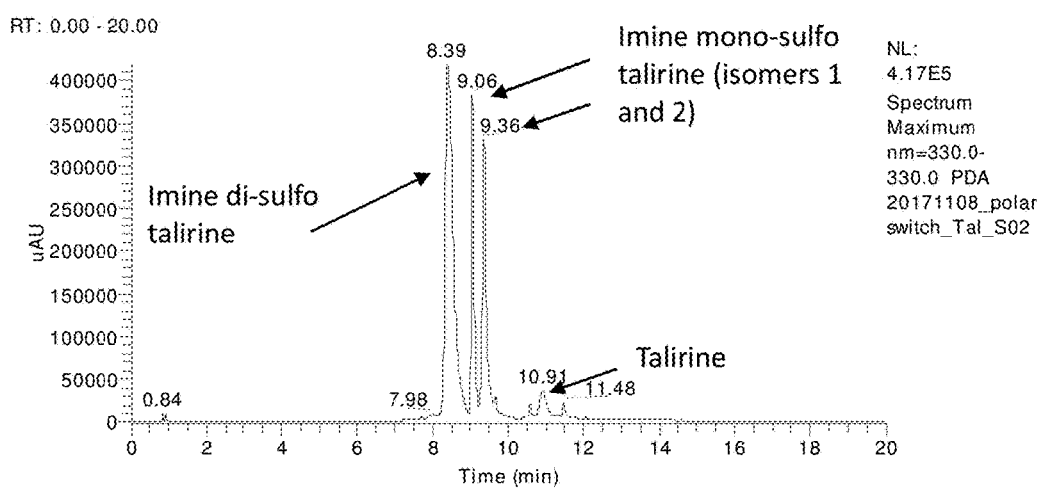
FIG. 3 shows an UPLC chromatogram of the reaction mixture of a PBD imine-containing cytototoxic agent talirine with sodium bisulfite.

Example 7. Selective Sulfonation of Imine-Containing PBD Dimers Bearing Maleimide Group To 21.2 μL of 50 mM sodium succinate pH 3.3 buffer was added in the following order: 20 μL of DMA, 3.8 μL of 20 mM aqueous sodium bisulfite stock, and 5.0 μL of 10.0 mM talirine in DMA. This corresponds to 1.5 equivalents of bisulfite with respect to talirine. The resulting reaction mixture containing 50% DMA by volume was allowed to react for 4 h at 25° C. The reaction products were analyzed by UPLC-MS. The relative abundances of the observed imine di-sulfo, total imine mono-sulfo, unsulfonated, and total maleimide-sulfo products were determined as indicated in Table 6. ESI-MS calcd. for talirine ($C_{60}H_{65}N_8O_{12}^+$) $[M+H]^+$ 1089.4716, found 1089.4716; calcd. for imine mono-sulfonated talirine ($C_{60}H_{65}N_8O_{15}S^-$) $[M-H]^-$ 1169.4296, found 1169.4345; calcd. for imine di-sulfonated talirine ($C_{60}H_{67}N_8O_{18}S_2^-$) $[M-H]^-$ 1251.4020, found 1251.4053. A representative chromatogram (absorbance at 330 nm) of the final reaction mixture is shown in FIG. 3. Structures of the identified reaction products are

TABLE 6

| Reaction | Sodium Succinate buffer (uL) | Sodium Bisulfite stock | | | Talirine Reaction products (%) | | | | |
| --- | --- | --- | --- | --- | --- | --- | --- | --- | --- |
| | | Total equivalents (vs payload) | Stock concentration (mM) | Volume added (uL) | Imine di-sulfo | Imine mono-sulfo | Total maleimide-sulfo species | Unsul-fonated | Total reactive maleimide remaining |
| talirine | 21.2 | 1.5 | 20 | 3.8 | 57.3 | 39.0 | <1 | 3.7 | >99.0 |

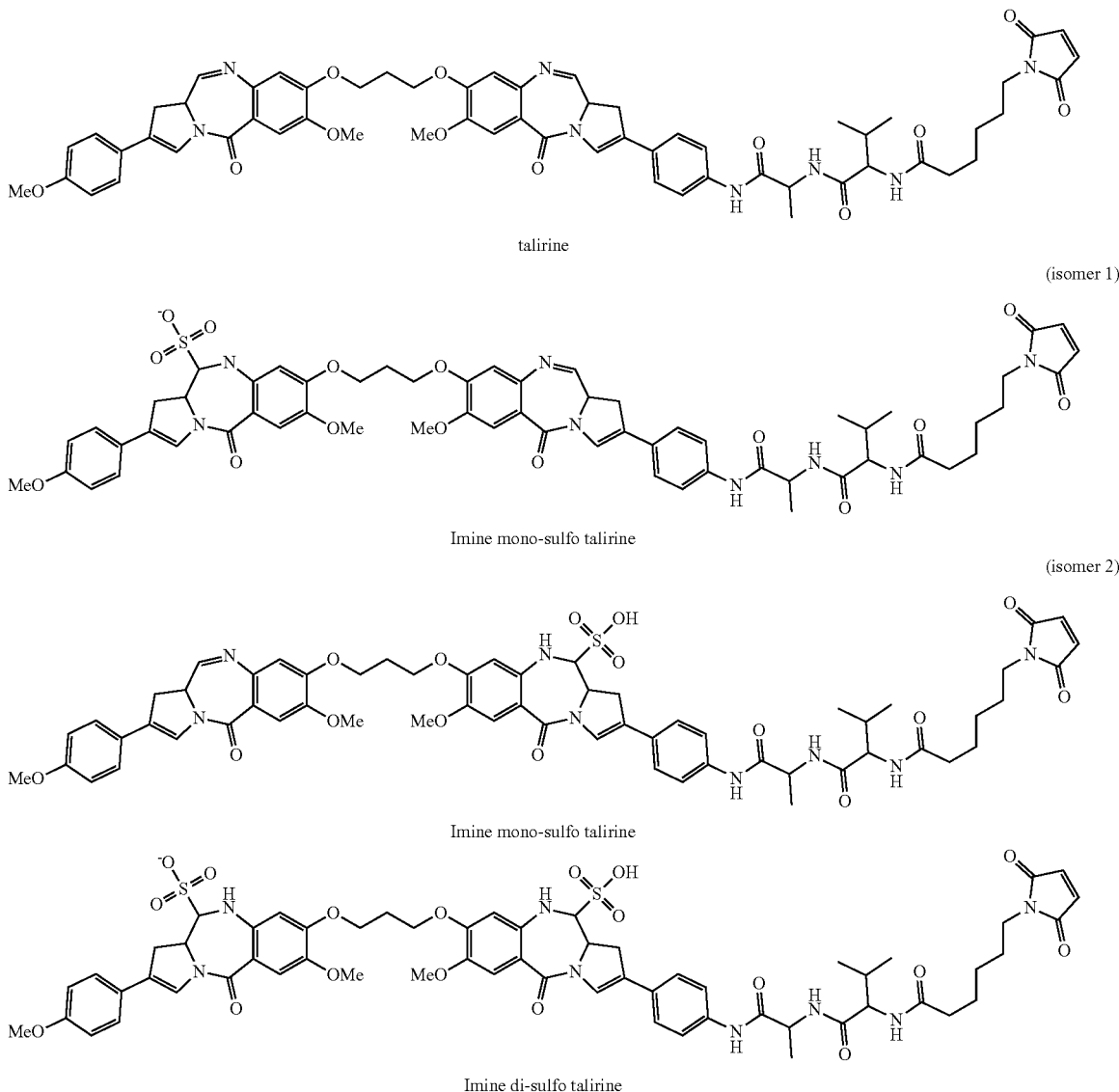

talirine (isomer 1)

Imine mono-sulfo talirine (isomer 2)

Imine mono-sulfo talirine

Imine di-sulfo talirine

Example 8. Selective Sulfonation of Imine-Containing IGN Dimers Bearing Maleimide Group As indicated in Table 7, to the required volume of 50 mM sodium succinate pH 3.3 buffer was added in the following order: DMA (21.2 uL), the required volume of 20 mM aqueous sodium bisulfite stock, and 13.2 mM D5 in DMA (3.8 uL). The resulting reaction mixture containing 50% DMA by volume was allowed to react for 4 h at 25° C. The reaction products were analyzed by UPLC-MS. The relative abundances of the observed imine di-sulfo, imine mono-sulfo, unsulfonated, and total maleimide-sulfonated products were determined as indicated in Table 7. ESI-MS calcd. for D5 ($C_{60}H_{60}N_9O_{12}^+$) [M+H]$^+$ 1098.4356, found 1098.4351; calcd. for imine mono-sulfonated D5 ($C_{60}H_{60}N_9O_{15}S^-$) [M−H]$^-$ 1178.3935, found 1178.4006; calcd. for imine di-sulfonated D5 ($C_{60}H_{62}N_9O_{18}S_2^-$)

Figure 4A:
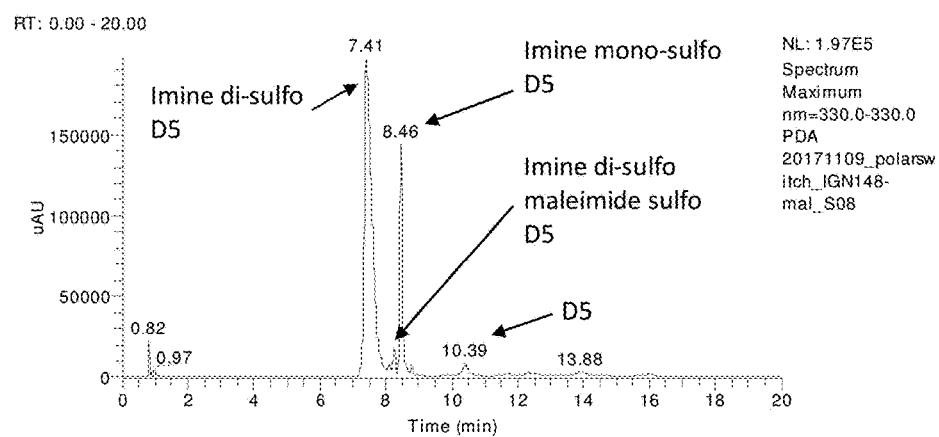
FIGS. 4A and 4B show UPLC chromatograms of the reaction mixture of an imine-containing cytotoxic agent D5 with 2.0 (FIG. 4A) or 2.5 (FIG. 4B) equivalents of sodium bisulfite.
Figure 4B:
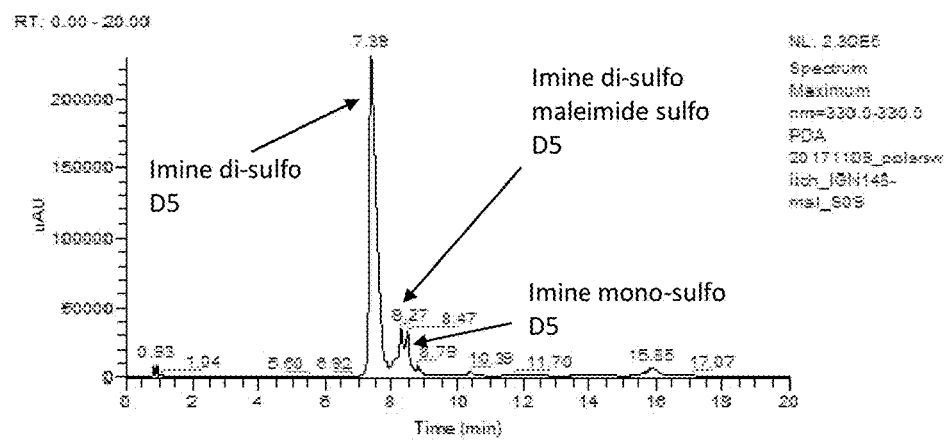

[M−H]⁻ 1260.3660, found 1260.3704; calcd. for imine di-sulfonated maleimide sulfonated D5 ($C_{60}H_{64}N_9O_{21}S_3^-$) [M-2H]²⁻ z=2 670.6653, found 670.6693. Representative chromatograms (absorbance at 330 nm) of the final reaction mixture with 2.0 and 2.5 equivalents of bisulfite are shown in FIGS. 4A and 4B. Structures of the identified reaction products are shown below.

TABLE 7

| | Sodium Succinate buffer (uL) | Sodium Bisulfite stock | | | IGN148-mal Reaction products (%) | | | | |
| --- | --- | --- | --- | --- | --- | --- | --- | --- | --- |
| | | Total equivalents (vs payload) | Stock concentration (mM) | Volume added (uL) | Imine di-sulfo | Imine mono-sulfo | maleimide-sulfo species | Unsulfonated | Total reactive maleimide remaining |
| Reaction | | | | | | | | | |
| 1 | 21.2 | 1.5 | 20 | 3.8 | 41.9 | 46.9 | 1.4 | 9.7 | 98.6 |
| 2 | 20.0 | 2.0 | 20 | 5.0 | 76.0 | 20.3 | 1.9 | 1.8 | 98.1 |
| 3 | 18.7 | 2.5 | 20 | 6.3 | 83.3 | 6.7 | 10.0 | — | 90.0 |

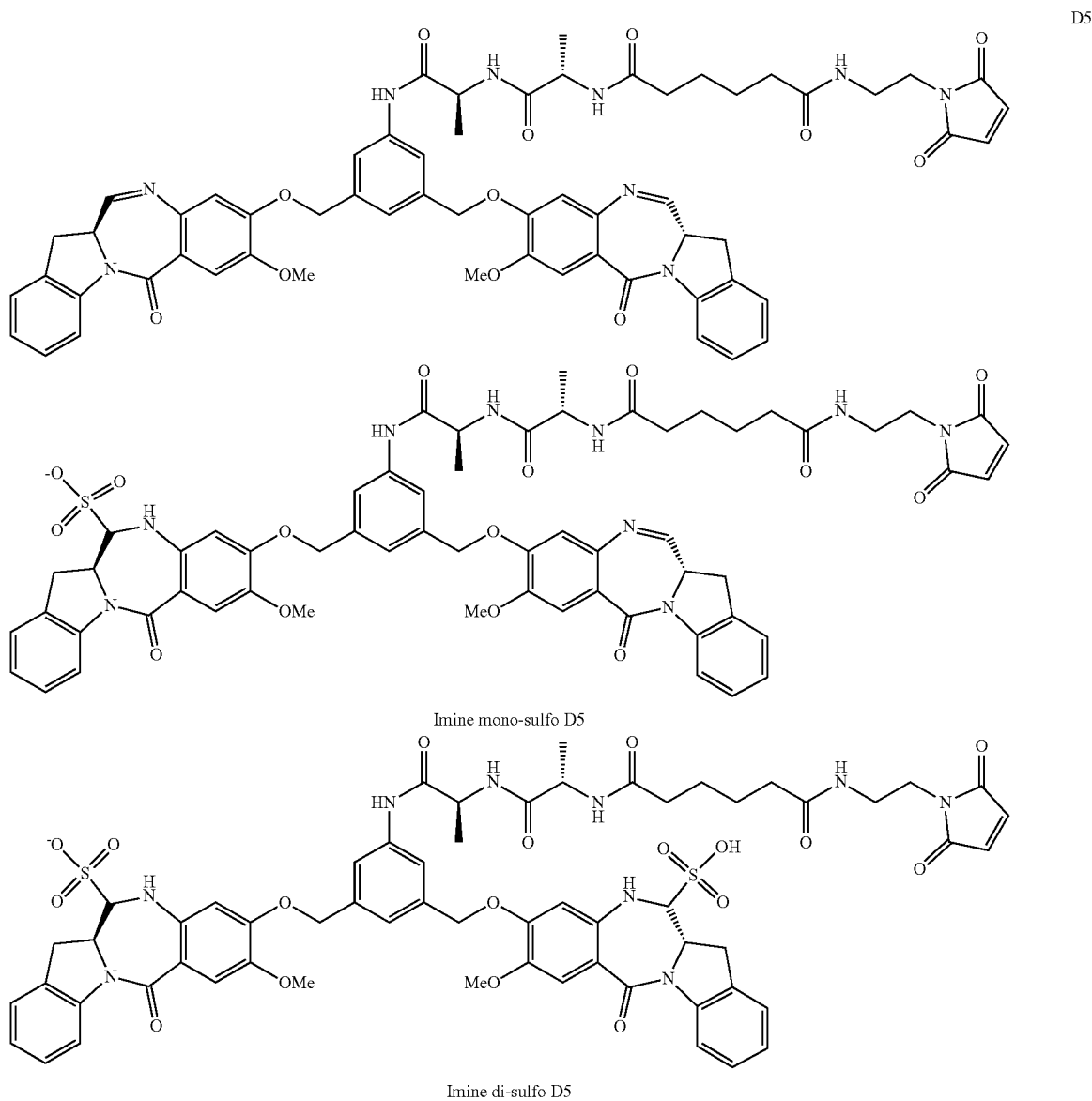

Imine mono-sulfo D5

Imine di-sulfo D5

-continued

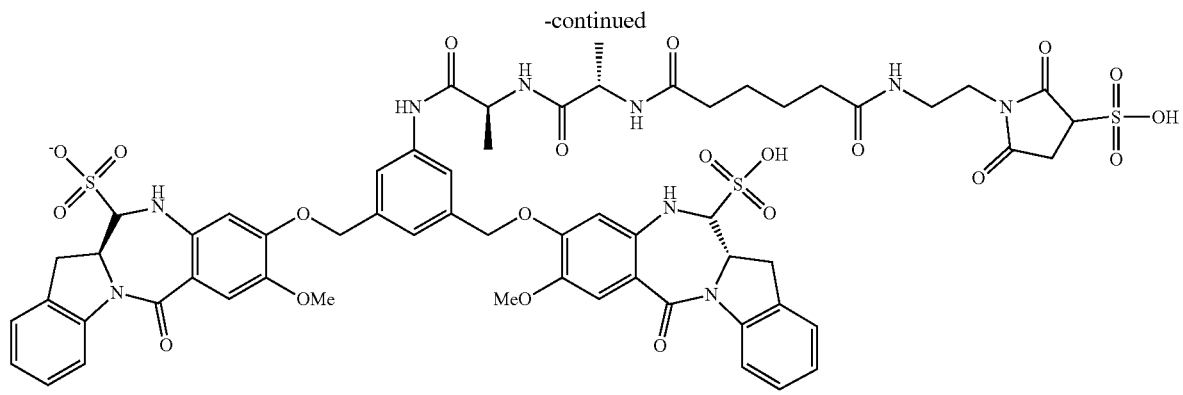

Imine di-sulfo maleimide D5

We claim:

1. A method of preparing a cell-binding agent-cytotoxic agent conjugate comprising the steps of:
   (a) reacting an imine-moiety in an imine-containing cytotoxic agent represented by the following formula:

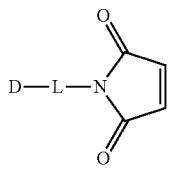

or a pharmaceutically acceptable salt thereof, with sulfur dioxide, a bisulfite salt or a metabisulfite salt in an aqueous solution at a pH of 1.9 to 5.0 to form a modified cytotoxic agent comprising a modified imine moiety represented by the following formula:

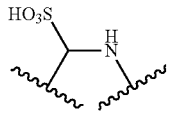

or a pharmaceutically acceptable salt thereof; and
   (b) reacting the modified cytotoxic agent with a cell-binding agent to form the cell-binding agent-cytotoxic agent conjugate,
   wherein D is an imine-containing benzodiazepine compound; and L is a linker.

2. The method of claim 1, wherein D is an imine-containing indolinobenzodiazepine or an imine-containing pyrrolobenzodiazepine (PBD) compound.

3. The method of claim 1, wherein the reaction of step (a) is carried out at a pH of 2.9 to 4.0, a pH of 2.9 to 3.7, a pH of 3.1 to 3.5, a pH of 3.2 to 3.4, or a pH of 3.3.

4. The method of claim 1, wherein the reaction of step (a) is carried out in the presence of a buffer solution.

5. The method of claim 1, wherein:
0.5 to 5 equivalents of the bisulfite salt or 0.25 to 2.5 equivalents of the metabisulfite salt is reacted with 1 equivalent of the imine-containing cytotoxic agent;
0.8 to 2.0 equivalents of the bisulfite salt or 0.4 to 1.0 equivalents of the metabisulfite salt is reacted with 1 equivalent of the imine-containing cytotoxic agent;
1.1 to 1.6 equivalents of the bisulfite salt or 0.55 to 0.8 equivalents of the metabisulfite salt is reacted with 1 equivalent of the imine-containing cytotoxic agent; or
wherein 1.4 equivalents of the bisulfite salt or 0.7 equivalent of the metabisulfite salt is reacted with 1 equivalent of the imine-containing cytotoxic agent.

6. The method of claim 1, wherein the reaction of step (a) is carried out at:
(i) a pH of 2.9 to 3.7 and 1.0 to 1.8 equivalents of the bisulfite salt or 0.5 to 0.9 equivalent of the metabisulfite salt is reacted with 1 equivalent of the imine-containing cytotoxic agent;
(ii) a pH of 3.1 to 3.5 and 1.1 to 1.6 equivalents of the bisulfite salt or 0.55 to 0.8 equivalent of the metabisulfite salt is reacted with 1 equivalent of the imine-containing cytotoxic agent; or
(iii) a pH of 3.3 and 1.4 equivalents of the bisulfite salt or 0.7 equivalent of the metabisulfite salt is reacted with 1 equivalent of the imine-containing cytotoxic agent.

7. The method of claim 1, wherein the reaction of step (a) is carried out in a mixture of an organic solvent and water.

8. The method of claim 7, wherein the reaction of step (a) is carried out in a mixture of dimethylacetamide (DMA) and water.

9. The method of claim 1, wherein in step (a), the imine-containing cytotoxic agent is reacted with sodium bisulfite or sodium metabisulfite.

10. The method of claim 1, wherein the modified cytotoxic agent is not purified before reacting with the cell-binding agent in step (b).

11. The method of claim 1, wherein the reaction of step (b) is carried out at a pH of 4 to 9, a pH of 5 to 8.5, or a pH of 5.5 to 6.5.

12. The method of claim 1, wherein D is represented by the following formula:

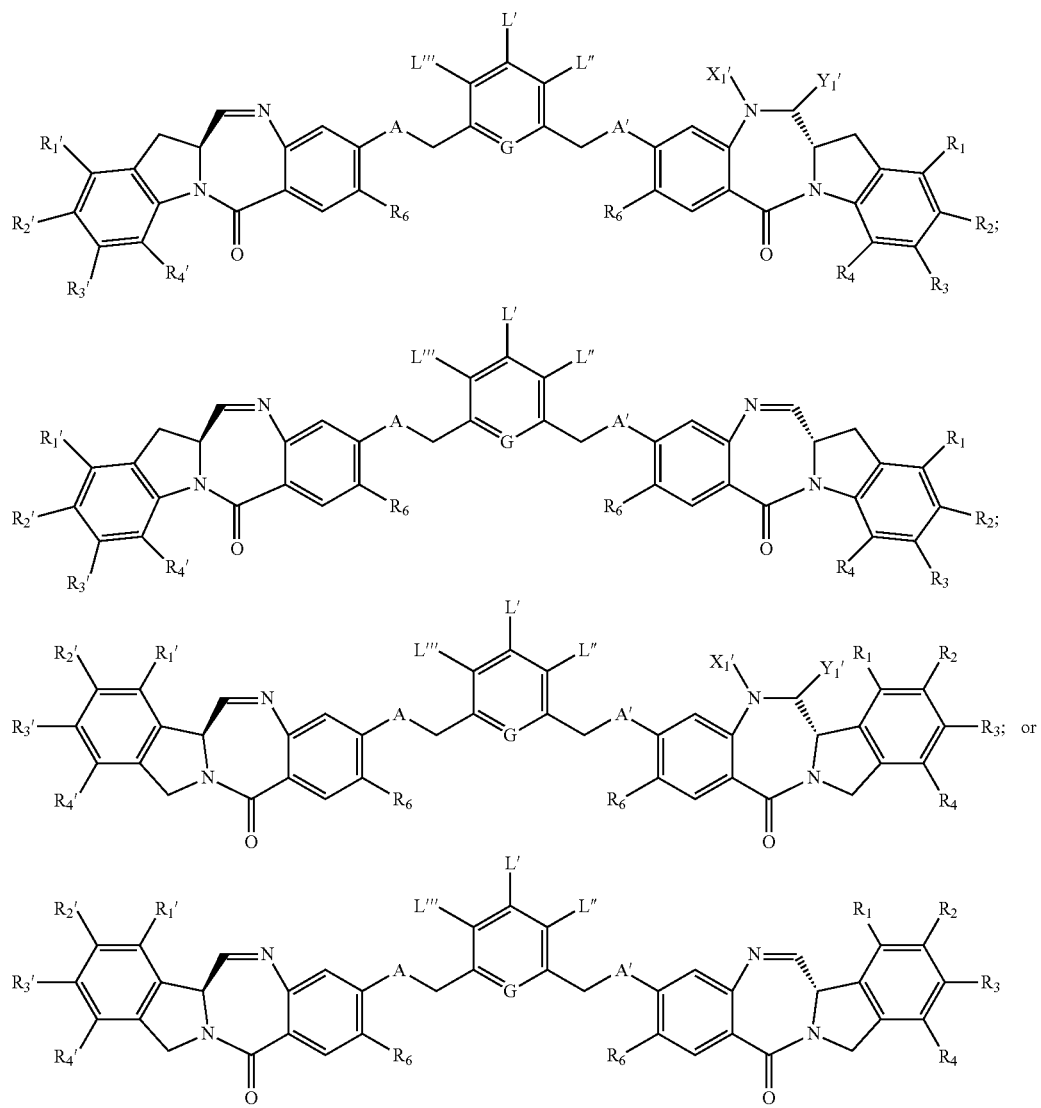

or a pharmaceutically acceptable salt thereof, wherein:
one of L', L", and L'" is represented by the following formula:

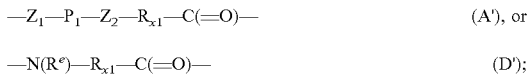

$-Z_1-P_1-Z_2-R_{x1}-C(=O)-$ (A'), or $-N(R^e)-R_{x1}-C(=O)-$ (D');

and the other two are each independently selected from —H, an optionally substituted linear, branched or cyclic alkyl, alkenyl or alkynyl having from 1 to 10 carbon atoms, a polyethylene glycol unit $-(CH_2CH_2O)_n-R^c$, halogen, guanidinium [—NH(C=NH)NH$_2$], —OR, —NR'R", —NO$_2$, —NR'COR", —SR, —SOR', —SO$_2$R', —SO$_3$H, —OSO$_3$H, —SO$_2$NR'R", cyano, an azido, —COR', —OCOR', and —OCONR'R";

one of the $Z_1$ and $Z_2$ is —C(=O)—, and the other is —NR$_5$—;

$P_1$ is an amino acid residue or a peptide containing between 2 to 20 amino acid residues;

$R_{x1}$ is an optionally substituted linear, branched or cyclic alkyl, alkenyl or alkynyl having from 1 to 10 carbon atoms;

$R^e$ is —H, a linear, branched or cyclic alkyl, alkenyl or alkynyl having 1 to 10 carbon atoms or $-(CH_2-CH_2-O)_n-R^k$, wherein $R^k$ is a —H, a linear, branched cyclic alkyl having 1 to 6 carbon atoms, optionally bearing a secondary amino (e.g., —NHR$^{101}$) or tertiary amino (—NR$^{101}$R$^{102}$) group or a 5- or 6-membered nitrogen containing heterocycle, wherein $R^{101}$ and $R^{102}$ are each independently a linear, branched, or cyclic alkyl, alkenyl or alkynyl having 1 to 10 carbon atoms;

R, for each occurrence, is independently selected from the group consisting of —H, an optionally substituted linear, branched or cyclic alkyl, alkenyl or alkynyl having from 1 to 10 carbon atoms, a polyethylene glycol unit $-(CH_2CH_2O)_n-R^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit $-(CH_2CH_2O)_n-R^c$, and an optionally substituted 3- to 18-membered heterocyclic ring having 1 to 6 heteroatoms independently selected from O, S, N and P;

$R^c$ is —H or an optionally substituted linear or branched alkyl having 1 to 4 carbon atoms;

n is an integer from 1 to 24;

$X_1'$ is selected from —H, an amine-protecting group, an optionally substituted linear, branched or cyclic alkyl, alkenyl or alkynyl having 1 to 10 carbon atoms, a polyethylene glycol unit $-(CH_2CH_2O)_n-R^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

$Y_1'$ is selected from —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms;

$R_1$, $R_2$, $R_3$, $R_4$, $R_1'$, $R_2'$, $R_3'$ and $R_4'$ are each independently selected from the group consisting of —H, an optionally substituted linear, branched or cyclic alkyl, alkenyl or alkynyl having from 1 to 10 carbon atoms, a polyethylene glycol unit $-(CH_2CH_2O)_n-R^c$, halogen, guanidinium [—NH(C=NH)NH$_2$], —OR, —NR'R", —NO$_2$, —NCO, —NR'COR", —SR, —SOR', —SO$_2$R', —SO$_3^-$H, —OSO$_3$H, —SO$_2$NR'R", cyano, an azido, —COR', —OCOR', and —OCONR'R";

$R_6$ is —H, —R, —OR, —SR, —NR'R", —NO$_2$, or halogen;

G is —CH— or —N—;

A and A' are the same or different, and are independently selected from —O—, oxo (—C(=O)—), —CRR'O—, —CRR'—, —S—, —CRR'S—, —NR$_5$ and —CRR'N(R$_5$)—; and $R_5$ for each occurrence is independently —H or an optionally substituted linear or branched alkyl having 1 to 10 carbon atoms.

13. The method of claim 12, wherein L" and L'" are both —H'; and L' is represented by the following formula:

$-NR_5-P_1-C(=O)-(CR_aR_b)_s-C(=O)-$ (B1');

$-NR_5-P_1-C(=O)-Cy-(CR_aR_b)_{s1'}-C(=O)-$ (B2');

$-C(=O)-P_1-NR_5-(CR_aR_b)_s-C(=O)-$ (C1'), or $-C(=O)-P_1-NR_5-Cy-(CR_aR_b)_{s1'}-C(=O)-$ (C2')

wherein:
$R_a$ and $R_b$, for each occurrence, are each independently —H, (C$_1$-C$_3$)alkyl or a charged substituent or an ionizable group Q;

s is an integer from 1 to 6;

s1' is 0 or an integer from 1 to 6; and

Cy is a cyclic alkyl having 5 or 6 ring carbon atoms optionally substituted with halogen, —OH, (C$_1$-C$_3$) alkyl, (C$_1$-C$_3$)alkoxy, or halo(C$_1$-C$_3$)alkyl.

14. The method of claim 13, wherein:
$R_1$, $R_2$, $R_3$, $R_4$, $R_1'$, $R_2'$, $R_3'$ and $R_4'$ are all —H;
$R_6$ is —OMe;
$X_1'$ and $Y_1'$ are both —H; and
A and A' are —O—.

15. The method claim 13, wherein -L- is represented by the following structural formula:

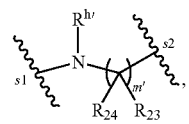

or a pharmaceutically acceptable salt thereof, wherein:
s1 is the site covalently linked to D; s2 is the site covalently linked to the maleimide group;
$R_{23}$ and $R_{24}$, for each occurrence, are independently H or an optionally substituted alkyl;
m' is an integer between 0 and 10; and
$R^{h'}$ is H or an optionally substituted alkyl.

16. The method of claim 1, wherein the imine-containing cytotoxic agent is represented by the following formula:

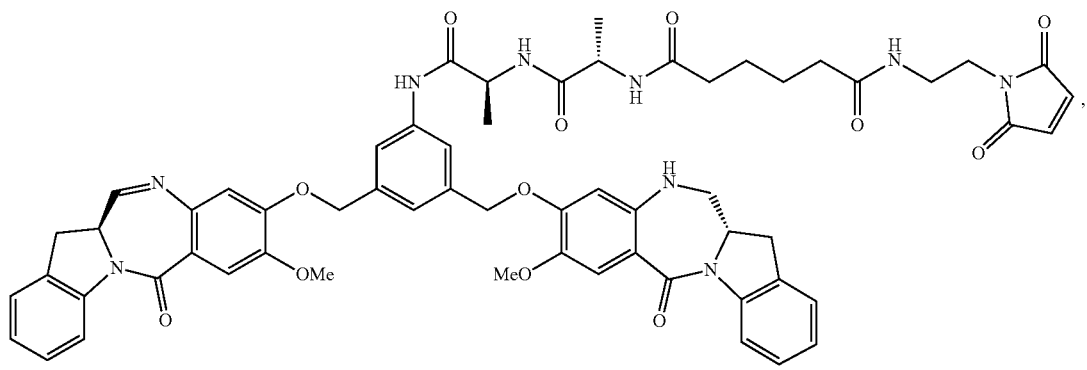 [SMILES: COc1cc2c(cc1OCc1cc(COc3cc4c(cc3OC)C(=O)N3c5ccccc5C[C@H]3CN4)cc(NC(=O)[C@H](C)NC(=O)[C@H](C)NC(=O)CCCCC(=O)NCCN3C(=O)C=CC3=O)c1)N=C[C@@H]1Cc3ccccc3N1C2=O]
or a pharmaceutically acceptable salt thereof, and the modified cytotoxic agent is represented by the following formula:
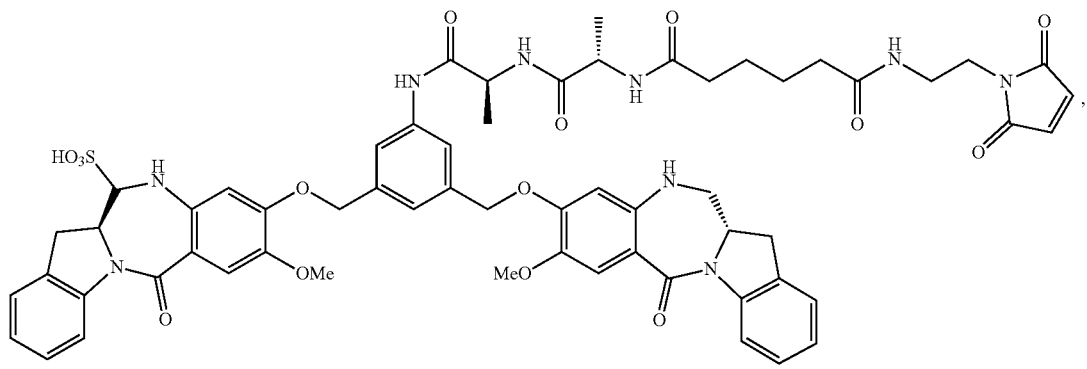
or a pharmaceutically acceptable salt thereof.
17. The method of claim 1, wherein D is represented by the following formula:
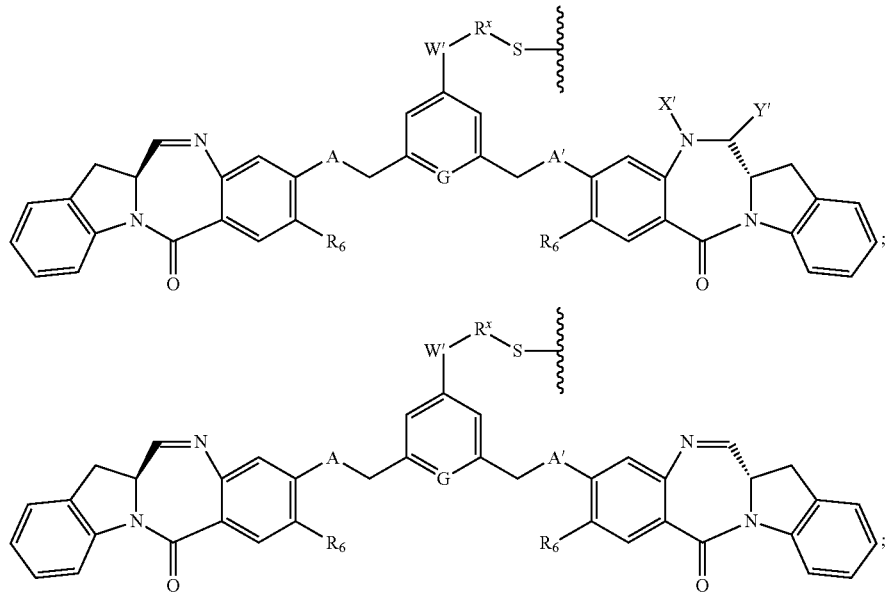

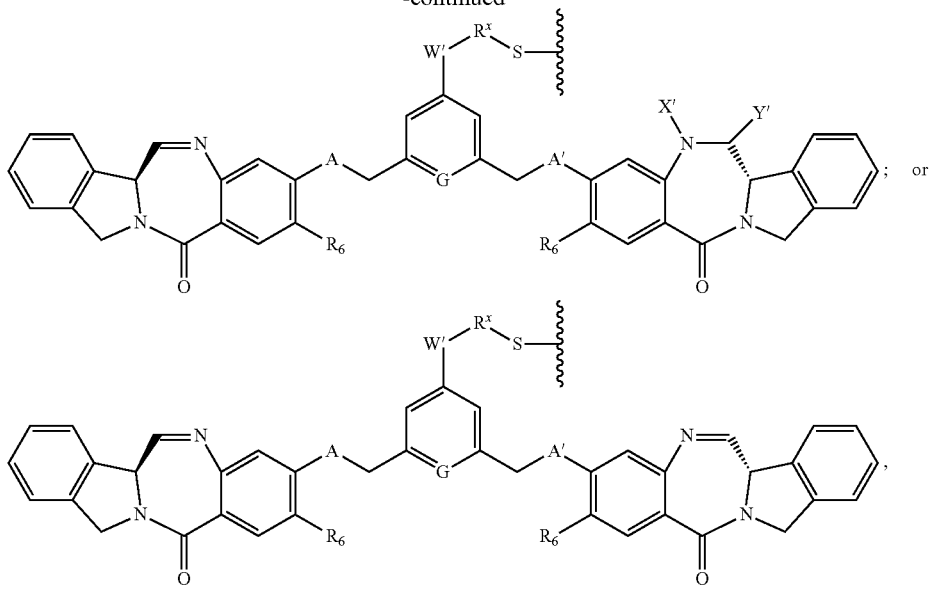

or a pharmaceutically acceptable salt thereof, wherein:
- X' is selected from the group consisting of —H, —OH, a substituted or unsubstituted linear, branched or cyclic alkyl, alkenyl or alkynyl having from 1 to 10 carbon atoms, phenyl, and an amine-protecting group;
- Y' is selected from the group consisting of —H, an oxo group, a substituted or unsubstituted linear, branched or cyclic alkyl, alkenyl or alkynyl having from 1 to 10 carbon atoms;
- A and A' are selected from —O— and —S—;
- W' is absent, or selected from —O—, —N($R^e$)—, —N($R^e$)—C(=O)—, —N(C(=O)$R^e$)—, —S— or —CH$_2$—S—, —CH$_2$N$R^e$—;
- $R^x$ is absent or selected from a linear, branched or cyclic alkyl having 1 to 10 carbon atoms;
- $R^e$ is —H, a linear, branched or cyclic alkyl, alkenyl or alkynyl having 1 to 10 carbon atoms or —(CH$_2$—CH$_2$—O)$_n$—$R^k$, wherein $R^k$ is a —H, a linear, branched cyclic alkyl having 1 to 6 carbon atoms, optionally bearing a secondary amino (e.g., —NHR$^{101}$) or tertiary amino (—NR$^{101}$R$^{102}$) group or a 5- or 6-membered nitrogen containing heterocycle, wherein R$^{101}$ and R$^{102}$ are each independently a linear, branched, or cyclic alkyl, alkenyl or alkynyl having 1 to 10 carbon atoms;
- n is an integer from 1 to 24;
- G is selected from —CH— or —N—;
- R$_6$ is —H, —R, —OR, —SR, —NR'R", —NO$_2$, or halogen; and
- R is —H, an optionally substituted linear, branched or cyclic alkyl, alkenyl or alkynyl having from 1 to 10 carbon atoms or a PEG group —(CH$_2$CH$_2$O)$_n$—$R^c$, wherein n is an integer from 1 to 24, and $R^c$ is a linear or branched alkyl having 1 to 4 carbon atoms;
- R' and R" are each independently selected from —H, —OH, —OR, —NRR$^{g'}$, —COR, an optionally substituted linear, branched or cyclic alkyl, alkenyl or alkynyl having from 1 to 10 carbon atoms, an optionally substituted aryl having from 6 to 18 carbon atoms, an optionally substituted 3- to 18-membered heterocyclic ring having 1 to 6 heteroatoms selected from O, S, N and P, a PEG group —(CH$_2$CH$_2$O)$_n$—$R^c$, and $R^{g'}$ is —H, an optionally substituted linear, branched or cyclic alkyl, alkenyl or alkynyl having from 1 to 10 carbon atoms or a PEG group —(CH$_2$CH$_2$O)$_n$—$R^c$.

18. The method of claim 1, wherein D is represented by the following formula:

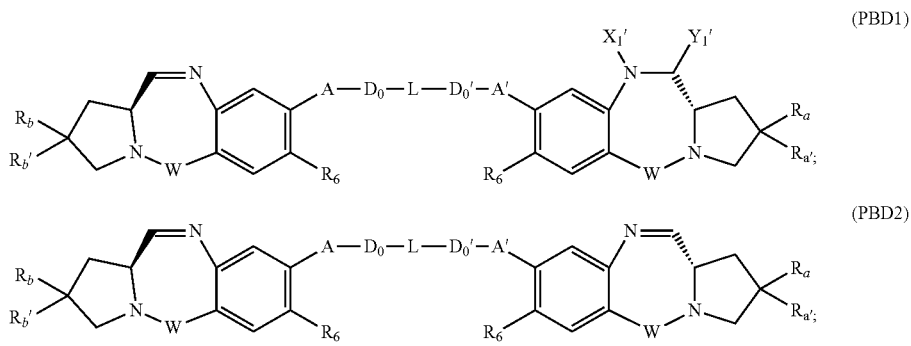

(PBD1)

(PBD2)

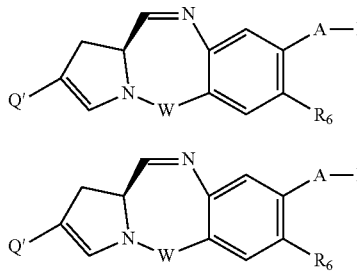

(PBD3)

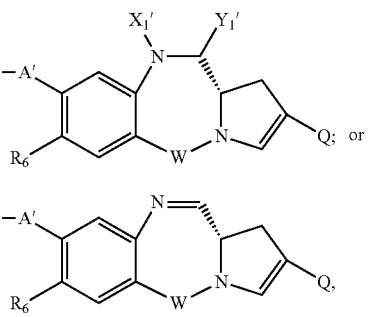

(PBD4)

or a pharmaceutically acceptable salt thereof, wherein:

W is selected from C=O, C=S, $CH_2$, BH, SO and $SO_2$;

$X_1'$ is selected from —H, an amine-protecting group, an optionally substituted linear, branched or cyclic alkyl, alkenyl or alkynyl having from 1 to 10 carbon atoms, a polyethylene glycol unit —$(CH_2CH_2O)_n$—$R^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

$Y_1'$ is selected from —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms;

$R_6$ is —H, —R, —OR, —SR, —NR'R", —$NO_2$, or halogen;

A and A' are the same or different, and are independently selected from —O—, oxo (—C(=O)—), —CRR'O—, —CRR'—, —S—, —CRR'S—, —$NR_5$ and —CRR'N($R_5$)—, R, for each occurrence, is independently selected from the group consisting of —H, an optionally substituted linear, branched or cyclic alkyl, alkenyl or alkynyl having from 1 to 10 carbon atoms, a polyethylene glycol unit —$(CH_2CH_2O)_n$—$R^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —$NR_2$, —COR, an optionally substituted linear, branched or cyclic alkyl, alkenyl or alkynyl having 1 to 10 carbon atoms, a polyethylene glycol unit —$(CH_2CH_2O)_n$—$R^c$, and an optionally substituted 3- to 18-membered heterocyclic ring having 1 to 6 heteroatoms independently selected from O, S, N and P;

$R^c$ is —H or a substituted or unsubstituted linear or branched alkyl having 1 to 4 carbon atoms, or the linking group with the reactive group bonded thereto;

n is an integer from 1 to 24;

$R_5$ for each occurrence is independently —H or an optionally substituted linear or branched alkyl having 1 to 10 carbon atoms;

$D_0$ and $D_0'$ are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—$OCH_2CH_2$)_n—;

L is absent, a linker, a polyethylene glycol unit (—$OCH_2CH_2$)_n—, an optionally substituted linear, branched or cyclic alkyl or alkenyl having 1 to 10 carbon atoms, an optionally substituted phenyl group, an optionally substituted 3 to 18-membered heterocyclic ring or a 5- to 18-membered heteroaryl ring having 1 to 6 heteroatoms independently selected from O, S, N and P;

$R_a$, $R_a'$, $R_b$ and $R_{b'}$ are the same or different, and are independently selected from the group consisting of —H, halide, or an optionally substituted branched, linear or cyclic alkyl having 1 to 10 carbon atoms; or $R_a$ and $R_{a'}$, and/or $R_b$ and $R_{b'}$ together form a double bond containing group =B and =B' respectively;

=B and =B' are the same or different and independently selected from an optionally substituted branched or linear alkenyl or a carbonyl group;

Q is $Q_1$-Ar-$Q_2$;

Q' is $Q_1'$-Ar'-$Q_2'$;

$Q_1$ and $Q_1'$ are each independently absent, a linear, branched or cyclic alkyl from 1 to 6 carbon atoms or a —CH=CH unit;

Ar and Ar' are each independently absent, or represent an aryl group;

$Q_2$ and $Q_2'$ are each independently selected from —H, a linker, a substituted or unsubstituted linear, branched or cyclic alkyl, alkenyl or alkynyl having from 1 to 10 carbon atoms, a polyethylene glycol unit —$R^{c'}$—$(OCH_2CH_2)_n$—$R^c$, or a substituent selected from a halogen, guanidinium [—NH(C=NH)$NH_2$], —R, —OR, —NR'R", —$NO_2$, —NCO, —NR'COR", —NR'(C=O)OR", —SR, a sulfoxide represented by —SOR', a sulfone represented by —$SO_2R'$, a sulfonate —$SO_3M$, a sulfate —OSO₃M, a sulfonamide represented by SO₂NR'R", cyano, an azido, —COR', —OCOR' or —OCONR'R"; and R$^{c'}$ is absent or selected from linear or branched alkyl, alkenyl or alkynyl having 1 to 5 carbon atoms.

19. The method of claim 1, wherein the imine-containing cytotoxic agent is represented by the following formula:

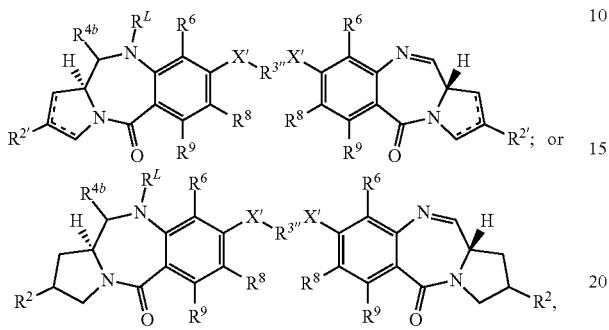

or a pharmaceutically acceptable salt thereof, wherein:
the dotted lines indicate the optional presence of a double bond;
R$^{3''}$ is a C$_{3-12}$ alkylene group,
each X', for each occurrence, is independently —O—, —S— or —N(H)—
each R² is independently selected from —H, —OH, —CN, —R$^{1'}$, —OR$^{1'}$, —O—SO₂—R$^{1'}$, —CO₂R$^{1'}$, —COR$^{1'}$, or halo, or both R² taken together, are =O, =CH₂, =CH—R$^a$, or =C(R$^a$)₂;
each R$^{2'}$ is independently selected from —H, —OH, —CN, —R$^{1'}$, —OR$^{1'}$, —O—SO₂—R$^{1'}$, —CO₂R$^{1'}$, —COR$^{1'}$ or halo;
R$^{4b}$ is a leaving group selected from —OR$^{6'}$, —OCOR$^{4'}$, —OCOOR$^{4'}$, —OCONR$^{4'}$R$^{5'}$, —NR$^{4'}$R$^{5'}$, —NR$^{4'}$COR$^{5'}$, —NR$^{4'}$NR$^{4'}$R$^{5'}$, an optionally substituted 5- or 6-membered nitrogen-containing heterocycle (e.g., piperidine, tetrahydropyrrole, pyrazole, morpholine), a guanidinum represented by —NR$^{4'}$(C=NH)NR$^{4'}$R$^{5'}$, an amino acid, or a peptide represented by —NR$^{6'}$COP', wherein P' is an amino acid or a polypeptide containing between 2 to 20 amino acid units, —SR$^{6'}$, —SOR$^{4'}$, —SO₂M, —SO₃M, —OSO₃M, halogen, cyano and an azido;

R$^L$ is linker bearing a maleimide moiety that can form a covalent bond with a cell binding agent (CBA);

R⁶ and R⁹ are independently selected from —H, —R$^{1'}$, —OH, —OR$^{1'}$, —SH, —SR$^{1'}$, —NH₂, —NHR$^{1'}$, —NR$^{1'}$R$^{3'}$, —NO₂, Me₃Sn and halo; and, R$^{1'}$ and R$^{3'}$ are each independently selected from optionally substituted C$_{1-12}$ alkyl, C$_{3-20}$ heterocyclyl or C$_{5-20}$ aryl groups, and optionally in relation to the group —NR$^{1'}$R$^{3'}$, R$^{1'}$ and R$^{3'}$ together with the nitrogen atom to which they are attached form an optionally substituted 4-, 5-, 6- or 7-membered heterocyclic ring; or any pair of adjacent groups from R⁶ to R⁹ together form a group —O—(CH₂)$_p$—O—, where p is 1 or 2;

R$^{4'}$ and R$^{5'}$ are each independently selected from —H, —OH, —OR$^{6'}$, —NHR$^{6'}$, —NR$^{6'}$₂, —COR$^{6'}$, an optionally substituted linear, branched or cyclic alkyl, alkenyl or alkynyl having from 1 to 10 carbon atoms, a polyethylene glycol unit —(CH₂CH₂O)$_n$—R$^b$, or an optionally substituted 3-18-membered heterocyclic ring having 1 to 6 heteroatoms independently selected from O, S, N or P;

R$^{6'}$, for each occurrence, is independently selected from the group consisting of —H, an optionally substituted linear, branched or cyclic alkyl, alkenyl or alkynyl having from 1 to 10 carbon atoms, a polyethylene glycol unit —(CH₂CH₂O)$_n$—R$^b$, an optionally substituted aryl having 6 to 18 carbon atoms, an optionally substituted 5- to 18-membered heteroaryl ring containing one or more heteroatoms independently selected from nitrogen, oxygen, or sulfur, and an optionally substituted 3- to 18-membered heterocyclic ring containing 1 to 6 heteroatoms independently selected from O, S, N or P;

R$^a$ is independently selected from —R$^{1'}$, —CO₂R$^{1'}$, —COR$^{1'}$, —CHO, —CO₂H, or halo;

R$^b$ is —H or a substituted or unsubstituted linear or branched alkyl having 1 to 4 carbon atoms;

M is H or a pharmaceutically acceptable cation; and n is an integer from 1 to 24.

* * * * *